US009254286B2

(12) United States Patent
Abelson et al.

(10) Patent No.: US 9,254,286 B2
(45) Date of Patent: Feb. 9, 2016

(54) OPHTHALMIC FORMULATIONS OF CETIRIZINE AND METHODS OF USE

(75) Inventors: Mark B. Abelson, Andover, MA (US); Matthew J. Chapin, Amesbury, MA (US); Paul Gomes, Haverhill, MA (US); George Minno, Suwanee, GA (US); Jackie Nice, Medford, MA (US)

(73) Assignee: Aciex Therapeutics, Inc., Boston, MA (US)

(*) Notice: Subject to any disclaimer, the term of this patent is extended or adjusted under 35 U.S.C. 154(b) by 847 days.

(21) Appl. No.: 12/724,128

(22) Filed: Mar. 15, 2010

(65) Prior Publication Data
US 2010/0240625 A1 Sep. 23, 2010

Related U.S. Application Data

(60) Provisional application No. 61/161,006, filed on Mar. 17, 2009, provisional application No. 61/174,850, filed on May 1, 2009.

(51) Int. Cl.
| A61K 31/495 | (2006.01) |
| A61K 9/00 | (2006.01) |
| A61K 9/08 | (2006.01) |
| A61K 31/4965 | (2006.01) |
| A61K 31/56 | (2006.01) |

(52) U.S. Cl.
CPC ............ *A61K 31/495* (2013.01); *A61K 9/0048* (2013.01); *A61K 9/08* (2013.01); *A61K 31/4965* (2013.01); *A61K 31/56* (2013.01)

(58) Field of Classification Search
CPC .. A61K 31/495; A61K 31/56; A61K 31/4965
See application file for complete search history.

(56) References Cited

U.S. PATENT DOCUMENTS

| 4,407,791 | A | 10/1983 | Stark |
| 4,525,358 | A * | 6/1985 | Baltes et al. ............. 514/255.04 |
| 5,188,826 | A | 2/1993 | Chandrasekaran et al. |
| 5,419,898 | A | 5/1995 | Ikejiri et al. |
| 5,698,558 | A | 12/1997 | Gray |
| 6,103,735 | A | 8/2000 | Aslanian et al. |
| 6,436,924 | B2 | 8/2002 | Poppe et al. |
| 6,649,602 | B1 | 11/2003 | Yanni |
| 6,827,946 | B2 | 12/2004 | Hirsh |
| 2002/0037297 | A1 | 3/2002 | Crespo et al. |
| 2004/0198743 | A1 | 10/2004 | Hey et al. |
| 2004/0198828 | A1 | 10/2004 | Abelson et al. |
| 2005/0239745 | A1 | 10/2005 | Abelson et al. |
| 2006/0025391 | A1 | 2/2006 | Lulla et al. |
| 2006/0183698 | A1 | 8/2006 | Abelson |
| 2006/0216353 | A1 | 9/2006 | Liversidge et al. |
| 2006/0228306 | A1 | 10/2006 | Lane |
| 2006/0263350 | A1 | 11/2006 | Lane |
| 2007/0020330 | A1 | 1/2007 | Dang et al. |
| 2007/0275974 | A1 | 11/2007 | Fanara et al. |
| 2008/0085922 | A1 | 4/2008 | Raja et al. |
| 2008/0254029 | A1 | 10/2008 | Yanni et al. |

FOREIGN PATENT DOCUMENTS

| EP | 0433766 | A1 | 6/1991 |
| EP | 0920315 | B1 | 6/1999 |
| JP | 6-239748 | | 8/1994 |
| JP | 2009-507009 | | 2/2009 |
| RU | 2220740 | C1 | 1/2004 |
| WO | WO-9746243 | A1 | 12/1997 |
| WO | WO 98/06394 | A1 | 2/1998 |
| WO | WO-9915203 | A1 | 4/1999 |
| WO | WO-03049770 | A1 | 6/2003 |
| WO | WO-2004066960 | A2 | 8/2004 |
| WO | WO-2004069338 | A1 | 8/2004 |
| WO | WO-2005030331 | A1 | 4/2005 |
| WO | WO-2005107711 | A2 | 11/2005 |
| WO | WO-2006102494 | A2 | 9/2006 |
| WO | WO 2007/026151 | A1 | 3/2007 |
| WO | WO-2007117971 | A2 | 10/2007 |

OTHER PUBLICATIONS

Abelson et al., "A Randomized, Double-Blind, Parallel-Group Comparison of Olopatadine 0.1% Ophthalmic Solution Versus Placebo for Controlling the Signs and Symptoms of Seasonal Allergic Conjuctivitis and Rhinoconjunctivitis", *Clinical Therapeutics*, 25(3):931-947 (2003).
Crampton et al., "A Comparison of the Relative Clinical Efficacy of a Single Dose of Ketotifen Fumarate 0/025% Ophthalmic Solution Versus Placebo in Inhibiting the Signs and Symptoms of Allergic Rhinoconjunctivitis as Induced by the Conjunctival Allergen Challenge Model", *Clinical Therapeutics*, 24(11):1800-1808 (2002).
Goodman and Gilman's The Pharmacological Basis of Therapeutics (Tenth Edition) (2001), McGraw Hill, Chapter 1, pp. 3-29.
United States Pharmacopeia (http://en.wikipedia.org/wiki/United_States Pharmacopeia# Product_quality.E2.80.93standards_and_verification) assessed from the internet on Oct. 22, 2012.
Berger et al., "Effects of adjuvant therapy with 0.1% olopatadine hydrochloride ophthalmic solution on quality of life in patients with allergic rhinitis using systemic or nasal therapy", *Ann. Allergy Asthma Immunol.*, 95(4):361-371 (2005).
Lanier et al., Comparison of the Efficacy of Combined Fluticasone Propionate and Olopatadine Versus Combined Fluticasone Propionate and Fexofenadine for the treatment of Allergic Rhinoconjunctivitis Induced by Conjunctival Allergen Challenge, *Clin. Ther.*, 24(7):1161-1174 (2002).
Ousler et al., "An evaluation of the ocular drying effects of 2 systemic antihistamines: loratadine and cetirizine hydrochloride", *Ann. Allergy Asthma Immunol.*, 93(5):460-464 (2004).
Spangler et al., "Randomized, Double-Masked Comparison of Olopatadine Ophthalmic Solution, Mometasone Furoate Monohydrate Nasal Spray, and Fexofenadine Hydrochloride Tablets Using the Conjunctival and Nasal Allergen Challenge Models", *Clin. Ther.*, 25(8):2245-2267 (2003).

* cited by examiner

*Primary Examiner* — Zohreh Fay
(74) *Attorney, Agent, or Firm* — Cooley LLP; Cynthia A. Kozakiewicz; Ivor R. Elrifi

(57) ABSTRACT

The present invention provides stable topical formulations of cetirizine that provide a comfortable formulation when instilled in the eye and is effective in the treatment of allergic conjunctivitis and/or allergic conjunctivitis. The invention further provides methods of treating allergic conjunctivitis and/or allergic rhinoconjunctivitis in a subject in need of such treatment by topical application of the cetirizine formulations of the invention directly to the eye.

3 Claims, 31 Drawing Sheets

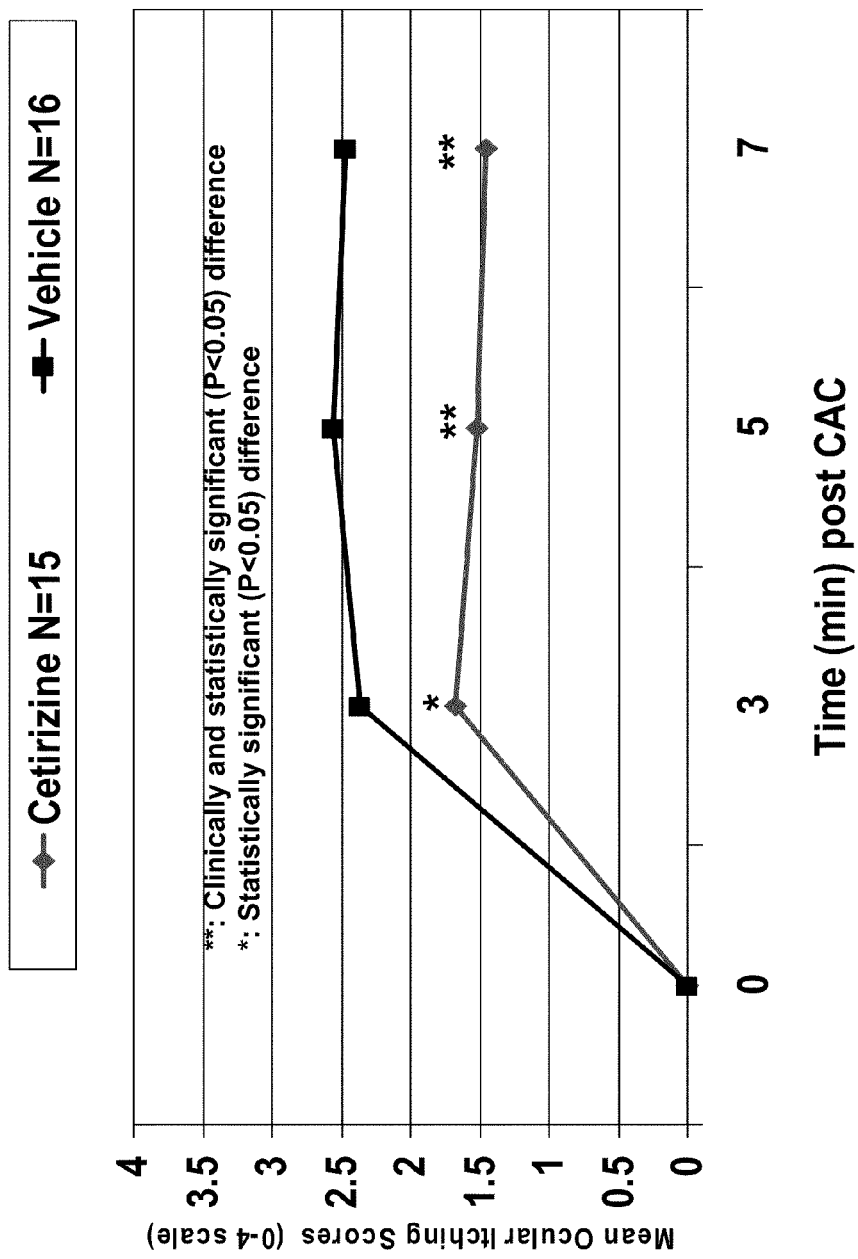
Figure 1A: Allergy Human POC Study #1 Results (Ocular Itching 16 Hours Post-Dose)

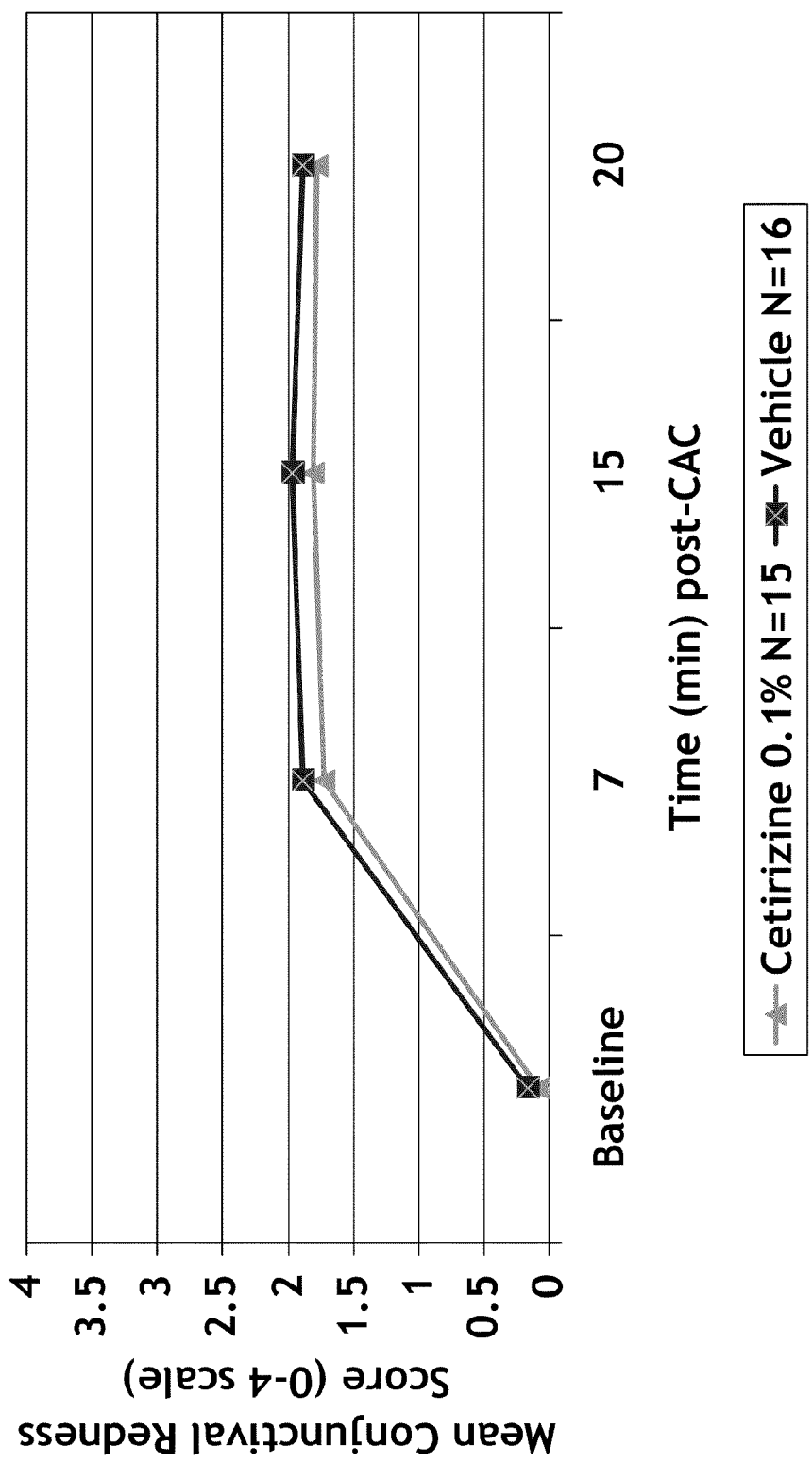

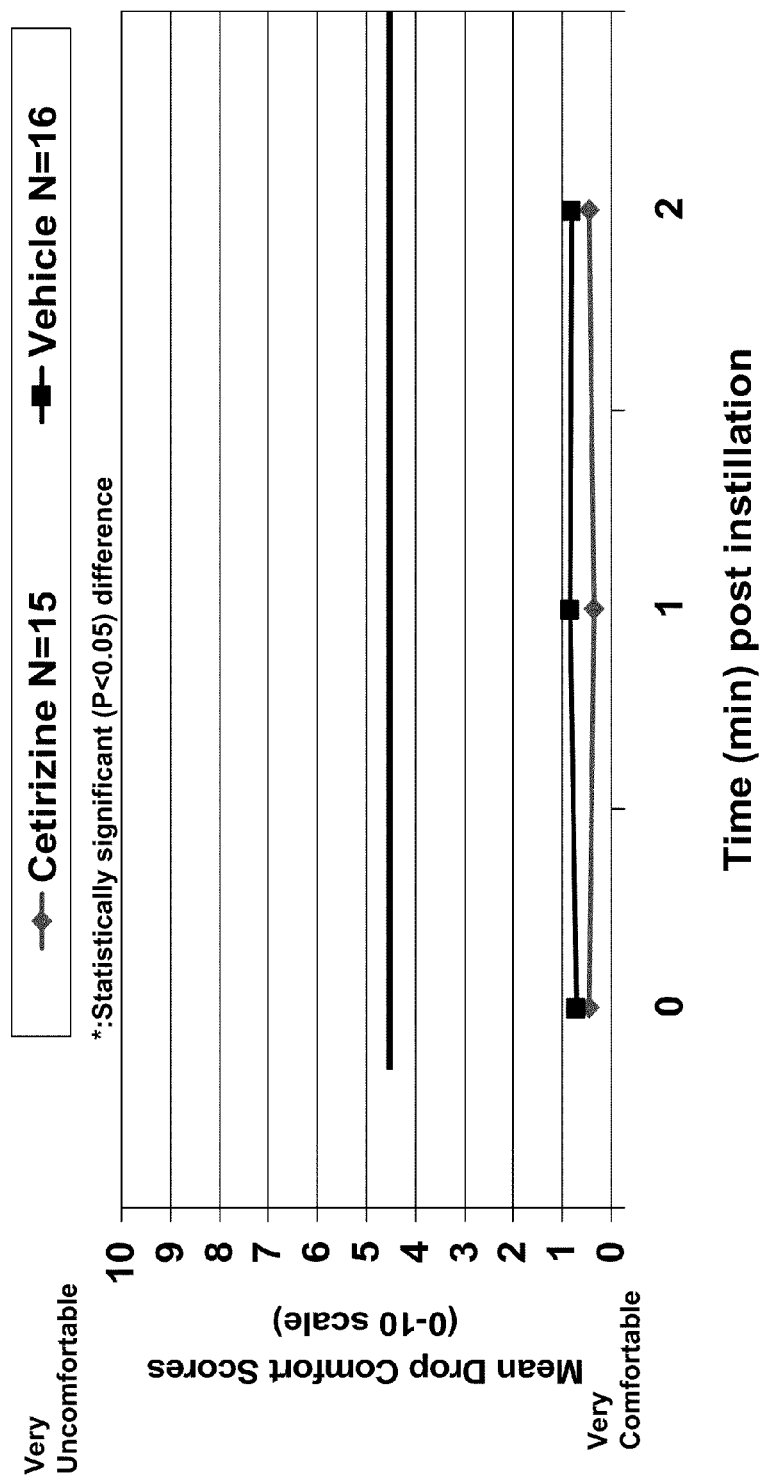
Figure 2: Allergy Human POC Study #1 Results (Drop Comfort)

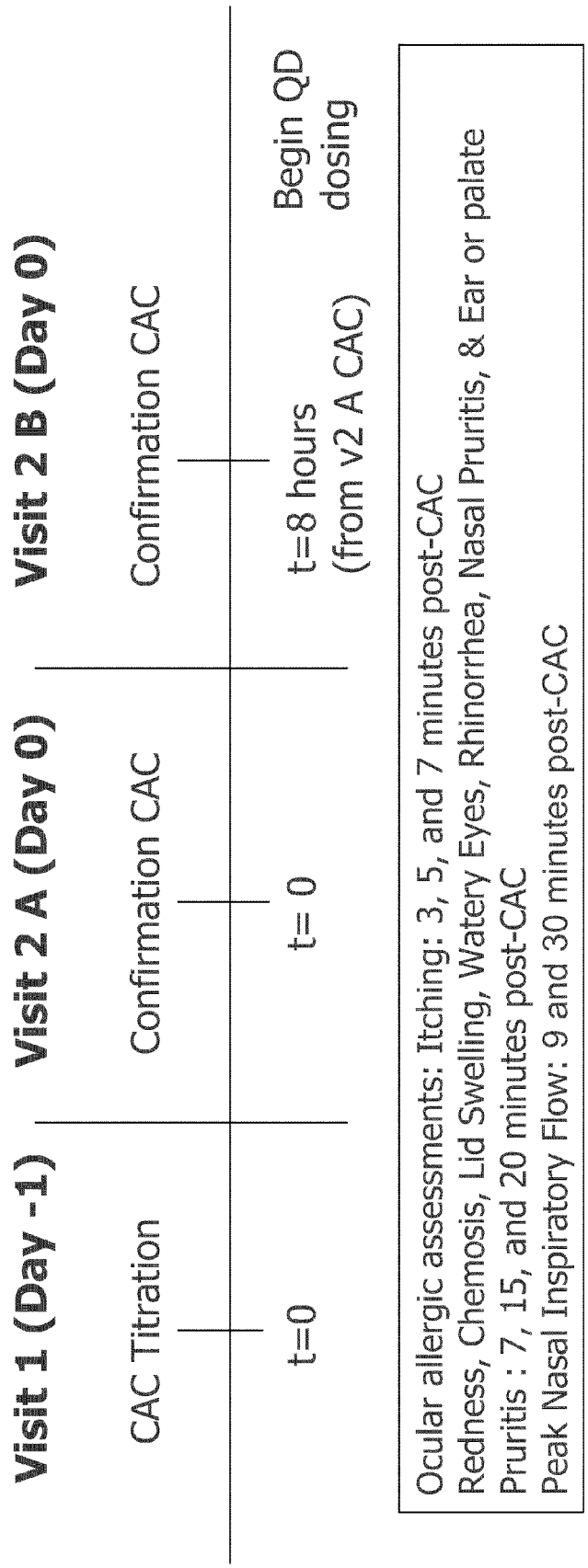
Figure 3A: Study Design: Screening

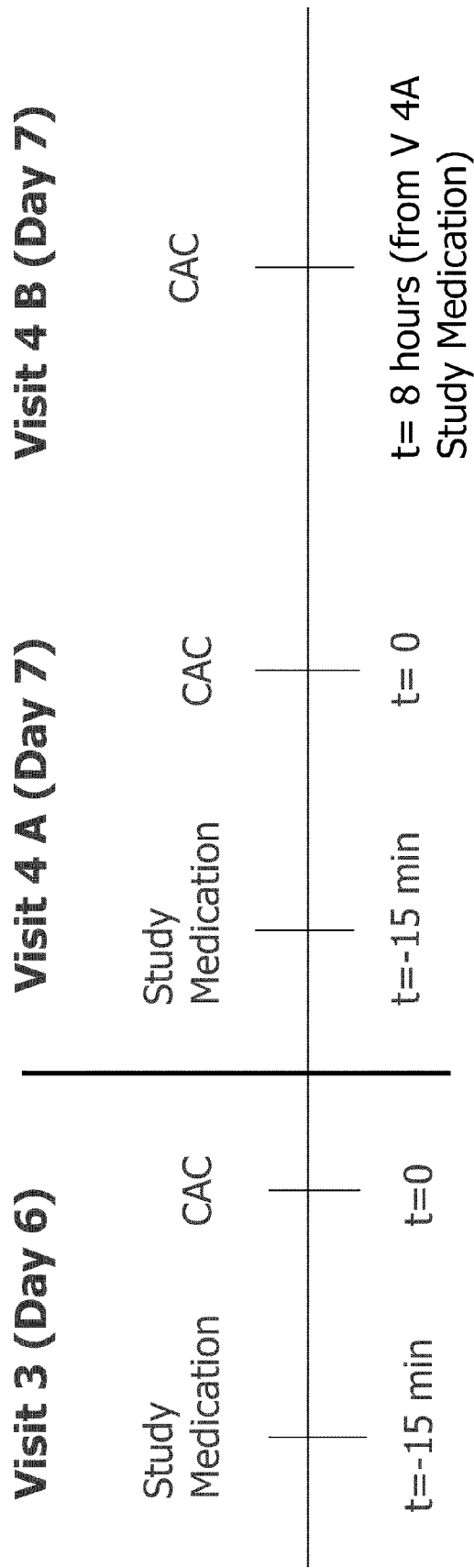
Figure 3B: Study Design: Efficacy Evaluation

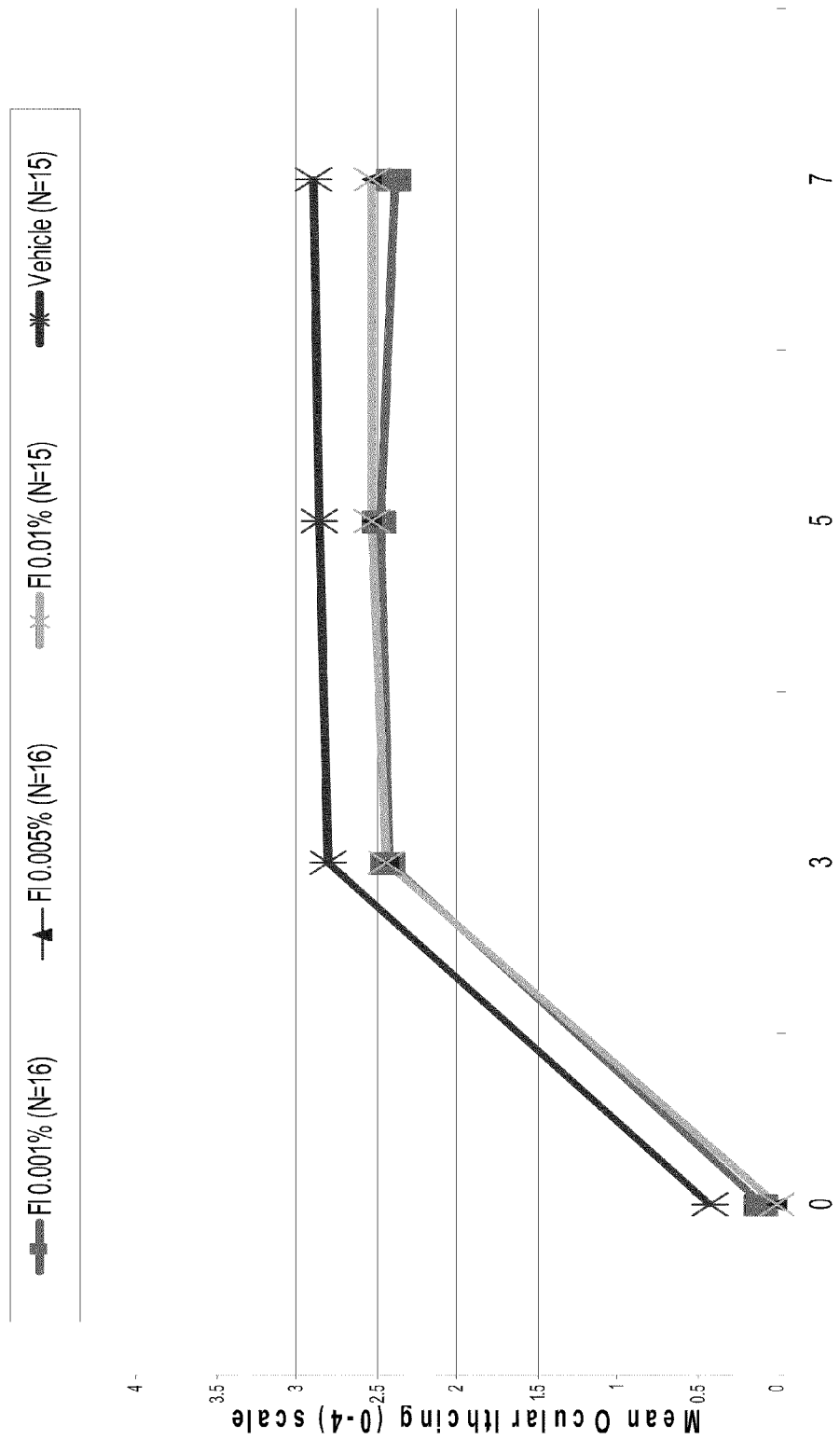
Figure 4: Primary: Ocular Itching (Visit 4B)

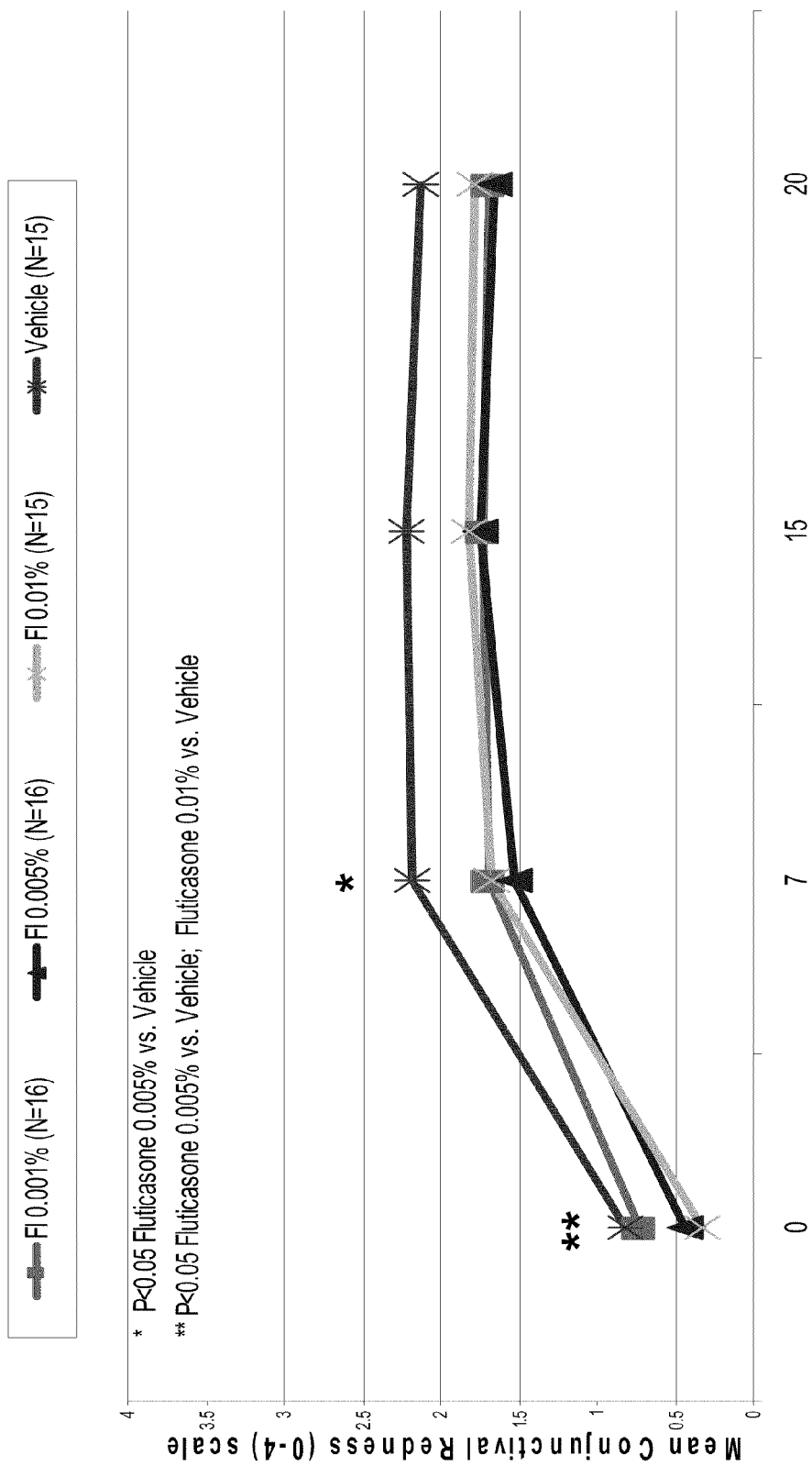

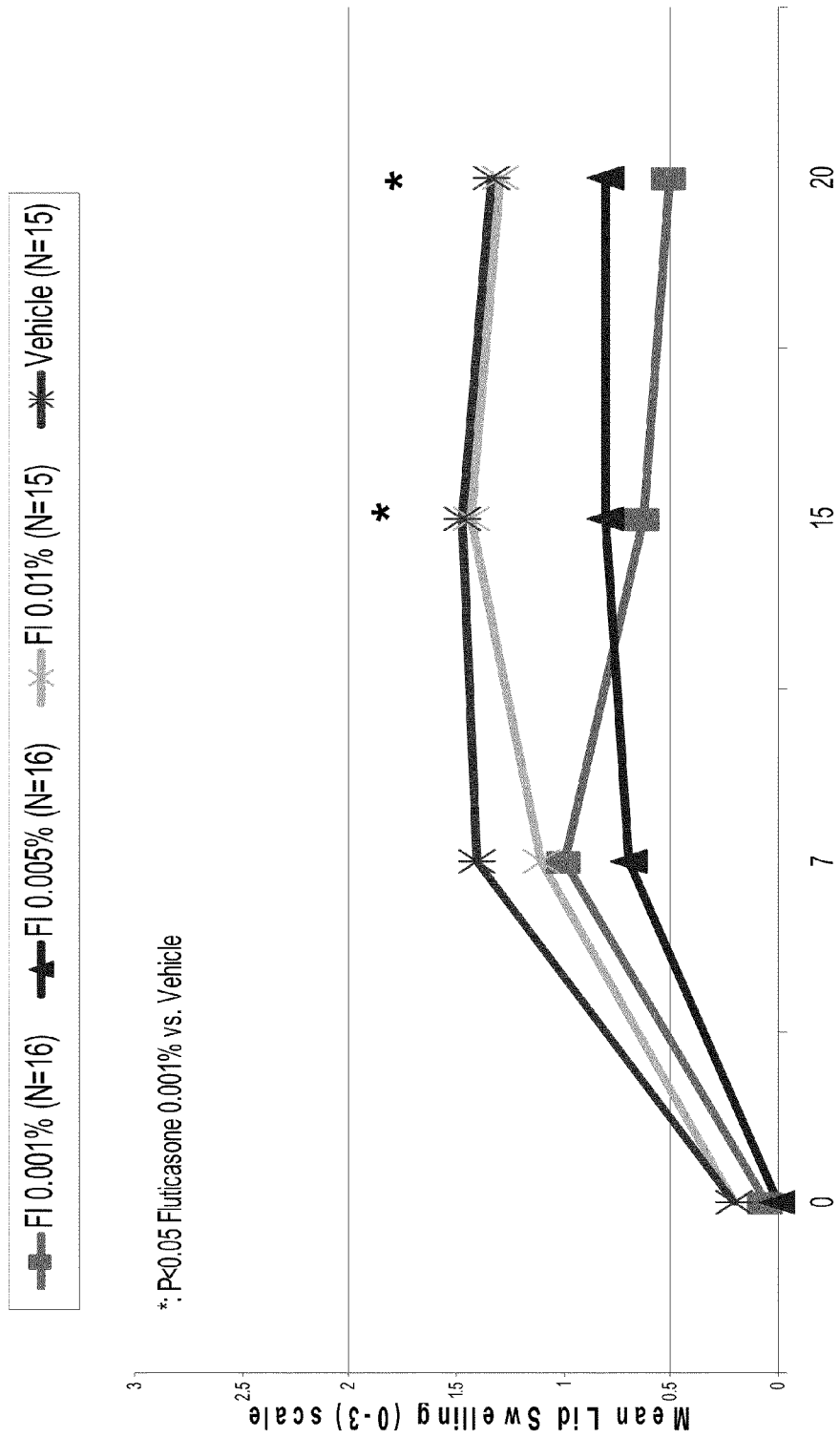

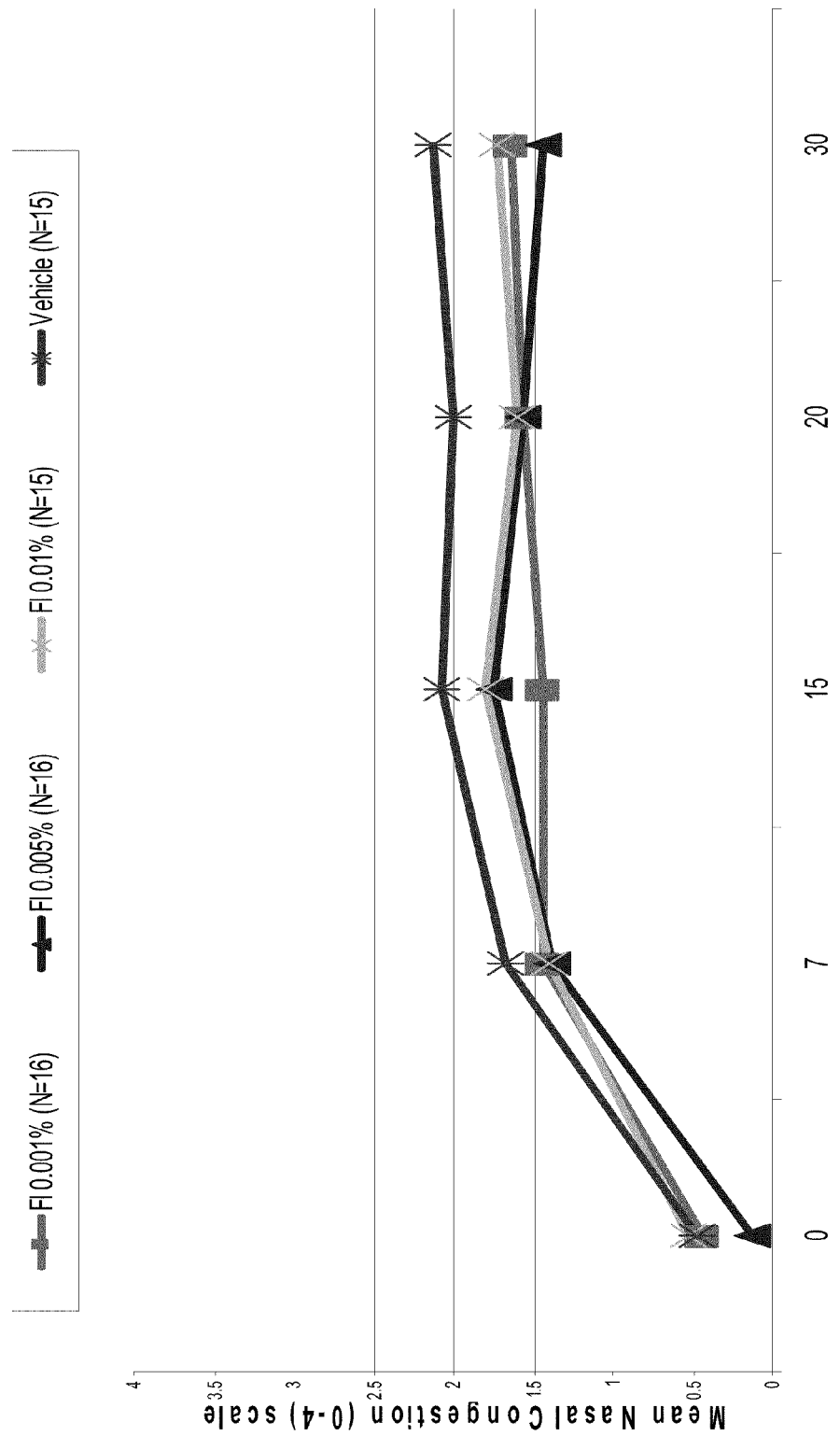

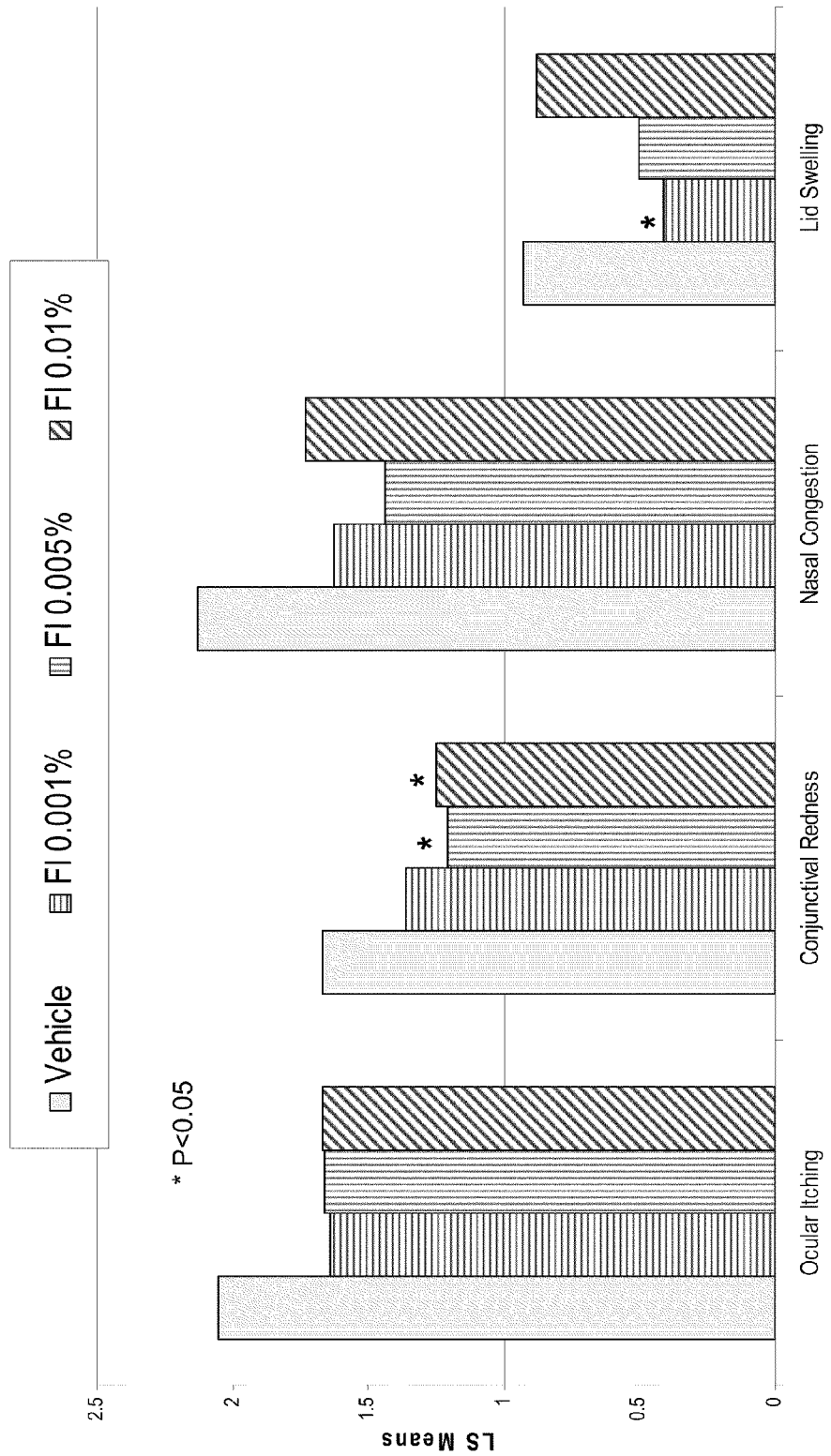

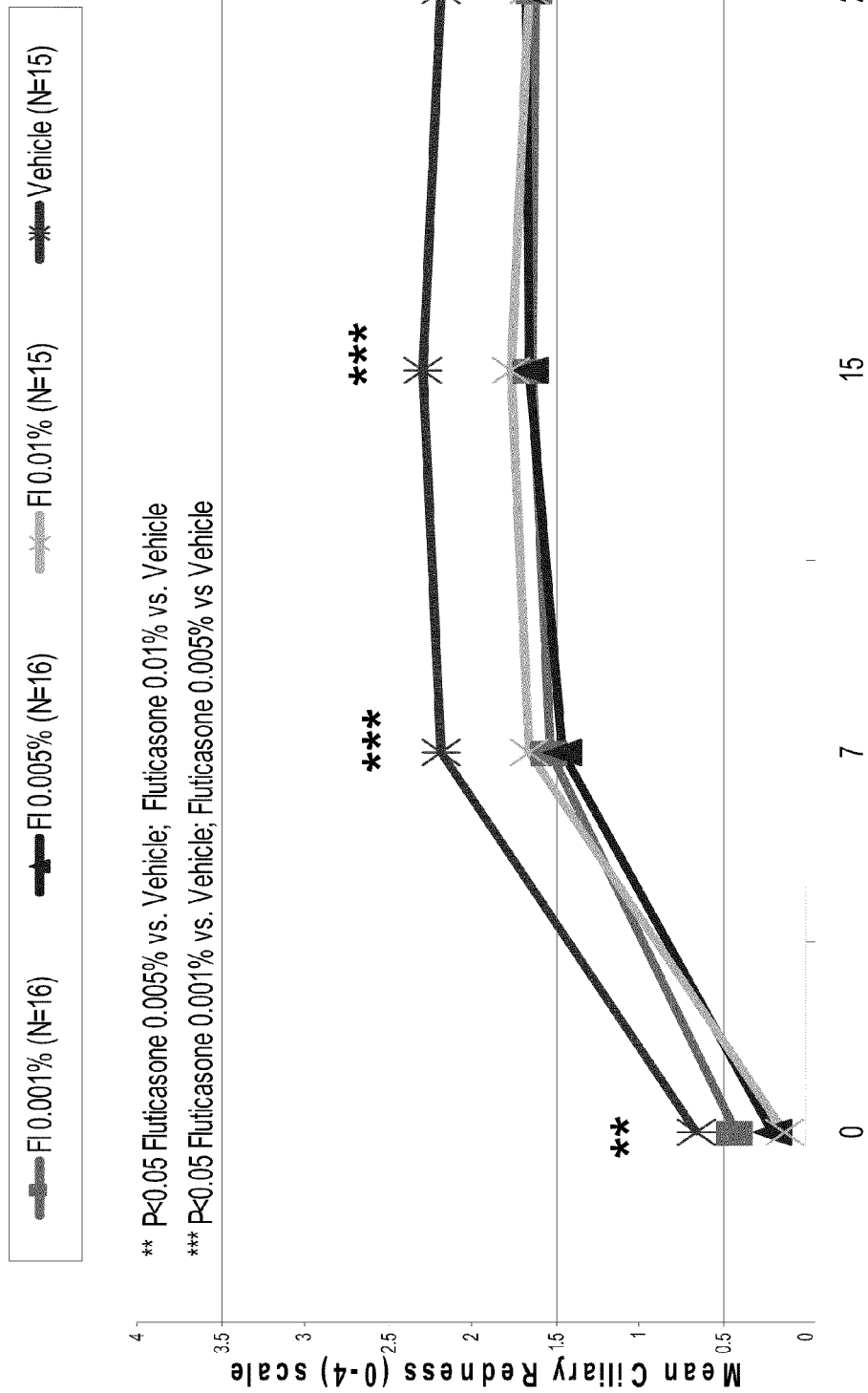

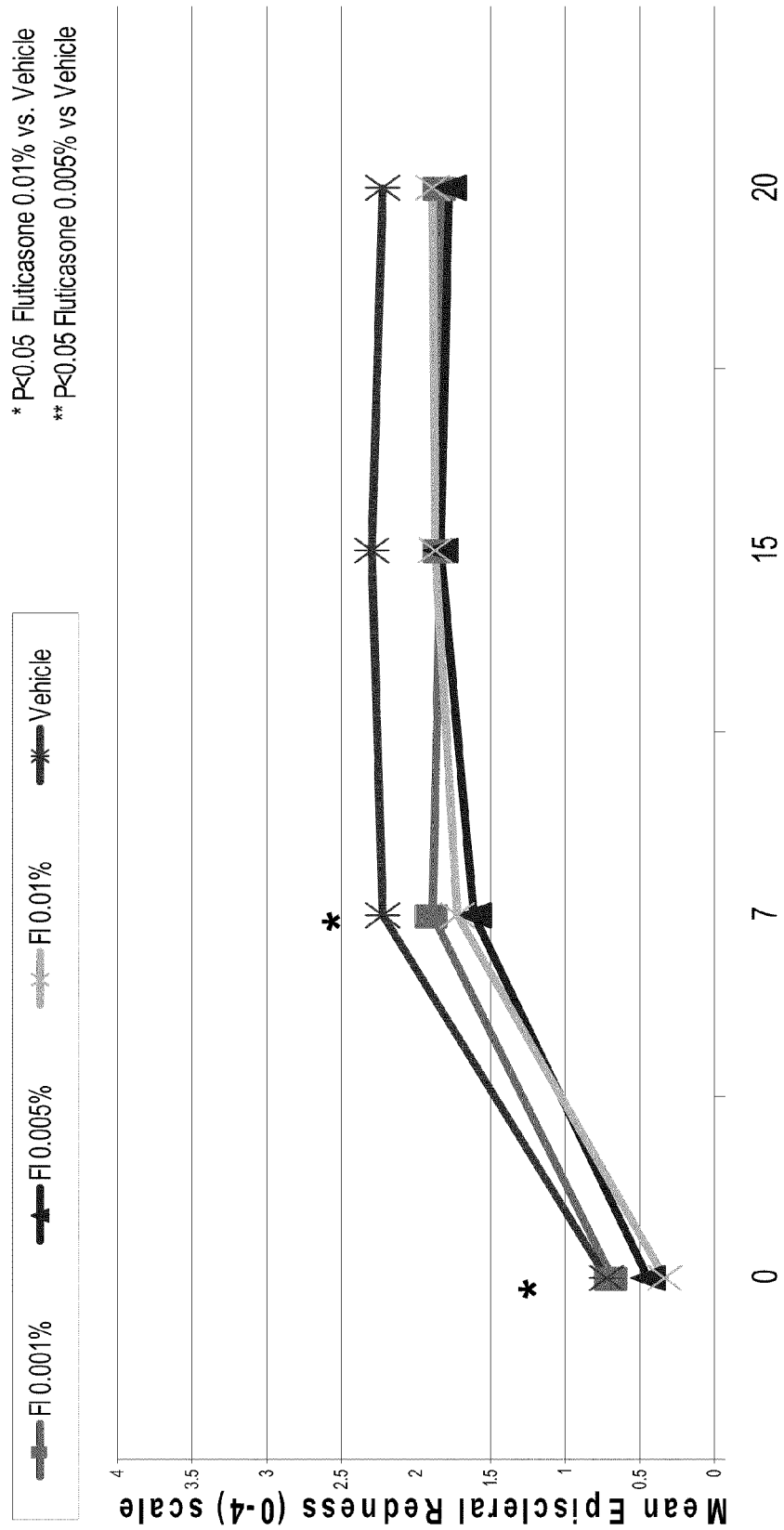

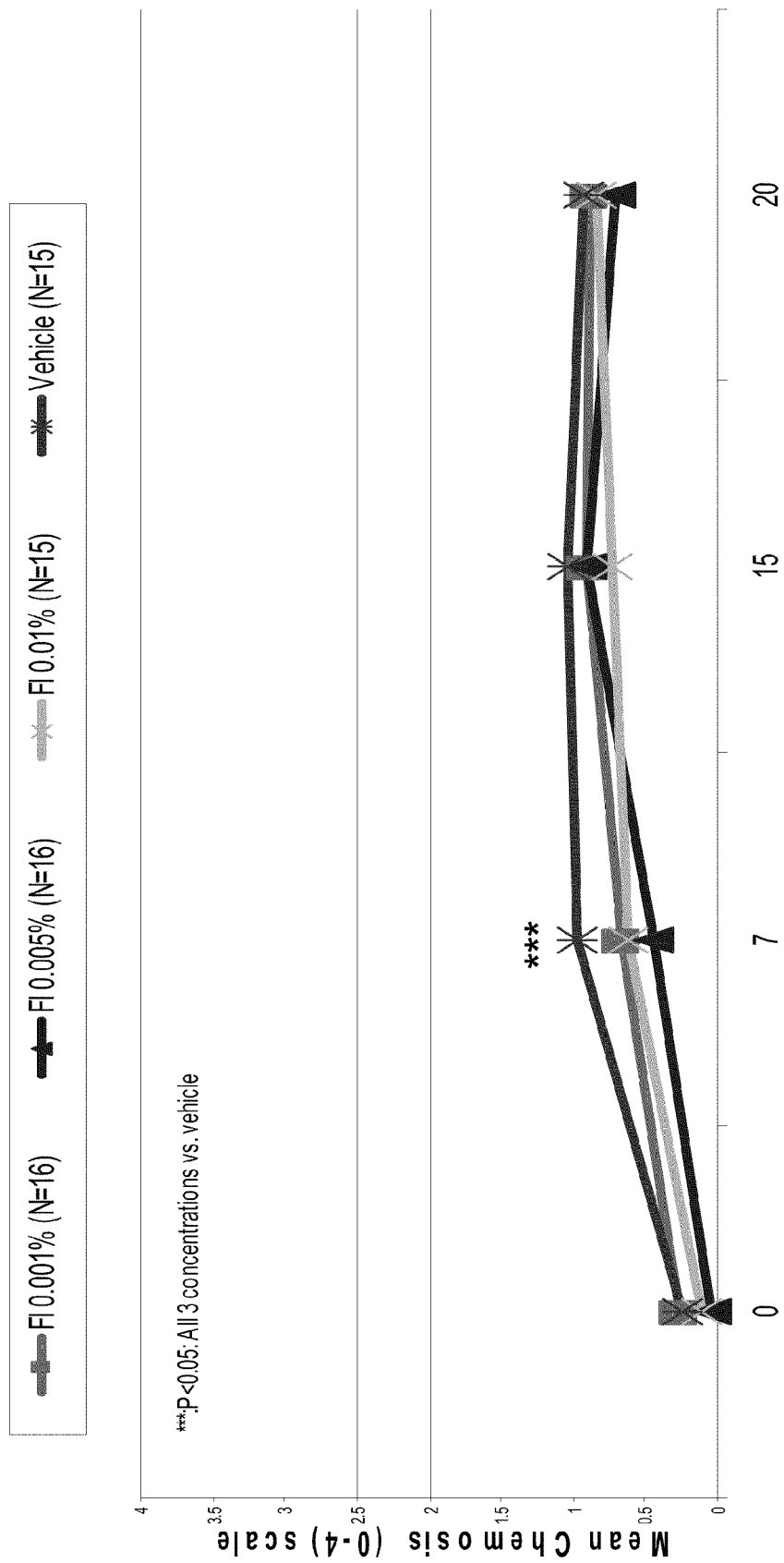
Figure 11: Secondary: Chemosis (Visit 4B)

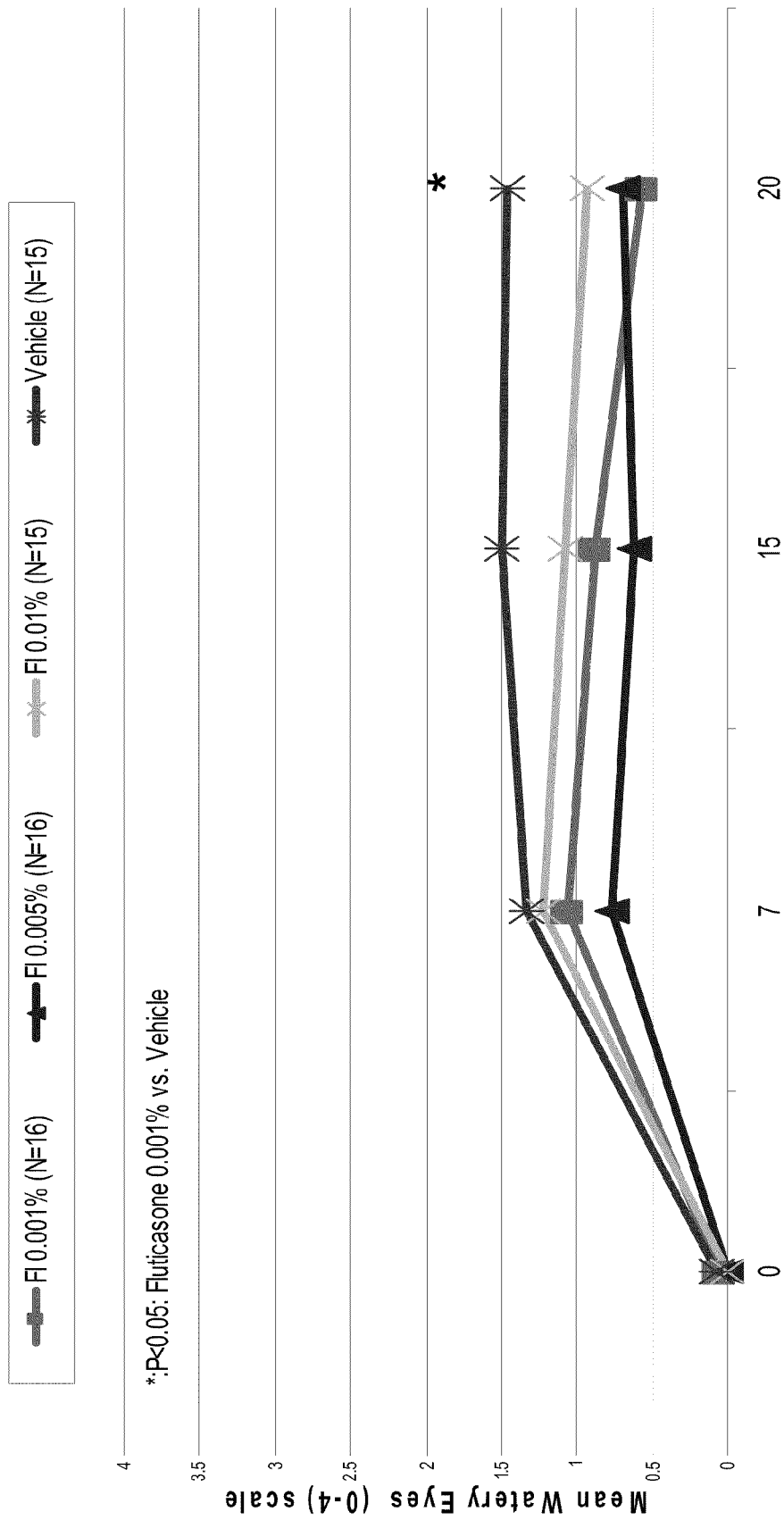

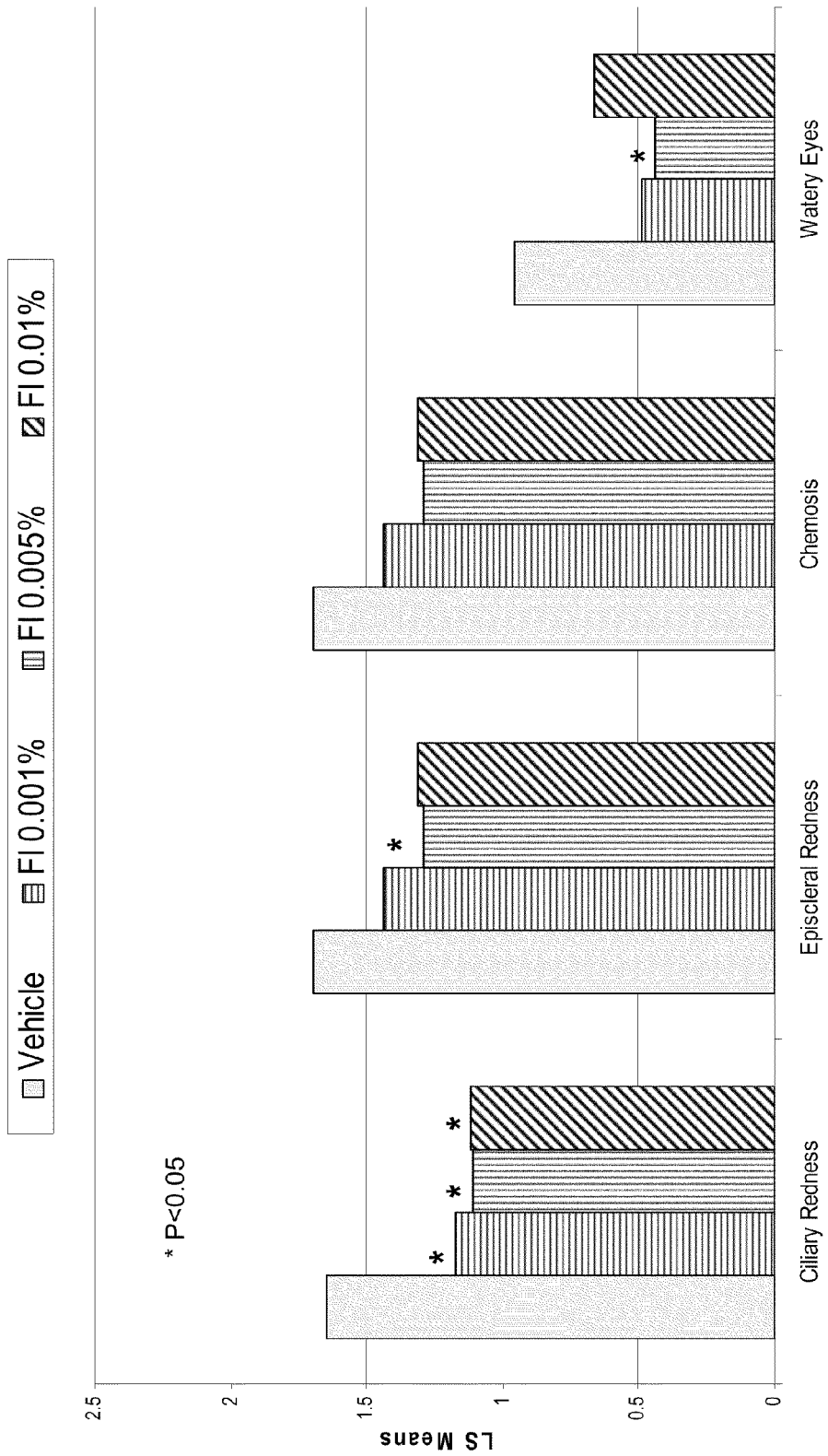

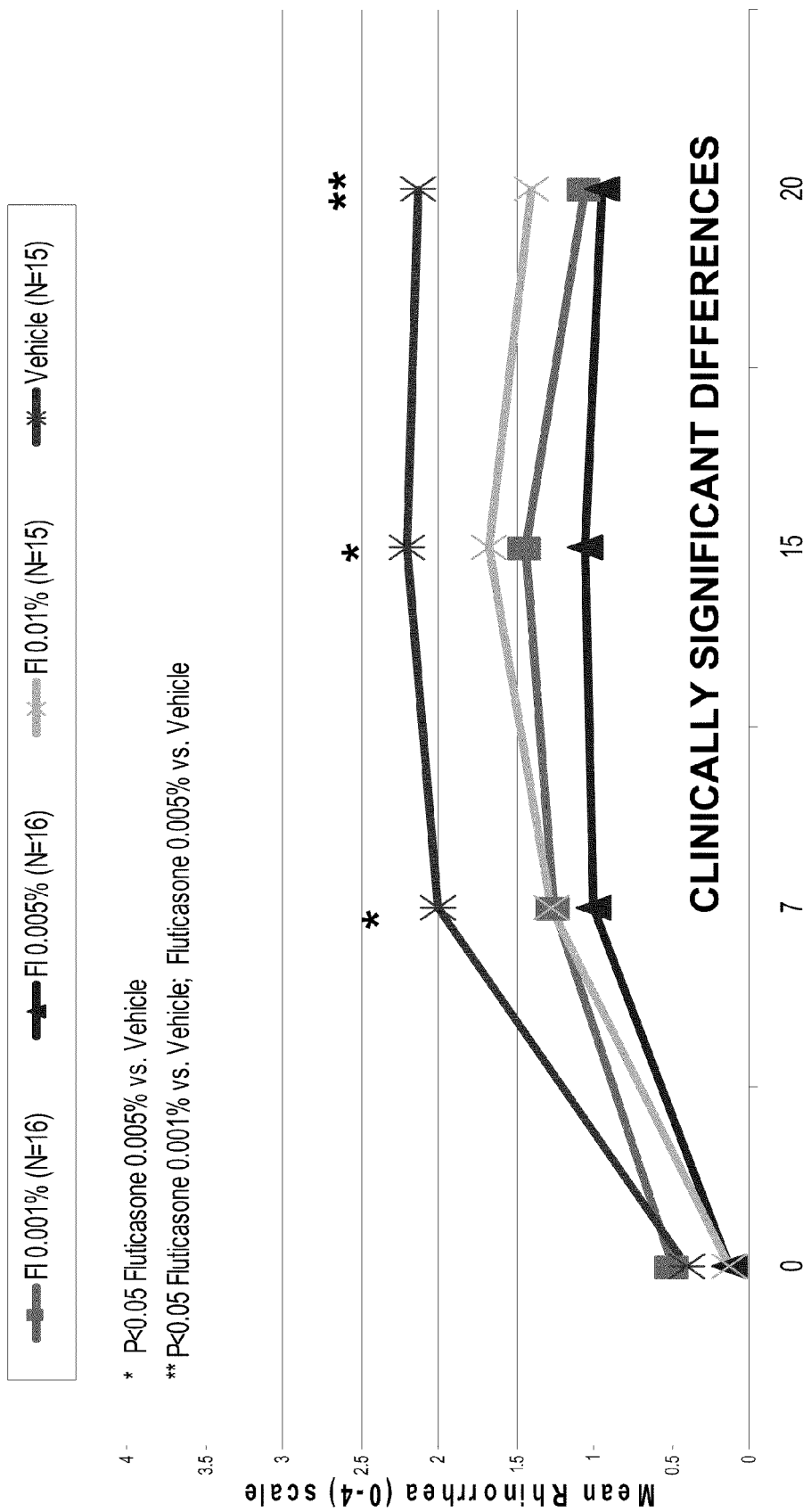

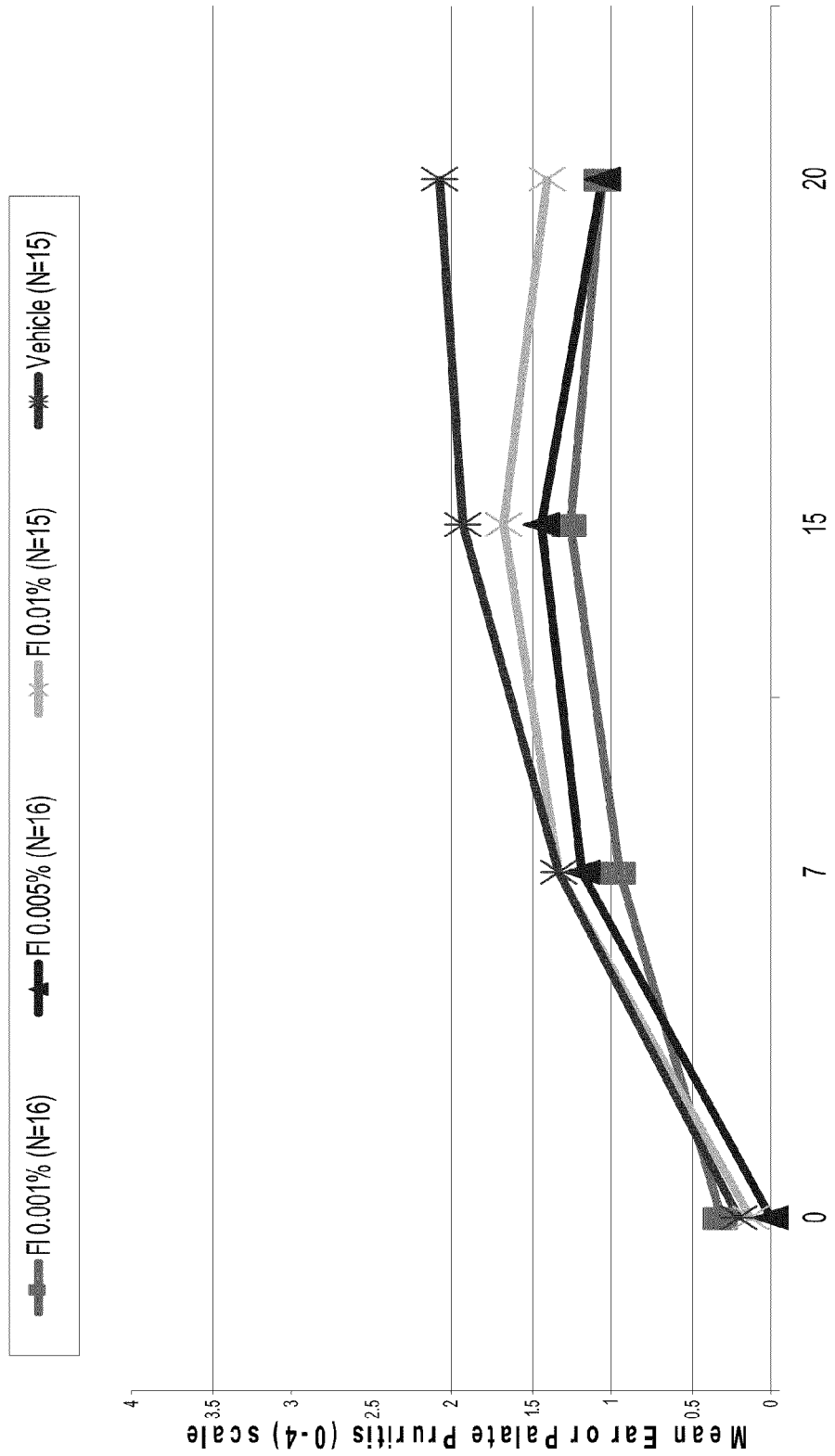

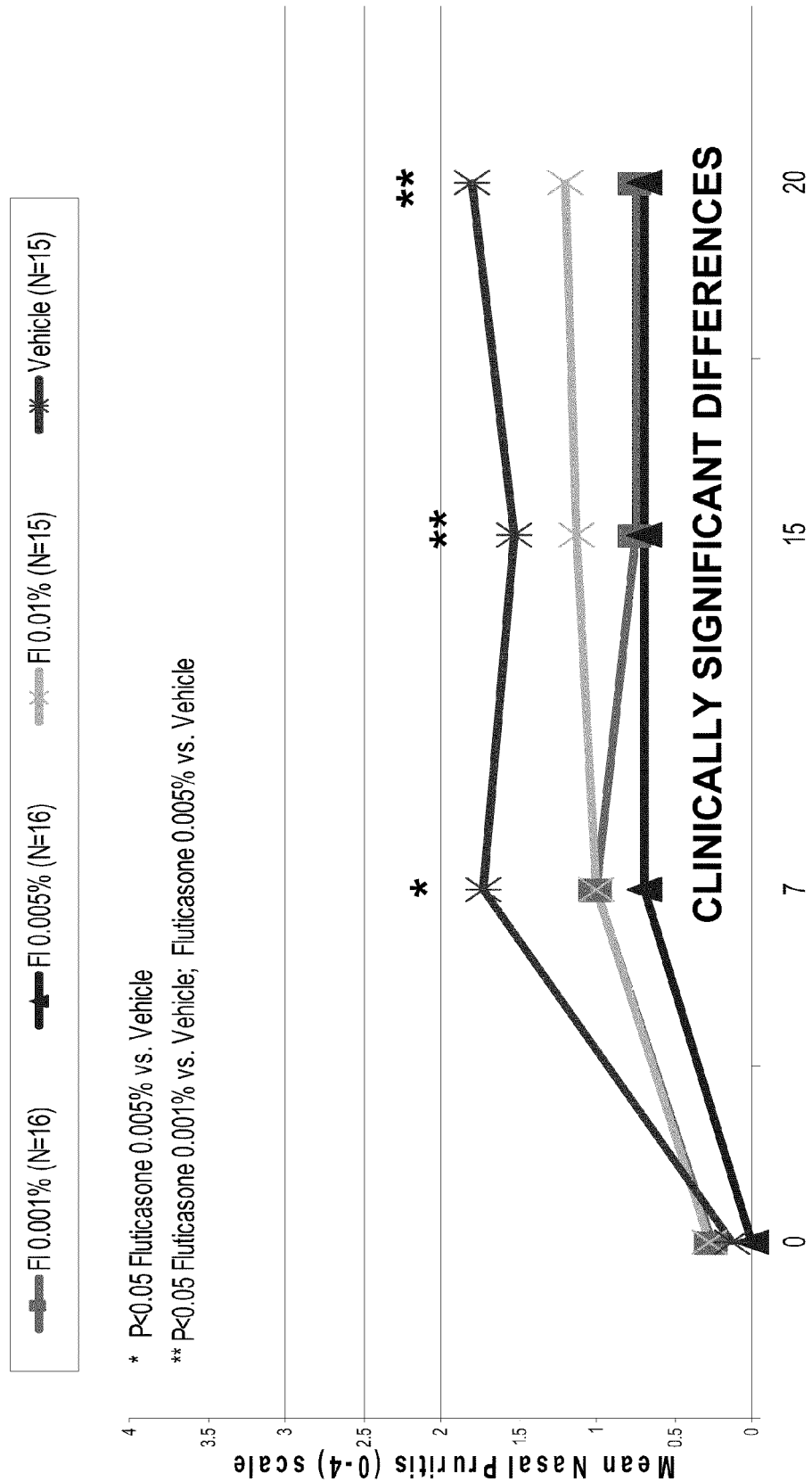

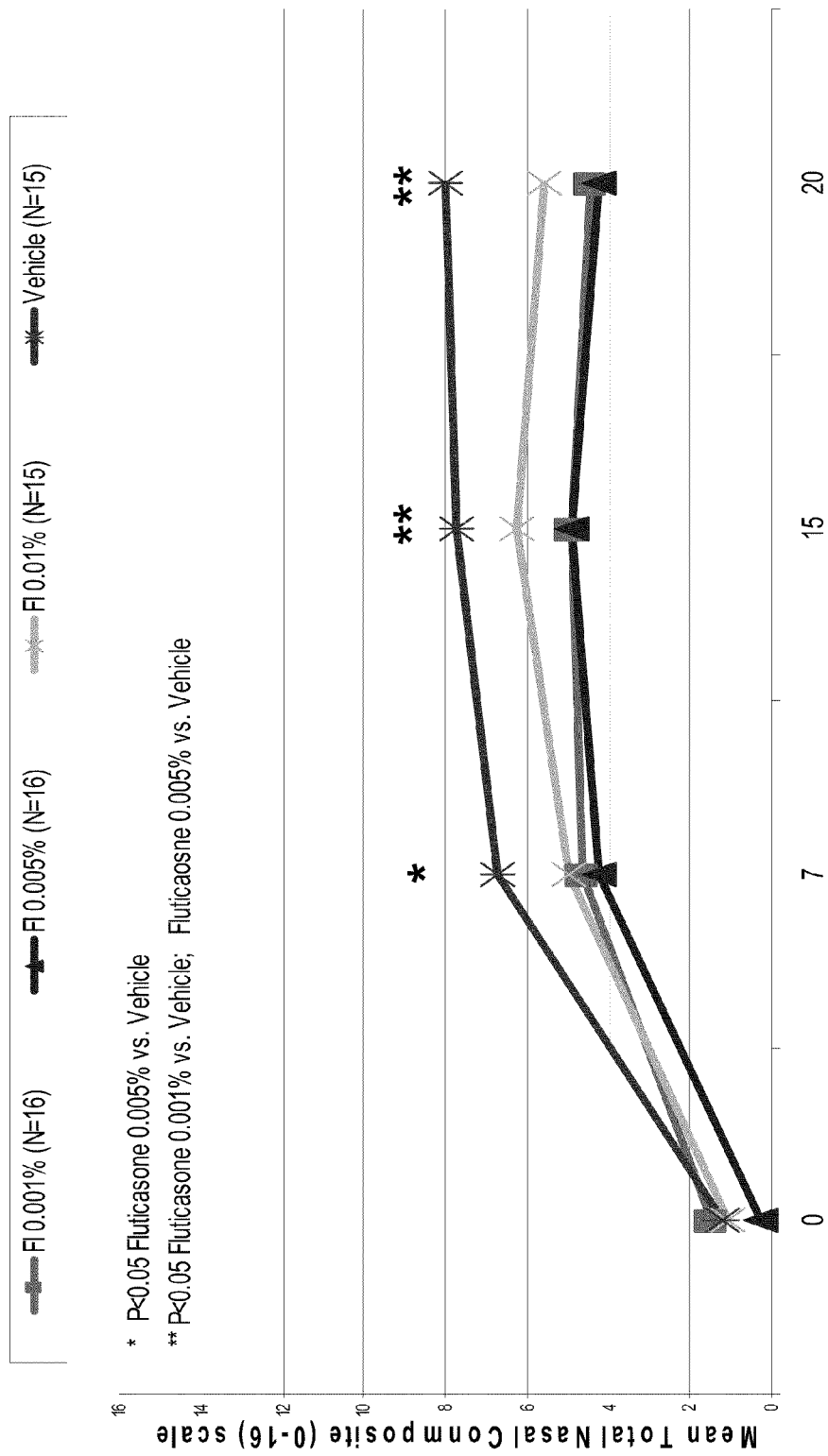

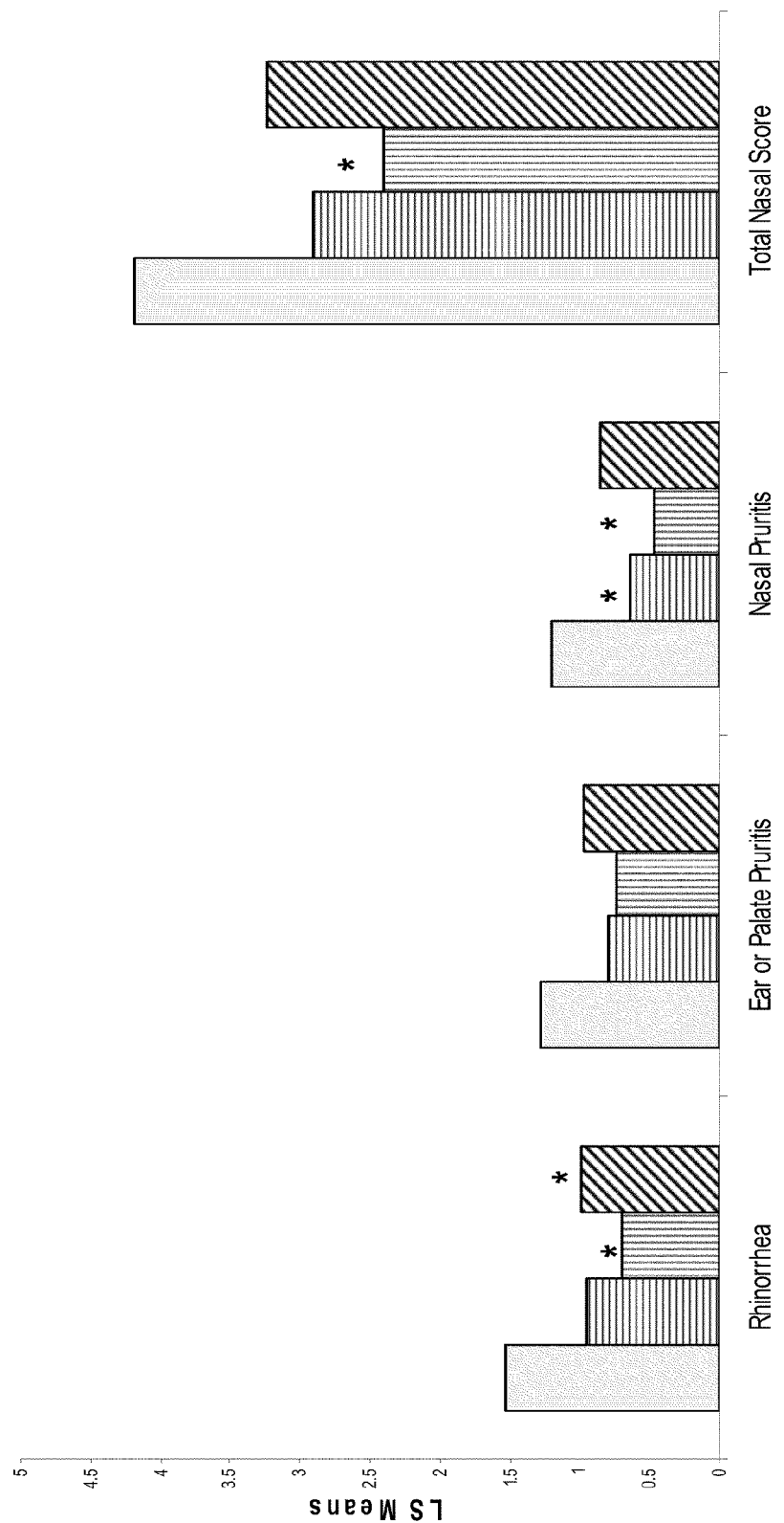

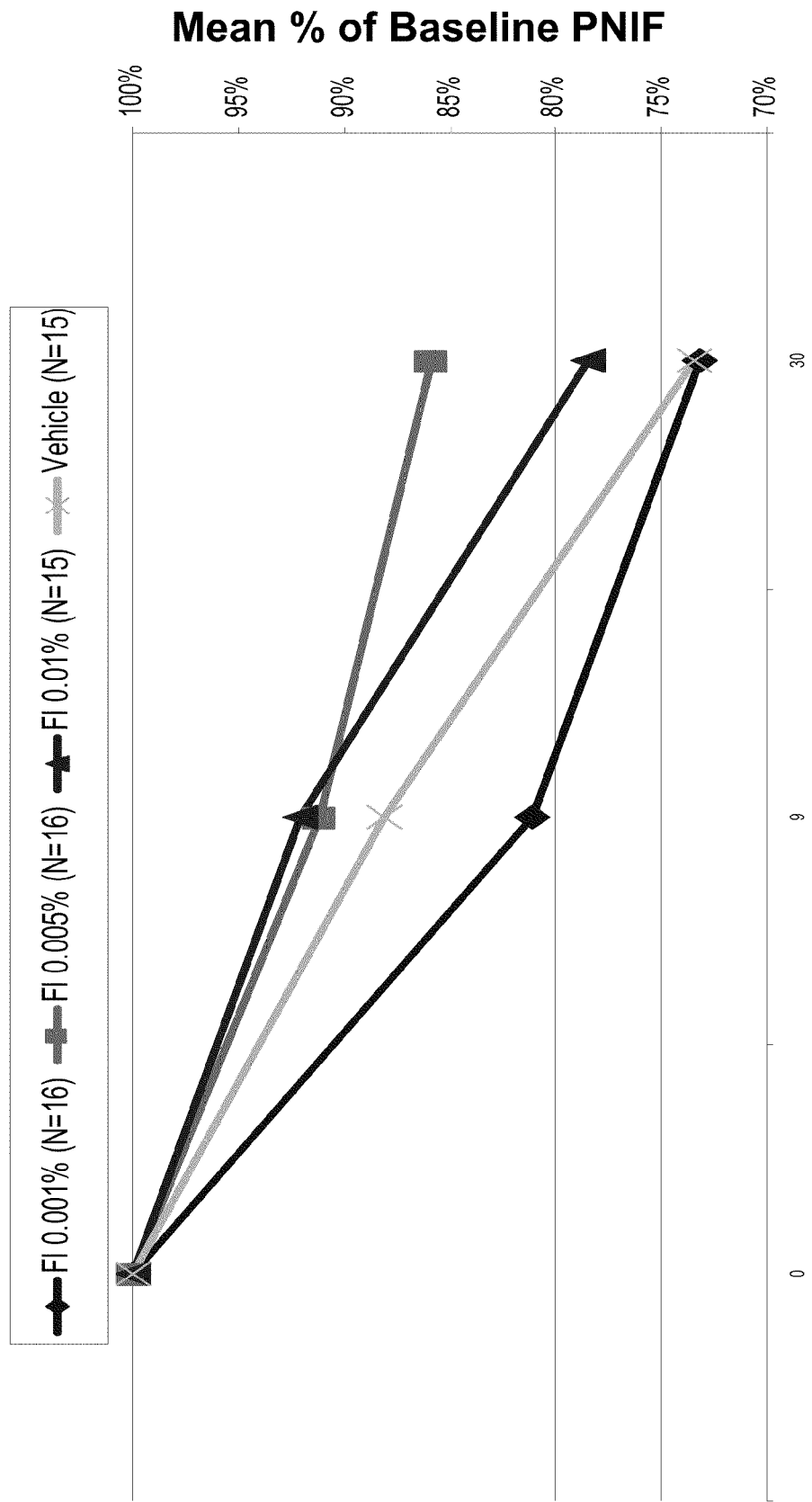
Figure 19: Secondary: PNIF Visit 4B

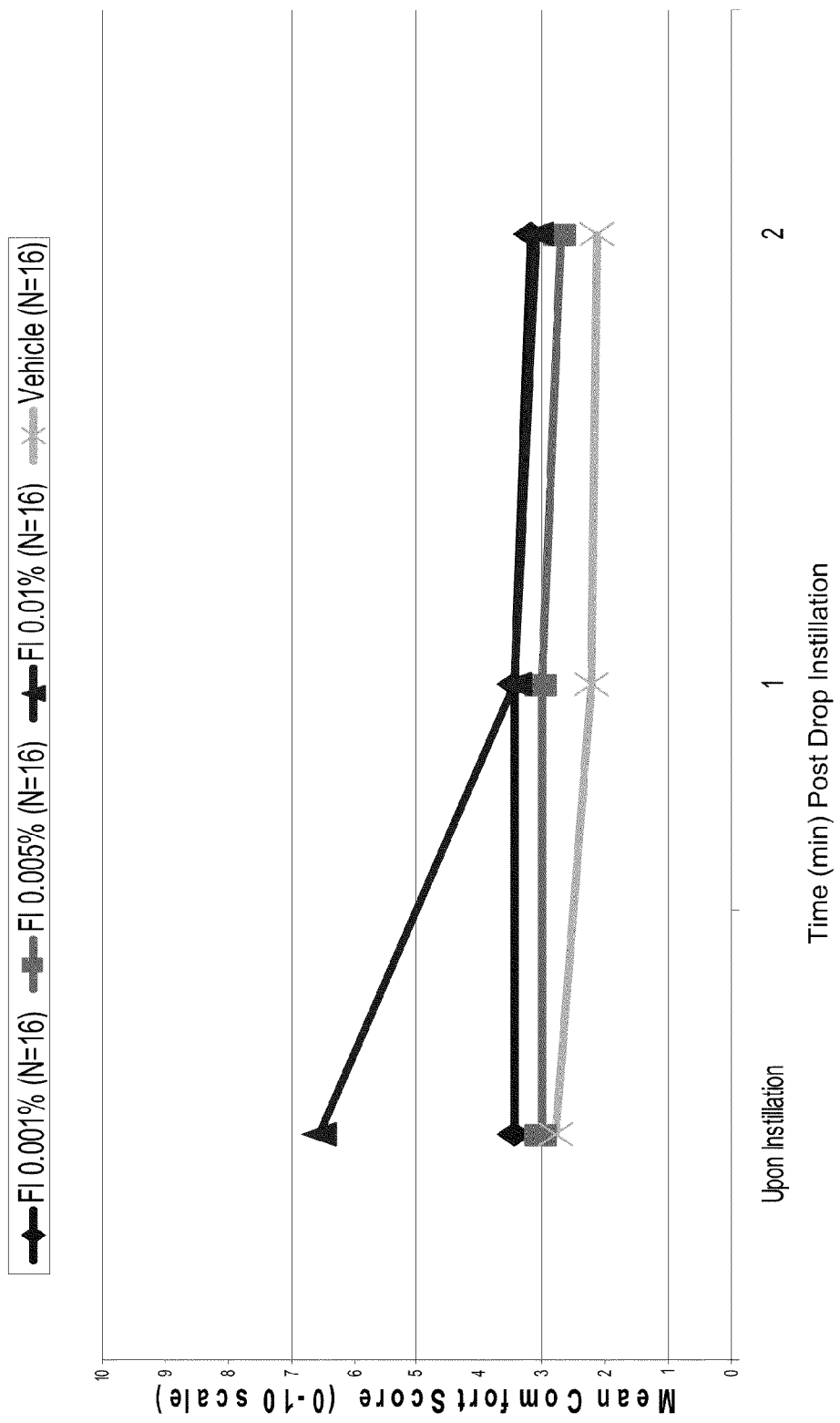
Figure 20: Visit 2 Drop Comfort Score

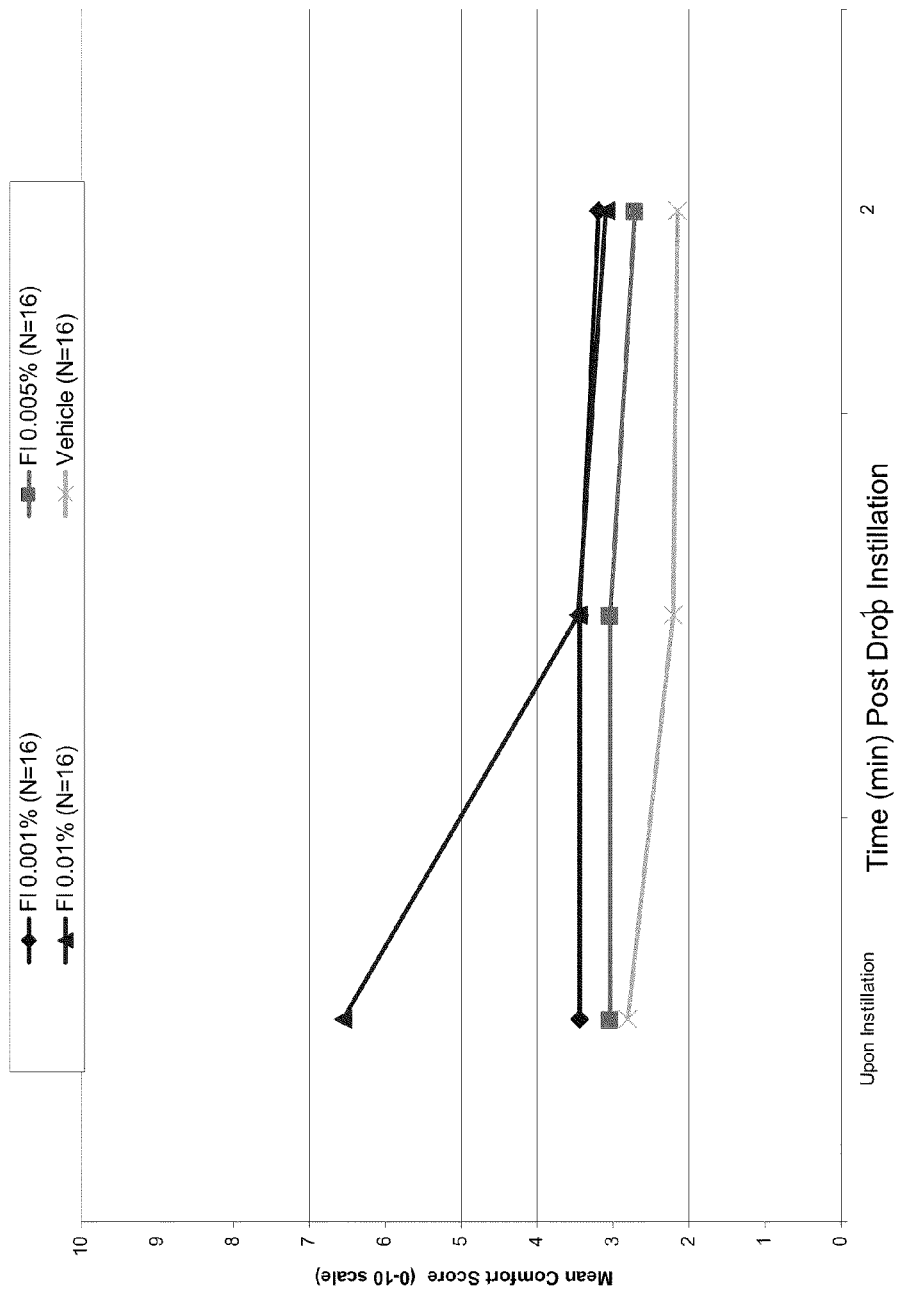

Figure 22: SAFETY- ADVERSE EVENTS

- Fluticasone 0.001%- 1 Event- 6.3% of Subjects
  - Vision blurred

- Fluticasone 0.005%- 2 Events- 12.5% of Subjects
  - Conjunctival hemorrhage
  - Dry eye

- Fluticasone 0.01%- 5 Events- 18.8% of Subjects
  - 3 Instillation site pain
  - 1 Instillation site irritation
  - 1 Headache

- Vehicle- 1 Event- 6.3% of Subjects
  - 1 Gastroenteritis Viral

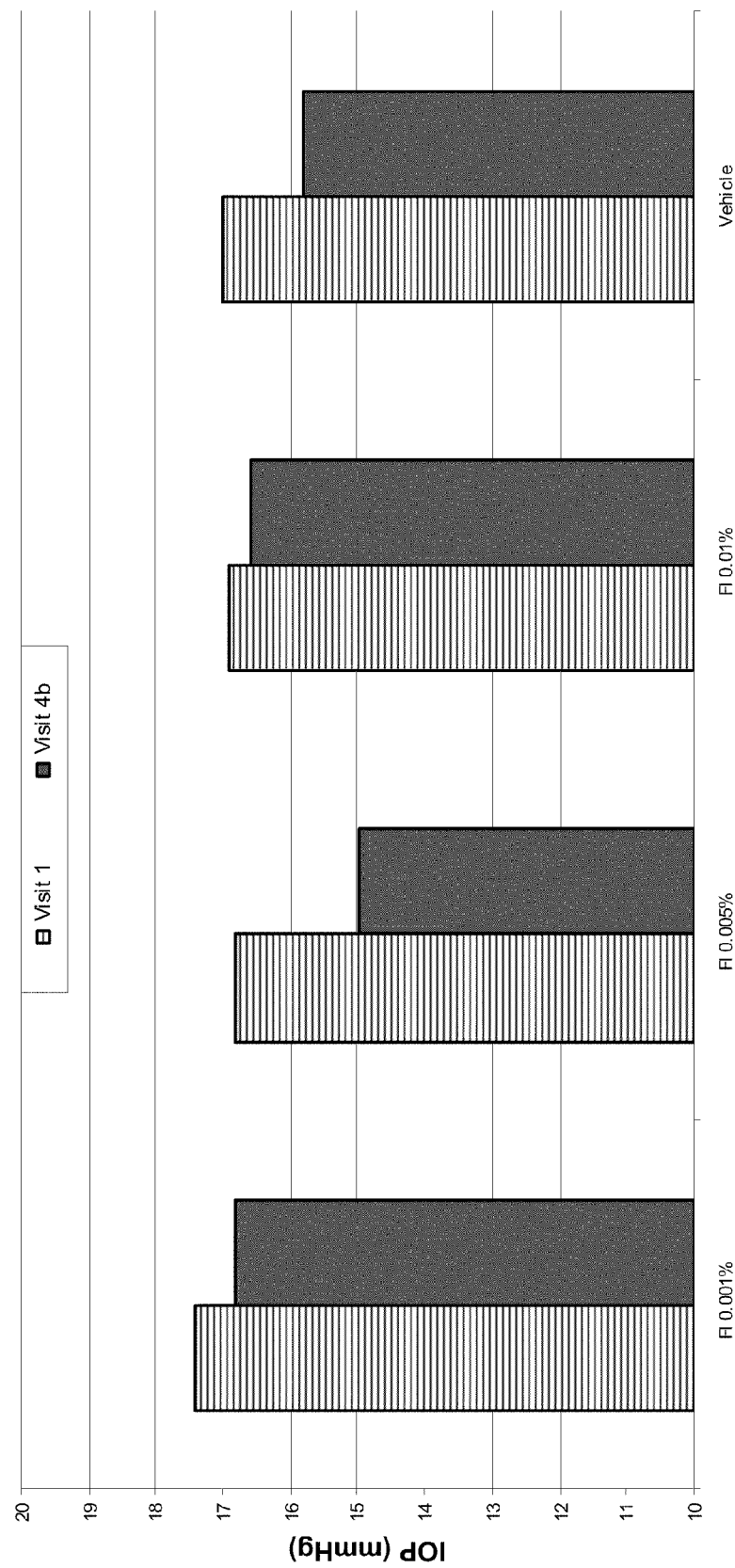

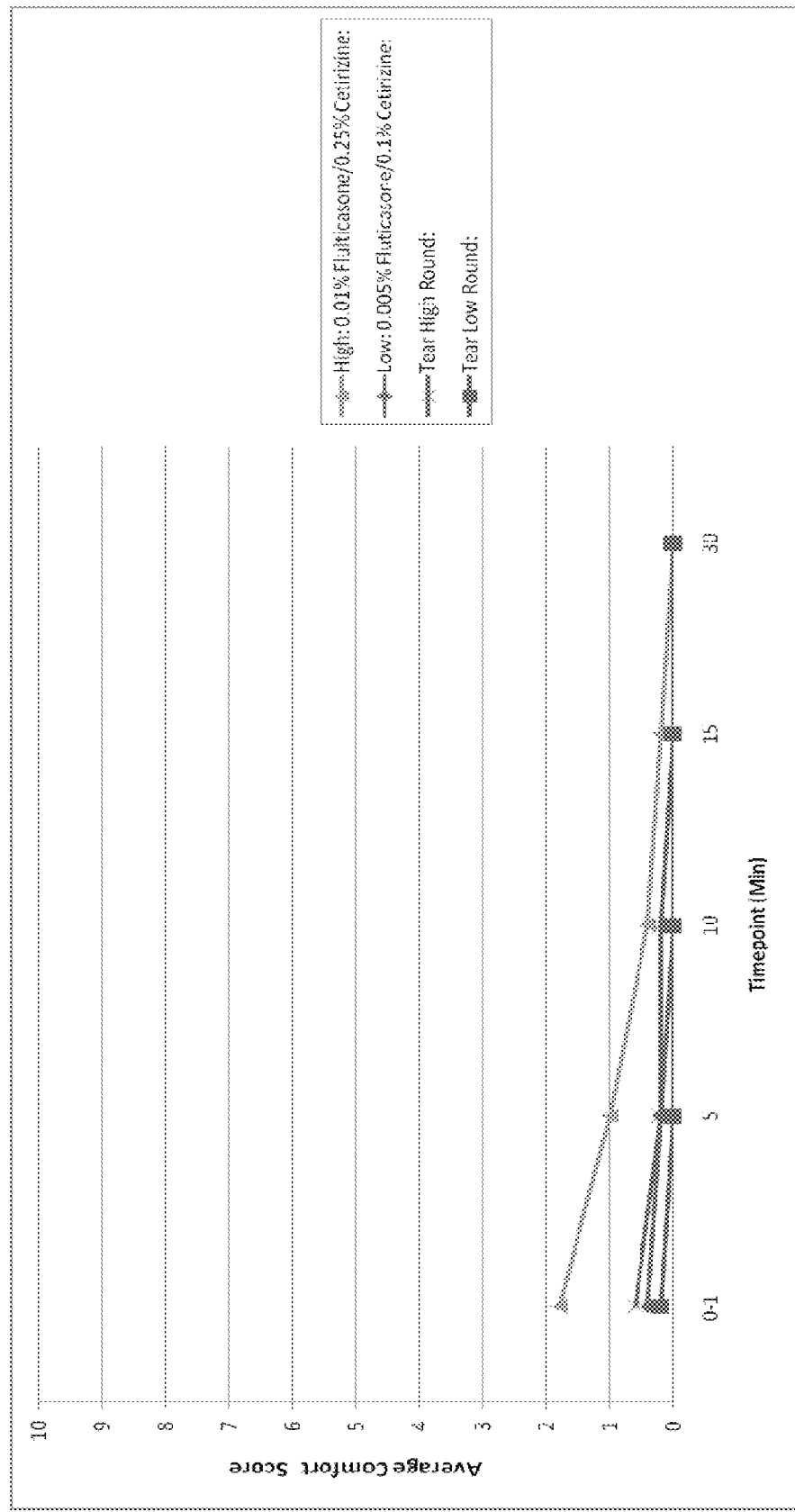
Figure 29: Cetirizine/Fluticasone: Comfort Assessment

OPHTHALMIC FORMULATIONS OF CETIRIZINE AND METHODS OF USE

REFERENCE TO RELATED APPLICATIONS

This application claims priority to U.S. Provisional Application No. 61/161,006, filed Mar. 17, 2009 and U.S. Provisional Application No. 61/174,850, filed May 1, 2009, the contents of which are each hereby incorporated by reference in their entireties.

FIELD OF THE INVENTION

The invention relates to compositions comprising cetirizine, alone or in combination with one or more additional active agents such as a steroid and/or a vasoconstrictor, and methods for using the same for treating allergic conjunctivitis and allergic rhinoconjunctivitis.

BACKGROUND OF THE INVENTION

There exists a need for topical ophthalmic pharmaceutical products to effectively treat allergic conjunctivitis, a disorder that presents with both acute allergic symptoms (i.e., seasonal allergy) and late phase inflammatory reactions (i.e., chronic, refractory or persistent allergy), as well as allergic rhinoconjunctivitis. It has been estimated that 46% (~70 million) of the adult allergy patients in the United States suffer from both the acute and late phase conditions of allergic conjunctivitis, whereas only 19% suffer from only acute or late phase allergy, respectively. It is estimated that allergic rhinoconjunctivitis (a combination of ocular and nasal symptoms) may occur in up to 90% of patients with allergies. The average age of allergy sufferers—between 20 and 40 years—coincides with the average age of the work force and the most productive period of an individual's life.

Both seasonal and perennial allergic conjunctivitis (ocular allergies) are characterized by itchy, red, swollen, and watery eyes. Allergic rhinitis (nasal allergies) manifests as a runny nose, sneezing, congestion, and similar symptoms. It can be difficult for a physician to distinguish allergic conjunctivitis from allergic rhinoconjunctivitis because both allergic reactions can occur simultaneously or be triggered by the same types of stimuli. It is further difficult to distinguish acute allergic symptoms from late phase symptoms of allergic conjunctivitis, as each of these conditions can persist simultaneously or morph back and forth in any given individual. The signs and symptoms of allergic conjunctivitis and allergic rhinoconjunctivitis can significantly impact the quality of life of patients, from social interactions, productivity at work and school, to the ability to perform visual tasks such as working on a computer or reading.

Acute symptoms of allergic conjunctivitis are characterized by the clinical signs and symptoms of eye itching, redness, and swelling. Late phase or allergic inflammation reactions of allergic conjunctivitis include redness, lid swelling and tearing, and in some cases itching, as well as the predominance of congestion in the nose. Acute allergic symptoms are predominantly caused by the activation of mast cells, which when stimulated by an allergen (pollen, dust, dander) releases a host of substances that produce the signs and symptoms of allergic conjunctivitis (itching, redness, swelling, and tearing). Histamine is the primary mediator released and stimulates receptors on nerve endings and blood vessels to produce itching and redness. There are two histamine receptors that have been identified on the ocular surface. H1 receptors on nerve endings lead to itching, and H1 and H2 receptors on blood vessels lead to dilation of the blood vessels, leading to redness, and leakage of fluid from the vessels into the surrounding tissue producing swelling. Late phase inflammatory reactions are mediated by activation of inflammatory cells.

Like allergic conjunctivitis, allergic rhinoconjunctivitis is an allergen-induced, mast cell-mediated response. The reaction is triggered when airborne allergens bind to antibodies attached to the surface of mast cells in the eye and/or nose. Mast cells, in turn, release chemical mediators, which account for the immediate reaction in sensitized individuals exposed to allergen. Some of these mediators, such as histamine, directly affect blood vessels and nerves, leading to the signs and symptoms of allergic disease. Other released mediators cause the influx of white blood cells to the site, which leads to sustained symptoms in severe cases and particularly congestion in the nose.

Allergic conjunctivitis and rhinoconjunctivitis may also co-exist with other external ocular conditions and diseases, such as dry eye, or irritations caused by pollutants or other causes. This leads to a compromised tear film, which serves to protect the ocular surface from allergens.

Currently available treatments for eye allergy include: drops which can wash allergens off the ocular surface and act as a barrier for the eye (e.g. artificial tears), drugs which block histamine from binding to the histamine receptors (e.g. antihistamines), drugs that block the release of histamine and other substances from the mast cell (e.g. mast cell stabilizers), drugs with multiple modes of action (e.g. antihistamine/mast cell stabilizing agents), and drugs that can actively constrict blood vessels thus reducing redness and swelling (e.g. vasoconstrictors). The criteria which may be considered in evaluating the appropriateness of an agent for a patient include: efficacy at onset of action, duration of action, how well it controls the individual signs and symptoms of allergic conjunctivitis, comfort of the formulation when instilled in the eye, and safety of the formulation when instilled in the eye. The comfort of an ophthalmic product depends on the active pharmaceutical ingredient itself, as well as the nature of the formulation and the vehicle that makes up the product. Oral antihistamines have been shown to induce decreased tear production and lead to dryness of the ocular surface, which can exacerbate ocular discomfort and can make the eye susceptible to irritation by an ophthalmic product.

The currently available treatments which contain a single active agent, such as an antihistamine or a mast cell stabilizer, typically provide relief for only acute allergic conjunctivitis and don't address the signs and symptoms of the late phase inflammatory reactions (i.e., chronic, refractory, or persistent allergy).

Currently available treatments for allergic rhinoconjunctivitis include eyedrops, nasal sprays, and systemic oral agents. Currently approved anti-allergy eyedrops are indicated for ocular allergy and nasal sprays are targeted for nasal allergy. Systemic agents, while they have indications to treat both nasal and ocular symptoms, several well controlled clinical trials conducted to ophthalmic standards have shown that systemic antihistamines are inferior to eyedrops in treating the ocular signs and symptoms (Spangler et al., Clin. Ther. 25(8), 2245-2267 (2003), are not in fact clinically effective on eye allergy, and actually have been shown by objective measures to reduce tear production on the eye by 50%, causing ocular dryness (Ousler et al, Ann Allergy Asthma Immunol. November; 93(5):460-4 (2004)). Further studies have shown that the combination of an eyedrop and nasal steroid is more effective than a systemic agent in treating the ocular and nasal signs and symptoms of allergy (Lanier et al. Clin. Ther. 24(7), 1161-1174 (2002)).

Cetirizine hydrochloride is a racemic selective H1 receptor inverse agonist which functions as an antihistamine. It is a major metabolite of hydroxyzine and a derivative of piperazine. The levorotary enantiomer of cetirizine is known as levocetirizine. Cetirizine hydrochloride is FDA approved for oral use and is used as a systemic antihistamine for the treatment of allergies, hay fever, angioedema, and urticaria. It has been historically difficult to prepare cetirizine as an ophthalmic solution with satisfactory safety and stability profiles. Cetirizine has the disadvantage of forming aggregates in solution at low concentrations (typically less than 1% (w/v)), thereby decreasing the stability as an aqueous solution. Moreover, higher concentrations of cetirizine (1% and above) are strongly irritating and thus unsuitable for direct ocular or nasal administration. U.S. Pat. No. 5,419,898 addresses these issues by using a cyclodextrin compound to increase the solubility and stability of cetirizine for ophthalmic use. However, a cyclodextrin-free stable ophthalmic formulation containing cetirizine as the only active ingredient that is both comfortable in the eye and effective to mitigate the symptoms of allergic conjunctivitis has never been previously achieved.

There thus exists a need to develop an effective, stable yet comfortable and safe cetirizine formulations for ophthalmic administration for the treatment of allergic conjunctivitis (i.e., the acute phase, the late inflammatory phase, or both) and allergic rhinoconjunctivitis. Such formulations for administration directly to the eye would be advantageous over systemic oral formulations and nasal sprays due to faster action and avoidance of the side effects associated with systemic administration.

SUMMARY OF THE INVENTION

The present invention provides comfortable topical ophthalmic formulations for the treatment of both acute and late phase signs of allergic conjunctivitis as well as rhinoconjunctivitis which contain a combination of ingredients which act synergistically to relieve the signs and symptoms of allergic conjunctivitis and/or rhinoconjunctivitis, particularly ocular itching and/or nasal symptoms (e.g., itchy, running nose, sneezing, nasal/sinus congestion). In particular, the formulations described herein provide stable formulations comprising a low concentration of cetirizine suitable for ophthalmic use in a comfortable ophthalmic formulation when instilled in the eye.

The present invention is based on the surprising discovery that stable topical ophthalmic formulations comprising a low concentration of cetirizine can be prepared without the use of a cyclodextrin or other solubilizer compound, that is both comfortable when instilled in the eye and effective to mitigate the symptoms of allergic conjunctivitis and/or rhinoconjunctivitis, particularly ocular itching and/or nasal symptoms (e.g., itchy, running nose, sneezing, nasal/sinus congestion). The invention also provides methods for the treatment of allergic conjunctivitis and/or rhinoconjunctivitis in a subject in need of such treatment by administering a cetirizine formulation of the invention directly to the eye of the subject. Surprisingly, once a day dosing of the low concentration cetirizine formulations of the invention is effective to mitigate the symptoms of allergic conjunctivitis and/or rhinoconjunctivitis, particularly ocular itching and/or nasal symptoms (e.g., itchy, running nose, sneezing, nasal/sinus congestion).

The invention also provides stable ophthalmic formulations of cetirizine in combination with one or more active ingredients including but not limited to a vasoconstrictor such as naphazoline or oxymetazoline, and/or a steroid such as fluticasone, or combinations thereof. The combination formulations of cetirizine are effective in mitigating the signs and symptoms of both acute and late phase allergic conjunctivitis, such as ocular itching, redness, chemosis, and lid swelling, and nasal symptoms, as well as allergic rhinoconjunctivitis.

More specifically, the combination formulations of the invention (e.g., cetirizine and fluticasone) provide a comprehensive treatment benefit for both acute and late phase reactions of allergic conjunctivitis, that cannot be achieved by the use of a single anti-allergic, or other active agent, alone. Antihistamines and mast cell stabilizers such as cetirizine do not effectively block all allergic and pro-inflammatory mediators from the mast cell. Cetirizine, and other antihistamines and mast cell stabilizers, effectively masks itching but has minimal effects on redness, tearing, swelling and inflammation. However, when cetirizine is combined with another active agent which can halt the transcription and production of inflammatory mediators and down-regulate the production of anti-inflammatory mediator, such as a steroid (e.g., fluticasone), treatment of the signs and symptoms of acute and late phase allergic conjunctivitis ((i.e., the aggregate disease) is achieved. Likewise, such combination formulations provide a comprehensive treatment benefit for rhinoconjunctivitis that cannot be achieved by the use of a single anti-allergic, or other active agent alone, for these same reasons.

In one particular embodiment, the cetirizine formulation of the invention comprises a stable ophthalmic formulation of cetirizine as the only active ingredient at a concentration of 0.01% to 1.0% (w/v), preferably 0.05% to 0.5% (w/v), or any specific value within said ranges. Preferably, cetirizine is in the form of cetirizine hydrochloride or dihydrochloride. Surprisingly, the stable cetirizine formulation is achieved without the use of a cyclodextrin, or other solubilizing compound, which were described as being required in U.S. Pat. No. 5,419,898.

In another particular embodiment, the invention provides a stable ophthalmic formulation of cetirizine in combination with fluticasone. Preferably, cetirizine is in the form of cetirizine hydrochloride or dihydrochloride. In certain embodiments, cetirizine is present in the formulation at a concentration of 0.05% to 1.0% (w/v), or any specific value within said range. For example, cetirizine is formulated at a concentration of 0.050% to 0.075%, 0.075% to 0.1%, 0.1% to 0.25%, 0.25% to 0.50%, 0.50% to 0.75%, or 0.75% to 1.0% (w/v), or any specific value within said ranges). In particular embodiments, cetirizine is formulated at a concentration of 0.05%, 0.1%, 0.2%, 0.25%, 0.3%, 0.35%, 0.4%, 0.45%, 0.5%, 0.6%, 0.7%, 0.8%, 0.9%, or 1.0% (w/v). In certain embodiments, fluticasone is present in the formulation at a concentration of 0.001% to 1.0% (w/v), or any specific value within said range. Preferably, fluticasone is present in the formulation at a concentration of 0.001% and 0.2% (w/v), or any specific value within said range. For example, fluticasone is formulated at a concentration of 0.001%, 0.005%, 0.01%, 0.015%, 0.025%, or 0.2% (w/v). In a particular embodiment, cetirizine is present in the formulation at a concentration of 0.1% (w/v) and fluticasone is present in the formulation at a concentration of 0.005% (w/v). In another particular embodiment, cetirizine is present in th formulation at a concentration of 0.25% (w/v) and fluticasone is present in the formulation at a concentration of 0.01% (w/v). The stable cetirizine/fluticasone formulation is achieved without the use of a cyclodextrin, or other solubilizing compound. The cetirizine alone, and combination formulations of the invention (e.g., cetirizine/fluticasone) are stable and comfortable upon instillation in the eye. Surprisingly, the cetirizine/fluticasone formulations of the invention do not increase intraocular pressure in the eye after repeated use (e.g., after 14 days). As such the cetirizine combination formulations of the invention are safe for ocular use.

In certain embodiments, the cetirizine alone and cetirizine combination formulations of the invention are formulated in a vehicle comprising 1% Polyethylene Glycol 400, NF; 0.2% Dibasic Sodium Phosphate, Anhydrous, USP; 0.25% Hypromellose, USP; 0.1% Polysorbate 80, NF; 1.2% to 1.8% Glycerin (or any specific value within said range), USP; 0.025% Edetate Disodium, USP; 0.01% Benzalkonium Chloride, NF (pH 7.0).

In some embodiments, the stable ophthalmic cetirizine formulations of the invention comprise a tear substitute. In particular embodiments, the tear substitute is hydroxypropylmethyl cellulose (Hypromellose or HPMC). According to some embodiments, the concentration of HPMC ranges from about 0.1% to about 2% w/v, or any specific value within said range. According to some embodiments, the concentration of HPMC ranges from about 0.5% to about 1% w/v, or any specific value within said range. In a preferred embodiments, the concentration of HPMC ranges from about 0.1% to about 1.0% w/v, or any specific value within said range (e.g., 0.1-0.2%, 0.2-0.3%, 0.3-0.4%, 0.4-0.5%, 0.5-0.6%, 0.6-0.7%, 0.7-0.8%, 0.8-0.9%, 0.9-1.0%; about 0.2%, about 0.21%, about 0.22%, about 0.23%, about 0.24%, about 0.25%, about 0.26%, about 0.27%, about 0.28%, about 0.29%, about 0.30%, about 0.70%, about 0.71%, about 0.72%, about 0.73%, about 0.74%, about 0.75%, about 0.76%, about 0.77%, about 0.78%, about 0.79%, about 0.80%, about 0.81%, about 0.82%, about 0.83%, about 0.84%, about 0.85%, about 0.86%, about 0.87%, about 0.88%, about 0.89%, or about 0.90%).

In another particular embodiment the tear substitute is carboxymethyl cellulose (CMC). According to some embodiments, the concentration of CMC ranges from about 0.1% to about 2% w/v, or any specific value within said range. According to some embodiments, the concentration of CMC ranges from about 0.1% to about 1% w/v, or any specific value within said range. In a preferred embodiments, the concentration of CMC ranges from about 0.7% to about 0.9% w/v, or any specific value within said range (i.e., about 0.70%, about 0.71%, about 0.72%, about 0.73%, about 0.74%, about 0.75%, about 0.76%, about 0.77%, about 0.78%, about 0.79%, about 0.80%, about 0.81%, about 0.82%, about 0.83%, about 0.84%, about 0.85%, about 0.86%, about 0.87%, about 0.88%, about 0.89%, or about 0.90%).

In yet another particular embodiment, the stable ophthalmic cetirizine formulations of the invention comprise a polymeric, mucoadhesive vehicle. Examples of mucoadhesive vehicles suitable for use in the methods or formulations of the invention include but are not limited to aqueous polymeric suspensions comprising one or more polymeric suspending agents including without limitation dextrans, polyethylene glycol, polyvinylpyrolidone, polysaccharide gels, Gelrite®, cellulosic polymers, and carboxy-containing polymer systems. In a particular embodiment, the polymeric suspending agent comprises a crosslinked carboxy-containing polymer (e.g., polycarbophil). In another particular embodiment, the polymeric suspending agent comprises a polyethylene glycol (PEG). Examples of cross-linked carboxy-containing polymer systems suitable for use in the topical stable ophthalmic cetirizine formulations of the invention include but are not limited to Noveon AA-1, Carbopol®, and/or DuraSite® (InSite Vision).

Optionally, the formulations of the invention contain a preservative. In particular embodiments the preservative is benzalkonium chloride or a derivative thereof (e.g., Polyquad®), or a stabilized oxychloro complex (e.g., Purite®).

According to some embodiments, the ophthalmic formulations of the present invention has a viscosity that ranges from about 30 to about 150 centipoise (cpi), preferably about 50 to about 120 cpi, even more preferably about 60 to about 115 cpi (or any specific value within said ranges). According to preferred embodiments, the ophthalmic formulations of the present invention has a viscosity that ranges from about 60 to about 80 cpi, or any specific value within said range (i.e., about 60 cpi, about 61 cpi, about 62 cpi, about 63 cpi, about 64 cpi, about 65 cpi, about 66 cpi, about 67 cpi, about 68 cpi, about 69 cpi, about 70 cpi, about 71 cpi, about 72 cpi, about 73 cpi, about 74 cpi, about 75 cpi, about 76 cpi, about 77 cpi, about 78 cpi, about 79 cpi, or about 80 cpi).

The invention also provides methods of treating and preventing the symptoms of allergic conjunctivitis by administering a stable cetirizine formulation of the invention (i.e., cetirizine alone or in combination with an additional active agent such as a steroid (e.g., fluticasone) or a vasoconstrictor (e.g., naphazoline or oxymetazoline) directly to the eye of a subject in need of such treatment or prevention. Preferably, the formulation of the invention is administered once a day (q.d.). In certain embodiments, the methods of the invention (i.e., administration of a formulation of the invention directly to the eye) are also effective to treat nasal symptoms associated with allergic conjunctivitis. The invention also provides methods of treating and preventing the symptoms of allergic rhinoconjunctivitis by administering a stable cetirizine formulation of the invention (i.e., cetirizine alone or in combination with an additional active agent such as a steroid (e.g., fluticasone) or a vasoconstrictor (e.g., naphazoline or oxymetazoline) directly to the eye of a subject in need of such treatment or prevention. By providing a treatment option in eye drop form, the present invention will improve quality of life in patients with allergic rhinoconjunctivitis/rhinitis (See e.g., Berger et al., *Ann. Allergy Asthma Immunol.* October 95(4), 361-71 (2005).

The invention further provides kits comprising a pharmaceutical composition of cetirizine formulated for ophthalmic use and instructions for such use. Other features and advantages of the invention will become apparent from the following detailed description and claims.

BRIEF DESCRIPTION OF THE DRAWINGS

FIG. 1A is a line graph depicting the efficacy of a 0.1% cetirizine formulation reducing of ocular itching as compared to a vehicle control. The mean ocular itching score (scale of 0 to 4) is shown at 0, 3, 5, and 7 minutes after conjunctival challenge with allergen; FIG. 1B is a line graph depicting the efficacy of a 0.1% cetirizine formulation reducing conjunctival redness as compared to a vehicle control FIG. 2 is a line graph depicting the comfort profile of a 0.1% cetirizine formulation upon instillation in the eye as compared to a vehicle control. The comfort of the formulation is indicated on a subjective scale of 0 to 10 (0=very comfortable; 10=very uncomfortable). The mean drop comfort score is shown at 0, 1, 2 minutes after addition of a drop of the cetirizine formulation of the invention.

FIGS. 3A and 3B depict a study design (screening and evaluation) for testing the efficacy of Fluticasone 0.001%, 0.005% and 0.01% as compared to vehicle in reducing ocular and nasal symptoms of ocular allergy in an allergic conjunctivitis model.

FIG. 4 is a line graph comparing the efficacy of Fluticasone 0.001%, 0.005% and 0.01% as compared to vehicle in reducing ocular itching assessed on a scale of 0 (no itching) to 4 (severe itching) over time.

FIG. 5 is a line graph comparing the efficacy of Fluticasone 0.001%, 0.005% and 0.01% as compared to vehicle in reducing conjunctival redness, assessed on a scale of 0 (no redness) to 4 (severe redness) over time.

FIG. 6 is line graph comparing the efficacy of Fluticasone 0.001%, 0.005% and 0.01% as compared to vehicle in reducing lidswelling, assessed on a scale of 0 (no swelling) to 3 (severe swelling) over time.

FIG. 7 is a line graph comparing the efficacy of Fluticasone 0.001%, 0.005% and 0.01% as compared to vehicle in reducing nasal congestion, assessed on a scale of 0 (no congestion) to 4 (severe congestion) over time.

FIG. 8 is a bar graph summarizing the results shown in FIGS. 3-7.

FIG. 9 is a line graph comparing the efficacy of Fluticasone 0.001%, 0.005% and 0.01% as compared to vehicle in reducing ciliary redness, assessed on a scale of 0 (no redness) to 4 (severe redness) over time.

FIG. 10 is a line graph comparing the efficacy of Fluticasone 0.001%, 0.005% and 0.01% as compared to vehicle in reducing episcleral redness, assessed on a scale of 0 (no redness) to 4 (severe redness) over time.

FIG. 11 is a line graph comparing the efficacy of Fluticasone 0.001%, 0.005% and 0.01% as compared to vehicle in reducing chemosis, assessed on a scale of 0 (none) to 4 (severe) over time.

FIG. 12 is a line graph comparing the efficacy of Fluticasone 0.001%, 0.005% and 0.01% as compared to vehicle in reducing watery eyes, assessed on a scale of 0 (none) to 4 (severe) over time.

FIG. 13 is a bar graph summarizing the results shown in FIGS. 9-11.

FIG. 14 is a line graph comparing the efficacy of Fluticasone 0.001%, 0.005% and 0.01% as compared to vehicle in reducing rhinorrhea, assessed on a scale of 0 (none) to 4 (severe) over time.

FIG. 15 is a line graph comparing the efficacy of Fluticasone 0.001%, 0.005% and 0.01% as compared to vehicle in reducing ear or palate pruritis, assessed on a scale of 0 (none) to 4 (severe) over time.

FIG. 16 is a line graph comparing the efficacy of Fluticasone 0.001%, 0.005% and 0.01% as compared to vehicle in reducing nasal pruritis, assessed on a scale of 0 (none) to 4 (severe) over time.

FIG. 17 is a line graph comparing the efficacy of Fluticasone 0.001%, 0.005% and 0.01% as compared to vehicle on total nasal score, assessed on a scale of 0 (no nasal symptoms) to 16 (multiple nasal symptoms) over time.

FIG. 18 is a bar graph summarizing the results shown in FIGS. 14-17.

FIG. 19 is a line graph comparing the efficacy of Fluticasone 0.001%, 0.005% and 0.01% as compared to vehicle on peak nasal inspiratory flow (PNIF).

FIG. 20 a line graph comparing the drop comfort of Fluticasone 0.001%, 0.005% and 0.01% as compared to vehicle, assessed on a scale of 0 (extremely comfortable) to 10 (extremely uncomfortable) over time at Visit 2.

FIG. 21 a line graph comparing the drop comfort of Fluticasone 0.001%, 0.005% and 0.01% as compared to vehicle, assessed on a scale of 0 (extremely comfortable) to 10 (extremely uncomfortable) over time at Visit 3.

FIG. 22 is a chart summarizing the incidence of adverse events associated with instillation of Fluticasone 0.001%, 0.005% and 0.01% in the eye.

FIG. 23 is a bar graph summarizing the effects of Fluticasone 0.001%, 0.005% and 0.01% as compared to vehicle on intraocular pressure.

FIG. 29 is a line graph depicting the comfort profile of a 0.1% cetirizine/0.005% fluticasone formulation (low dose) and a 0.25% cetirizine/0.01% fluticasone formulation (high dose) upon instillation in the eye as compared to controls. The comfort of the formulation is indicated on a subjective scale of 0 to 10 (0=very comfortable; 10=very uncomfortable).

DETAILED DESCRIPTION OF THE INVENTION

Figure 24:
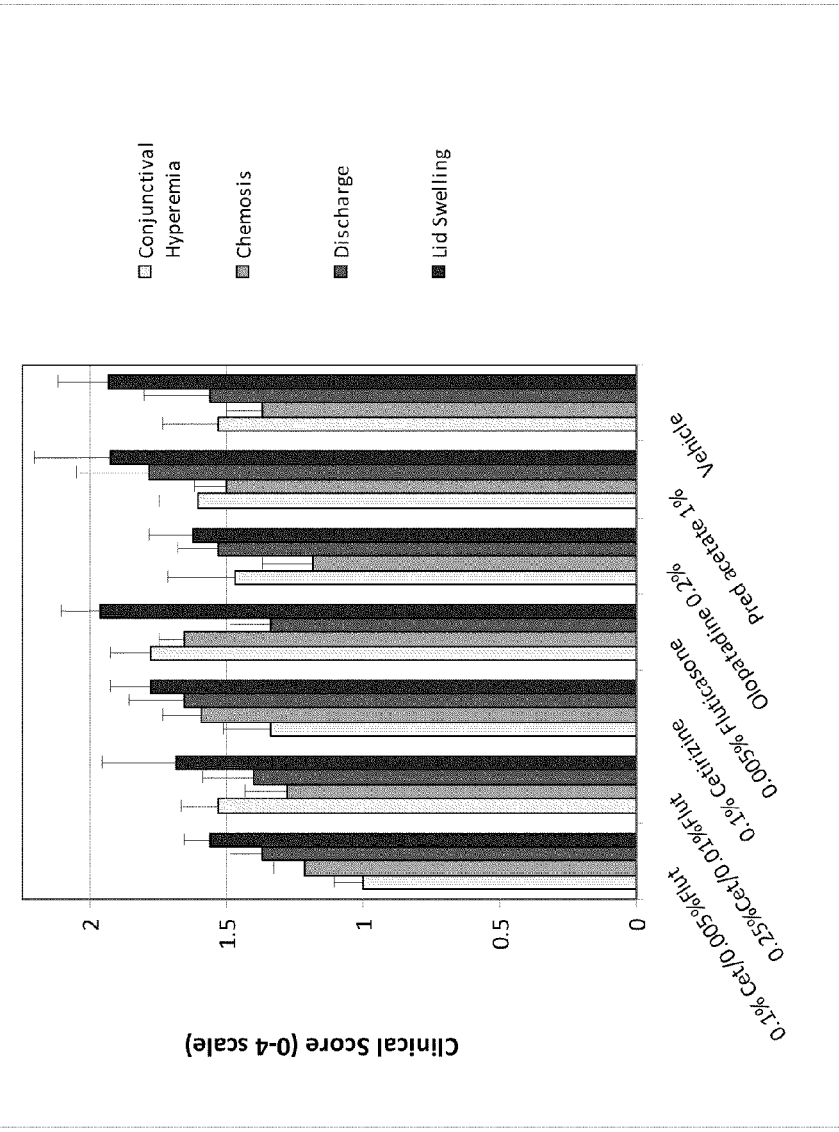
FIG. 24 is a bar graph summarizing the effects of a 0.1% cetirizine/0.005% fluticasone formulation (low dose) and a 0.25% cetirizine/0.01% fluticasone formulation (high dose) on conjunctival hyperemia, chemosis, discharge, and lid swelling after three days of dosing, as compared to 0.1% cetirizine alone, 0.005% fluticasone alone, a leading commercial antihistamine for treating allergic conjunctivitis (Pataday®; olopatadine 0.2%), a commercially available steroid (Pred Forte®; prednisolone acetate 1%) and a vehicle control.

The invention is based in part on the discovery that low concentrations of cetirizine (i.e., less than 1%) can be prepared as a stable ophthalmic formulation, without the use of a cyclodextrin or other solubilizing compound. Such formulations are comfortable and safe for ocular use and effective at reducing the symptoms of allergic conjunctivitis and/or allergic rhinoconjunctivitis, particularly ocular itching and/or nasal symptoms (e.g., itchy, running nose, sneezing, nasal/sinus congestion).

The historical difficulty in preparing cetirizine as an ophthalmic solution with satisfactory safety and stability profiles is well recognized in the art due to the fact that cetirizine aggregates in solution at low concentrations, and is highly irritating to the ocular surface at high concentrations, being a strong acid. Without intending to be bound by any theory, it was believed necessary to reduce the possibility of salt formation and metal based degradation in order to arrive at a stable formulation. As such, the addition of counter ions or metal based buffers that could promote salt formation, precipitation, or metal based degradation were minimized or excluded from the cetirizine formulations of the invention. Furthermore, it was discovered that the pH could be adjusted to approximately 7.0 with no adverse effects on stability, to improve the comfort of the formula.

The invention features novel topical ophthalmic formulations comprising an effective amount of cetirizine, or a pharmaceutically acceptable salt thereof, in a pharmaceutically acceptable carrier. Pharmaceutically acceptable cetirizine salts include cetirizine hydrochloride or cetirizine dihydrochloride. In particular embodiments, the invention provides stable ophthalmic formulations of cetirizine as the only active agent in the formulations. The invention also features ophthalmic formulations of cetirizine in combination with one or more additional active ingredients selected from oxymetazoline, naphazoline and fluticasone. Such combination formulations are effective in further mitigating the acute and late phase signs and symptoms of allergic conjunctivitis, such as ocular itching, redness, chemosis, lid swelling and nasal symptoms. Such formulations are also effective in mitigating the signs and symptoms of rhinoconjunctivitis, such as runny nose, sneezing, nasal/sinus congestion and red, watery and/or itchy eyes.

The comfort, safety, efficacy, solubility, and stability of the ophthalmic formulations of the invention could not have been predicted by one skilled in the art. Many antihistamines have been developed over the years by various companies for different indications. However, not all of these can be formulated or are effective as an eyedrop. Likewise not all antihistamines have the same duration of action. For example the potent antihistamine levocabastine has a duration of 2-4 hours; recently approved bepotastine (Bepreve®-ISTA), indicated for twice daily dosing, has an 8 hour duration; olopatadine 0.1% (Patanol®) indicated for twice daily dosing, has an 8 hour duration; and olopatadine 0.2% (Pataday®), indicated for once daily dosing, has a 16 hour duration of action. Therefore the efficacy is not predictable. In one study (Berdy et al, 1990), a panel of antihistamines were screened yet only a few were suitable for the eye based on comfort, formulation, irritation, and efficacy. As evidenced by Berdy et al., one skilled in the art could not have predicted which of the antihistamines would be ideal for ocular use or for treating ocular allergy. The invention is based, in part, upon the surprising and unpredictable discovery that an antihistamine and a steroid, when combined, act synergistically to treat both the acute and late phase reactions of allergic conjunctivitis, as well as allergic rhinoconjunctivitis.

In some embodiment, the cetirizine formulations of the invention comprise one or more tear substitute components. The cetirizine component provides relief of the symptoms of allergic conjunctivitis, and the one or more tear substitute component provides ocular surface protection via enhancement of the tear film (as evident by increased tear film break up time), and can act to enhance dwell time on the ocular surface thus increasing duration of activity. An effective amount of such formulations may be used to treat and/or prevent signs and symptoms associated with acute and/or late phase allergic conjunctivitis and/or general eye irritation, and can also be used to treat another eye disorder if it contains a drug for that disorder. An effective amount of such formulations may also be used to treat and/or prevent signs and symptoms of allergic rhinoconjunctivitis. Such formulations provide a comfortable ophthalmic formulation when instilled in the eye and have enhanced efficacy and/or duration of action over formulations of cetirizine that are not combined with such other agents.

The superior efficacy of the combination cetirizine/tear substitute formulations is attributed to, among other things, the synergistic effect of the combination of ingredients in them. The combination of cetirizine and tear substitute, act synergistically to provide a longer dwell time of the cetirizine on the ocular surface, thus increasing duration and efficacy of action, and to prolong the integrity of the tear film thereby providing protection of the ocular surface (e.g., by increasing the tear film break up time and/or the Ocular Protection Index). As such, the compositions of the invention are comfortable upon instillation into the eye, and may be used for relief of acute or chronic allergic conjunctivitis, and are particularly suitable for both intermittent and long term use.

Formulations

In the context of this patent all concentrations are given for the cetirizine free base. The concentration for the cetirizine salt (e.g. cetirizine hydrochloride or dihydrochloride) can be calculated by multiplying the free base concentration by 1.188. e.g. 0.1% cetirizine free base is equivalent to 0.1188% cetirizine hydrochloride salt (0.1%×1.188=0.11881%).

Preferably, the ophthalmic formulations according to the present invention are formulated as solutions, suspensions, ointments, gels, emulsions, oils, and other dosage forms for topical administration. Aqueous solutions are generally preferred, based on ease of formulation, as well as a patient's ability to easily administer such compositions by means of instilling one to two drops of the solutions in the affected eyes. However, the compositions may also be suspensions, viscous or semi-viscous gels, or other types of solid or semi-solid compositions or sustained release devices or mechanisms that are placed in or around the eye. In one embodiment, the cetirizine formulations of the invention are aqueous formulations. The aqueous formulations of the invention are typically more than 50%, preferably more than 75%, and most preferably more than 90% by weight water. Preferably, the aqueous formulation does not contain a cyclodextrin or other solubilizer compound. Stable aqueous formulations of cetirizine are achieved by minimizing/excluding the addition of counter ions or metal based buffers that could promote salt formation, precipitation, or metal based degradation. In another embodiment, the cetirizine formulations are lyophilized formulations.

Active Agents

Cetirizine is the primary active agent in the ophthalmic formulations of the present invention, and in certain embodiments, the only active agent in the formulations of the invention. In certain embodiments of the invention, cetirizine, or a pharmaceutically acceptable salt thereof, is formulated at a concentration of 0.01% to 1.0% (w/v). Preferably, cetirizine is in the form of cetirizine hydrochloride or dihydrochloride. In certain embodiments, cetirizine is formulated at a concentration of 0.05% to 0.075%, 0.075% to 0.1%, 0.1% to 0.25%, 0.25% to 0.50%, 0.50% to 0.75%, or 0.75% to 1.0% (w/v). In particular embodiments, cetirizine is formulated at a concentration of 0.05% to 1.0% (w/v), or any specific value within said range. For example, cetirizine is formulated at a concentration of 0.05%, 0.1%, 0.2%, 0.25%, 0.3%, 0.35%, 0.4%, 0.45%, 0.5%, 0.6%, 0.7%, 0.8%, 0.9%, or 1.0% (w/v). (w/v). In one embodiment, the cetirizine formulation of the invention comprises cetirizine hydrochloride or dihydrochloride as the only active ingredient at a concentration of 0.01% to 1.0% (w/v), preferably 0.05% to 0.5% (w/v), more preferably 0.1% to 0.25% (w/v) (or any specific value within said ranges).

Cetirizine may be formulated with other active agents as described herein. For example, cetirizine may be formulated with one or more additional anti-allergic agents. The term "anti-allergenic agent" refers to a molecule or composition that treats allergic conjunctivitis and/or rhinoconjunctivitis or reduces a symptom of allergic conjunctivitis and/or rhinoconjunctivitis. The term "allergic conjunctivitis" refers to any allergic disease of the eye, e.g., seasonal/perennial allergic conjunctivitis, vernal keratoconjunctivitis, giant papillary conjunctivitis, perennial allergic conjunctivitis and atopic keratoconjunctivitis. The signs and symptoms of ocular allergies include chemosis, eye itching, tearing, redness and swelling, and may also co-exist with nasal symptomatology. The term "allergic rhinoconjunctivitis" refers to a combination of nasal and ocular symptoms characterized by inflammation of the lining of the tissue of the eyes and nose due to an allergy or infection, causing nasal discharge, mucus, sneezing, irritation, and red, water, itchy eyes. Non-limiting examples of anti-allergic agents include "antihistamines" or drugs which block histamine from binding to the histamine receptors, "mast cell stabilizers" or drugs that block the release of histamine and other substances from the mast cell, "drugs with multiple modes of action" or drugs that are anti-allergenic agents having multiple modes of action (e.g. drugs that are antihistamines and mast cell stabilizers, drugs with antihistamine, mast cell stabilizing and anti-inflammatory activity, etc.), steroids, and nonsteroidal anti-inflammatory drugs or "NSAIDs."

In certain embodiments, cetirizine is formulated with one or more additional active agents selected from a mast cell stabilizer such as nedocromil, iodoxamide, cromolyn, or cromolyn sodium; a non-steroidal anti-inflammatory drug ("NSAID") such as diclofenac or ketorolac tromethamine, bromfenac, or nepafenac; a vasoconstrictor such as naphazoline, antolazine, tetrahydrozoline or oxymetazoline; a topical steroid such as fluticasone, beclomethasone, budesonide, diflorasone, triaminicinolone, clobetasol, difluprednate, prednisolone, dexamethasone, halobetasol, or mometasone; an antihistimine such as antazoline, astemizole, azelastine, bepotastine, bilastine, brompheniramine, chlorpheniramine, clemastine, desloratidine, dexbrompheniramine, diphenhydramine, doxylamine, ebastine, emedastine, epinastine, fexofenadine, hydroxyzine, ketotifen, levocabastine, levocetirizine, loratidine, mequitazine, mizolastine, olopatadine, oxatomide, phenindamine, pheniramine, pyrilamine, terfenidine, and triprolidine; or an alpha-adrenergic agonist such as epinephrine, fenoxazoline, indanazoline, naphazoline, oxedrine, phenylephrine, tefazoline, tetryzoline, tramazoline, tymazoline, oxymetazoline, or xylometazoline.

In certain embodiments, cetirizine is formulated with one or more additional active agents such as a vasoconstrictor (e.g., naphazoline or oxymetazoline), or a steroid (e.g., fluticasone).

Naphazoline (in the hydrochloride form) is the common name for 2-(1-naphthylmethyl)-2-imidazoline hydrochloride. It is a sympathomimetic agent with marked alpha adrenergic activity. It is a vasoconstrictor with a rapid action in reducing swelling when applied to mucous membrane. It acts on alpha-receptors in the arterioles of the conjunctiva to produce constriction, resulting in decreased congestion. Oxymetazoline is a selective alpha-1 agonist and partial alpha-2 agonist topical decongestant, used in the form of oxymetazoline hydrochloride in commercially available nasal sprays. Oxymetazoline has sympathomimetic properties, and thus constricts the blood vessels of the nose and sinuses via activation of alpha-2 adrenergic receptors. Fluticasone is a potent synthetic corticosteroid often prescribed as treatment for asthma and allergic rhinitis.

In certain embodiments, cetirizine is formulated at a concentration of from 0.05% to 0.50% (w/v), in combination with naphazoline at a concentration of from 0.01% to 0.5% (w/v), preferably 0.01% to 0.1% (w/v), preferably 0.05% to 0.1% (w/v), more preferably 0.09% to 0.1% (w/v). In particular embodiments, cetirizine is formulated at a concentration of 0.01%, 0.05%, 0.06%, 0.07%, 0.08%, 0.09%, 0.10%, 0.15%, 0.20%, 0.25%, 0.30%, 0.35%, 0.45%, or 0.50% (w/v) in combination with naphazoline at a concentration of 0.01%, 0.02%, 0.03%, 0.04%, 0.05%, 0.06% 0.07%, 0.08%, 0.09% or 0.10% (w/v).

In certain embodiments, cetirizine is formulated at a concentration of from 0.05% to 0.50% (w/v) in combination with oxymetazoline at a concentration of from 0.01% to about 0.2% (w/v), preferably 0.01% to 0.1% (w/v), more preferably 0.03% to 0.05% (w/v). In particular embodiments, cetirizine is formulated at a concentration of 0.05%, 0.06%, 0.07%, 0.08%, 0.09%, 0.10%, 0.15%, 0.20%, 0.25%, 0.30%, 0.35%, 0.45%, or 0.50% (w/v) in combination with oxymetazoline at a concentration of 0.01%, 0.02%, 0.03%, 0.04%, 0.05%, 0.06%, 0.07% 0.09% or 0.10% (w/v).

In certain embodiments, cetirizine is formulated at a concentration of from 0.05% to 0.50% (w/v) in combination with fluticasone at a concentration of from 0.001% to 1.0% (w/v), preferably 0.001% to 0.2% (w/v), or any specific value within said ranges. In particular embodiments, cetirizine is formulated at a concentration of 0.05%, 0.06%, 0.07%, 0.08%, 0.09%, 0.10%, 0.15%, 0.20%, 0.25%, 0.30%, 0.35%, 0.45%, or 0.50% (w/v) in combination with fluticasone at a concentration of 0.001%, 0.002%, 0.003%, 0.004%, 0.005%, 0.01%, 0.015%, 0.05%, 0.1%, 0.2%, 0.5%, or 1% (w/v). In a particular embodiment, the cetirizine is present in the formulation at a concentration of 0.25% (w/v) and the fluticasone is present in the formulation at a concentration of 0.01% (w/v). In another particular embodiment, the cetirizine is present in the formulation at a concentration of 0.1% (w/v) and the fluticasone is present in the formulation at a concentration of 0.005% (w/v).

In certain embodiments, the viscosity of the cetirizine formulations of the invention (i.e. cetirizine alone or in combination with an additional active agent) ranges from 1-50 centipoise (cpi), or any specific value within said range. In a particular embodiment, the viscosity of the cetirizine formulations of the invention range from 5-30 cpi, preferably 10-20 cpi.

Excipients

In some embodiments, the cetirizine formulations of the invention comprise one or more pharmaceutically acceptable excipients. The term excipient as used herein broadly refers to a biologically inactive substance used in combination with the active agents of the formulation. An excipient can be used, for example, as a solubilizing agent, a stabilizing agent, a surfactant, a demulcent, a viscosity agent, a diluent, an inert carrier, a preservative, a binder, a disintegrant, a coating agent, a flavoring agent, or a coloring agent. Preferably, at least one excipient is chosen to provide one or more beneficial physical properties to the formulation, such as increased stability and/or solubility of the active agent(s). A "pharmaceutically acceptable" excipient is one that has been approved by a state or federal regulatory agency for use in animals, and preferably for use in humans, or is listed in the U.S. Pharmacopia, the European Pharmacopia or another generally recognized pharmacopia for use in animals, and preferably for use in humans.

Further examples of excipients include certain inert proteins such as albumins; hydrophilic polymers such as polyvinylpyrrolidone; amino acids such as aspartic acid (which may alternatively be referred to as aspartate), glutamic acid (which may alternatively be referred to as glutamate), lysine, arginine, glycine, and histidine; fatty acids and phospholipids such as alkyl sulfonates and caprylate; surfactants such as sodium dodecyl sulphate and polysorbate; nonionic surfactants such as such as TWEEN®, PLURONICS®, or a polyethylene glycol (PEG) designated 200, 300, 400, or 600; a Carbowax designated 1000, 1500, 4000, 6000, and 10000; carbohydrates such as glucose, sucrose, mannose, maltose, trehalose, and dextrins, including cyclodextrins; polyols such as mannitol and sorbitol; chelating agents such as EDTA; and salt-forming counter-ions such as sodium.

Examples of carriers that may be used in the formulations of the present invention include water, mixtures of water and water-miscible solvents, such as $C_1$- to $C_7$-alkanols, vegetable oils or mineral oils comprising from 0.5 to 5% non-toxic water-soluble polymers, natural products, such as gelatin, alginates, pectins, tragacanth, karaya gum, xanthan gum, carrageenin, agar and acacia, starch derivatives, such as starch acetate and hydroxypropyl starch, and also other synthetic products, such as polyvinyl alcohol, polyvinylpyrrolidone, polyvinyl methyl ether, polyethylene oxide, preferably cross-linked polyacrylic acid, such as neutral Carbopol, or mixtures of those polymers. The concentration of the carrier is, typically, from 1 to 100000 times the concentration of the active ingredient.

In a particular embodiment, the carrier is a polymeric, mucoadhesive vehicle. Examples of mucoadhesive vehicles suitable for use in the methods or formulations of the invention include but are not limited to aqueous polymeric suspensions comprising one or more polymeric suspending agents including without limitation dextrans, polyethylene glycol, polyvinylpyrolidone, polysaccharide gels, Gelrite®, cellulosic polymers, and carboxy-containing polymer systems. In a particular embodiment, the polymeric suspending agent comprises a crosslinked carboxy-containing polymer (e.g., polycarbophil). In another particular embodiment, the polymeric suspending agent comprises polyethylene glycol (PEG). Examples of cross-linked carboxy-containing polymer systems suitable for use in the topical stable ophthalmic cetirizine formulations of the invention include but are not limited to Noveon AA-1, Carbopol®, and/or DuraSite® (InSite Vision).

In particular embodiments, the cetirizine formulations of the invention comprise one or more excipients selected from among the following: a tear substitute, a tonicity enhancer, a preservative, a solubilizer, a viscosity enhancing agent, a demulcent, an emulsifier, a wetting agent, a sequestering agent, and a filler. The amount and type of excipient added is in accordance with the particular requirements of the formulation and is generally in the range of from about 0.0001% to 90% by weight.

Tear Substitutes

The term "tear substitute" refers to molecules or compositions which lubricate, "wet," approximate the consistency of endogenous tears, aid in natural tear build-up, or otherwise provide temporary relief of dry eye signs or symptoms and conditions upon ocular administration. A variety of tear substitutes are known in the art and include, but are not limited to: monomeric polyols, such as, glycerol, propylene glycol, and ethylene glycol; polymeric polyols such as polyethylene glycol; cellulose esters such hydroxypropylmethyl cellulose, carboxymethyl cellulose sodium and hydroxy propylcellulose; dextrans such as dextran 70; water soluble proteins such as gelatin; vinyl polymers, such as polyvinyl alcohol, polyvinylpyrrolidone, and povidone; and carbomers, such as carbomer 934P, carbomer 941, carbomer 940 and carbomer 974P. Many such tear substitutes are commercially available, which include, but are not limited to cellulose esters such as Bion Tears®, Celluvisc®, Genteal®, OccuCoat®, Refresh®, Systane®, Teargen II®, Tears Naturale®, Tears Natural II®, Tears Naturale Free®, and TheraTears®; and polyvinyl alcohols such as Akwa Tears®, HypoTears®, Moisture Eyes®, Murine Lubricating®, and Visine Tears®, Soothe®. Tear substitutes may also be comprised of paraffins, such as the commercially available Lacri-Lube@ ointments. Other commercially available ointments that are used as tear substitutes include Lubrifresh PM®, Moisture Eyes PM® and Refresh PM®.

In one preferred embodiment of the invention, the tear substitute comprises hydroxypropylmethyl cellulose (Hypromellose or HPMC). According to some embodiments, the concentration of HPMC ranges from about 0.1% to about 2% w/v, or any specific value within said range. According to some embodiments, the concentration of HPMC ranges from about 0.5% to about 1.5% w/v, or any specific value within said range. According to some embodiments, the concentration of HPMC ranges from about 0.1% to about 1% w/v, or any specific value within said range. According to some embodiments, the concentration of HPMC ranges from about 0.6% to about 1% w/v, or any specific value within said range. In a preferred embodiments, the concentration of HPMC ranges from about 0.1% to about 1.0% w/v, or any specific value within said range (i.e., 0.1-0.2%, 0.2-0.3%, 0.3-0.4%, 0.4-0.5%, 0.5-0.6%, 0.6-0.7%, 0.7-0.8%, 0.8-0.9%, 0.9-1.0%; about 0.2%, about 0.21%, about 0.22%, about 0.23%, about 0.24%, about 0.25%, about 0.26%, about 0.27%, about 0.28%, about 0.29%, about 0.30%, about 0.70%, about 0.71%, about 0.72%, about 0.73%, about 0.74%, about 0.75%, about 0.76%, about 0.77%, about 0.78%, about 0.79%, about 0.80%, about 0.81%, about 0.82%, about 0.83%, about 0.84%, about 0.85%, about 0.86%, about 0.87%, about 0.88%, about 0.89%, or about 0.90%).

For example, without limitation, a tear substitute which comprises hydroxypropyl methyl cellulose is GenTeal® lubricating eye drops. GenTeal® (CibaVision—Novartis) is a sterile lubricant eye drop containing hydroxypropylmethyl cellulose 3 mg/g and preserved with sodium perborate. Other examples of an HPMC-based tear are provided.

In another preferred embodiment, the tear substitute comprises carboxymethyl cellulose sodium. For example, without limitation, the tear substitute which comprises carboxymethyl cellulose sodium is Refresh® Tears. Refresh® Tears is a lubricating formulation similar to normal tears, containing a, mild non-sensitizing preservative, stabilised oxychloro complex (Purite®)), that ultimately changes into components of natural tears when used.

In a preferred embodiment, the tear substitute, or one or more components thereof, is an aqueous solution having a viscosity in a range which optimizes efficacy of supporting the tear film while minimizing blurring, lid caking, etc. Preferably, the viscosity of the tear substitute, or one or more components thereof, ranges from 1-150 centipoise (cpi), e.g., 5-150 cpi, 5-130 cpi, 30-130 cpi, 50-120 cpi, 60-115 cpi (or any specific value within said ranges). In a particular embodiment, the viscosity of the tear substitute, or one or more components thereof, is about 70-90 cpi, or any specific value within said range (for example without limitation, 85 cpi).

Viscosity may be measured at a temperature of 20° C.+/−1° C. using a Brookfield Cone and Plate Viscometer Model VDV-III Ultra+ with a CP40 or equivalent Spindle with a shear rate of approximately 22.50+/−approximately 10 (1/sec), or a Brookfield Viscometer Model LVDV-E with a SC4-18 or equivalent Spindle with a shear rate of approximately 26+/−approximately 10 (1/sec). Alternatively, viscosity may be measured at 25° C.+/−1° C. using a Brookfield Cone and Plate Viscometer Model VDV-III Ultra+ with a CP40 or equivalent Spindle with a shear rate of approximately 22.50+/−approximately 10 (1/sec), or a Brookfield Viscometer Model LVDV-E with a SC4-18 or equivalent Spindle with a shear rate of approximately 26+/−approximately 10 (1/sec).

In some embodiments, the tear substitute, or one or more components thereof is buffered to a pH 5.0 to 9.0, preferably pH 5.5 to 7.5, more preferably pH 6.0 to 7.0 (or any specific value within said ranges), with a suitable salt (e.g., phosphate salts). In some embodiments, the tear substitute further comprises one or more ingredients, including without limitation, glycerol, propyleneglycerol, glycine, sodium borate, magnesium chloride, and zinc chloride.

Salts, Buffers, and Preservatives

The formulations of the present invention may also contain pharmaceutically acceptable salts, buffering agents, or preservatives. Examples of such salts include those prepared from the following acids: hydrochloric, hydrobromic, sulfuric, nitric, phosphoric, maleic, acetic, salicylic, citric, boric, formic, malonic, succinic, and the like. Such salts can also be prepared as alkaline metal or alkaline earth salts, such as sodium, potassium or calcium salts. Examples of buffering agents include phosphate, citrate, acetate, and 2-(N-morpholino)ethanesulfonic acid (MES).

For the adjustment of the pH, preferably to a physiological pH, buffers may especially be useful. The pH of the present solutions should be maintained within the range of 4.0 to 8.0, more preferably about 5.5 to 7.5, more preferably about 6.0 to 7.0. Suitable buffers may be added, such as boric acid, sodium borate, potassium citrate, citric acid, sodium bicarbonate, TRIS, and various mixed phosphate buffers (including combinations of $Na_2HPO_4$, $NaH_2PO_4$ and $KH_2PO_4$) and mixtures thereof. Borate buffers are preferred. Generally, buffers will be used in amounts ranging from about 0.05 to 2.5 percent by weight, and preferably, from 0.1 to 1.5 percent.

In certain embodiments, the topical formulations additionally comprise a preservative. A preservative may typically be selected from a quaternary ammonium compound such as benzalkonium chloride, benzoxonium chloride or the like. Benzalkonium chloride is better described as: N-benzyl-N—($C_8$-$C_{18}$ alkyl)-N,N-dimethylammonium chloride. Further examples of preservatives include antioxidants such as vitamin A, vitamin E, vitamin C, retinyl palmitate, and selenium; the amino acids cysteine and methionine; citric acid and sodium citrate; and synthetic preservatives such as thimerosal, and alkyl parabens, including for example, methyl paraben and propyl paraben. Other preservatives include octadecyldimethylbenzyl ammonium chloride, hexamethonium chloride, benzethonium chloride, phenol, catechol, resorcinol, cyclohexanol, 3-pentanol, m-cresol, phenylmercuric nitrate, phenylmercuric acetate or phenylmercuric borate, sodium perborate, sodium chlorite, alcohols, such as chlorobutanol, butyl or benzyl alcohol or phenyl ethanol, guanidine derivatives, such as chlorohexidine or polyhexamethylene biguanide, sodium perborate, Polyquad®, Germal®II, sorbic acid and stabilized oxychloro complexes (e.g., Purite®). Preferred preservatives are quaternary ammonium compounds, in particular benzalkonium chloride or its derivative such as Polyquad (see U.S. Pat. No. 4,407,791), alkyl-mercury salts, parabens and stabilized oxychloro complexes (e.g., Purite®). Where appropriate, a sufficient amount of preservative is added to the ophthalmic composition to ensure protection against secondary contaminations during use caused by bacteria and fungi.

In particular embodiments, the cetirizine formulations of the invention comprise a preservative selected from among the following: benzalkonium chloride, 0.001% to 0.05%; benzethonium chloride, up to 0.02%; sorbic acid, 0.01% to 0.5%; polyhexamethylene biguanide, 0.1 ppm to 300 ppm; polyquaternium-1 (Omamer M) −0.1 ppm to 200 ppm; hypochlorite, perchlorite or chlorite compounds, 500 ppm or less, preferably between 10 and 200 ppm); stabilized hydrogen peroxide solutions, a hydrogen peroxide source resulting in a weight % hydrogen peroxide of 0.0001 to 0.1% along with a suitable stabilizer; alkyl esters of p-hydroxybenzoic acid and mixtures thereof, preferably methyl paraben and propyl paraben, at 0.01% to 0.5%; chlorhexidine, 0.005% to 0.01%; chlorobutanol, up to 0.5%; and stabilized oxychloro complex (Purite®) 0.001% to 0.5%.

In another embodiment, the topical formulations of this invention do not include a preservative. Such formulations would be useful for patients who wear contact lenses, or those who use several topical ophthalmic drops and/or those with an already compromised ocular surface (e.g. dry eye) wherein limiting exposure to a preservative may be more desirable.

Viscosity Enhancing Agents and Demulcents

In certain embodiments, viscosity enhancing agents may be added to the cetirizine formulations of the invention. Examples of such agents include polysaccharides, such as hyaluronic acid and its salts, chondroitin sulfate and its salts, dextrans, various polymers of the cellulose family, vinyl polymers, and acrylic acid polymers.

In certain embodiments, the cetirizine formulations of the invention comprise ophthalmic demulcents and/or viscosity enhancing polymers selected from one or more of the following: cellulose derivatives such as carboxymethycellulose (0.01 to 5%) hydroxyethylcellulose (0.01% to 5%), hydroxypropyl methylcellulose or hypromellose (0.01% to 5%), and methylcelluose (0.02% to 5%); dextran 40/70 (0.01% to 1%); gelatin (0.01% to 0.1%); polyols such as glycerin (0.01% to 5%), polyethylene glycol 300 (0.02% to 5%), polyethylene glycol 400 (0.02% to 5%), polysorbate 80 (0.02% to 3%), propylene glycol (0.02% to 3%), polyvinyl alcohol (0.02% to 5%), and povidone (0.02% to 3%); hyaluronic acid (0.01% to 2%); and chondroitin sulfate (0.01% to 2%).

Viscosity of the stable ophthalmic cetirizine formulations of the invention may be measured according to standard methods known in the art, such as use of a viscometer or rheometer. One of ordinary skill in the art will recognize that factors such as temperature and shear rate may effect viscosity measurement. In a particular embodiment, viscosity of the is measured at 20° C.+/−1° C. using a Brookfield Cone and Plate Viscometer Model VDV-III Ultra+ with a CP40 or equivalent Spindle with a shear rate of approximately 22.50+/−approximately 10 (1/sec), or a Brookfield Viscometer Model LVDV-E with a SC4-18 or equivalent Spindle with a shear rate of approximately 26+/−approximately 10 (1/sec). In another embodiment, viscosity of the ophthalmic formulations of the invention is measured at 25° C.+/−1° C. using a Brookfield Cone and Plate Viscometer Model VDV-III Ultra+ with a CP40 or equivalent Spindle with a shear rate of approximately 22.50+/−approximately 10 (1/sec), or a Brookfield Viscometer Model LVDV-E with a SC4-18 or equivalent Spindle with a shear rate of approximately 26+/−approximately 10 (1/sec).

Tonicity Enhancers

Tonicity is adjusted if needed typically by tonicity enhancing agents. Such agents may, for example be of ionic and/or non-ionic type. Examples of ionic tonicity enhancers are alkali metal or earth metal halides, such as, for example, $CaCl_2$, KBr, KCl, LiCl, NaI, NaBr or NaCl, $Na_2SO_4$ or boric acid. Non-ionic tonicity enhancing agents are, for example, urea, glycerol, sorbitol, mannitol, propylene glycol, or dextrose. The aqueous solutions of the present invention are typically adjusted with tonicity agents to approximate the osmotic pressure of normal lachrymal fluids which is equivalent to a 0.9% solution of sodium chloride or a 2.5% solution of glycerol. An osmolality of about 225 to 400 mOsm/kg is preferred, more preferably 280 to 320 mOsm.

Solubilizing Agents

The topical formulation may additionally require the presence of a solubilizer, in particular if one or more of the ingredients tends to form a suspension or an emulsion. Suitable solubilizers include, for example, tyloxapol, fatty acid glycerol polyethylene glycol esters, fatty acid polyethylene glycol esters, polyethylene glycols, glycerol ethers, polysorbate 20, polysorbate 80 or mixtures of those compounds. In a preferred embodiment, the solubilizer is a reaction product of castor oil and ethylene oxide, for example the commercial products Cremophor EL® or Cremophor RH40®. Reaction products of castor oil and ethylene oxide have proved to be particularly good solubilizers that are tolerated extremely well by the eye. In another embodiment, the solubilizer is tyloxapol or a cyclodextrin. The concentration used depends especially on the concentration of the active ingredient. The amount added is typically sufficient to solubilize the active ingredient. For example, the concentration of the solubilizer is from 0.1 to 5000 times the concentration of the active ingredient. Preferably, the solubilizer is not a cyclodextrin compound (for example alpha-, beta- or gamma-cyclodextrin, e.g. alkylated, hydroxyalkylated, carboxyalkylated or alkyloxycarbonyl-alkylated derivatives, or mono- or diglycosyl-alpha-, beta- or gamma-cyclodextrin, mono- or dimaltosyl-alpha-, beta- or gamma-cyclodextrin or panosyl-cyclodextrin).

Examples of Formulations

In a preferred embodiment, the cetirizine formulation comprises cetirizine at 0.05% to 0.25% (w/v), glycerin at 0.1% to 5% (v/v) (e.g., 0.1% to 3% (v/v) or any specific value within said range), and water. In particular embodiments the cetirizine formulation of the invention does not contain a cyclodextrin or other solubilizing compound. Optionally, the formulation also comprises a preservative such as benzalkonium chloride at 0.005% to 0.02% (w/v) or its derivative (e.g., Polyquad®), or a stabilized oxychloro complex such as Purite®. In a particular embodiment, the cetirizine formulation comprises cetirizine at 0.1% (w/v), glycerin at 1.2% to 3% (v/v), and water. In another particular embodiment, the cetirizine 0.1% (w/v), glycerin 1.2% to 3% (v/v), and water formulation also comprises benzalkonium chloride at 0.01% (w/v) or a stabilized, oxychloro complex (e.g., Purite®). The pH of the formulation is between 5.0 and 7.5. for example, the pH of the formulation is 5, 5.5, 6.0, 6.5 or 7.0.

In a specific embodiment, the cetirizine formulation comprises cetirizine at 0.1% (w/v), glycerin at 2.125% (v/v), benzalknoium chloride at 0.01% (w/v), q.s. with water. In one embodiment, the cetirizine formulation comprises cetirizine as the only active ingredient at 0.05% to 0.25% (w/v) and optionally one or more tear substitutes or a mucoadhesive, polymeric compound (e.g., Durasite®). Preferably, the cetirizine formulations do not contain a cyclodextrin or other solubilizing compound.

Where the formulation comprises one or more tear substitutes, the tear substitute preferably contains hydroxypropylmethyl cellulose or carboxymethyl cellulose or both. In some embodiments, the hydroxypropylmethyl cellulose or carboxymethyl cellulose is present at a concentration of 0.5% to 1% (w/v) (or any specific value within said range) and the resulting viscosity of the solution is 60-80 cpi. In a particular embodiment, the hydroxypropylmethyl cellulose or carboxymethyl cellulose is present at a concentration of 0.7% to 0.9%. In another particular embodiment, the hydroxypropylmethyl cellulose or carboxymethyl cellulose is present at a concentration of 0.1% to 0.7% and the resulting viscosity of the solution is 10-30 cpi. Optionally, the formulation also comprises a preservative, preferably benzalkonium chloride at a concentration of from 0.005% to 0.02% (w/v) (or any specific value within said range) or its derivative (e.g., Polyquad®), or a stabilized oxychloro complex (e.g., Purite®). The pH of the formulation is between 5.0 and 7.5. For example, the pH of the formulation is 5, 5.5, 6.0, 6.5 or 7.0.

In another preferred embodiment, the cetirizine formulation comprises cetirizine at 0.05% to 0.25% (w/v), naphazoline at 0.01% to 0.2% (w/v), glycerin at 0.1% to 5% (v/v) (e.g., 0.1% to 3% (v/v) or any specific value within said range), and water. Preferably, the cetirizine/naphazoline formulation does not contain a cyclodextrin or other solubilizing compound. Optionally, the formulation also comprises benzalkonium chloride at 0.005% to 0.02% (w/v) or its derivative (e.g., Polyquad®), or a stabilized oxychloro complex such as Purite®. In a particular embodiment, the cetirizine formulation comprises cetirizine at 0.1% (w/v), naphazoline at 0.09% (w/v), glycerin at 1.2% to 3% (v/v), and water. In another particular embodiment, the cetirizine 0.1% (w/v), naphazoline 0.09% (w/v), glycerin at 1.2% to 3% (v/v), and water formulation also comprises benzalkonium chloride at 0.01% (w/v) or a stabilized oxychloro complex such as Purite®. The pH of the formulation is between 5.0 and 7.5. For example, the pH of the formulation is 5, 5.5, 6.0, 6.5 or 7.0.

In yet another preferred embodiment, the cetirizine formulation comprises cetirizine at 0.05% to 0.25% (w/v), naphazoline at 0.01% to 0.2% (w/v), and one or more tear substitutes or a mucoadhesive polymeric compound (e.g., Durasite®). In particular embodiments the cetirizine formulation does not contain a cyclodextrin or other solubilizing compound. Where the formulation comprises one or more tear substitutes, the tear substitute preferably contains hydroxypropylmethyl cellulose or carboxymethyl cellulose, or both. In some embodiments, the hydroxypropylmethyl cellulose or carboxymethyl cellulose is present at a concentration of 0.5% to 1% (w/v) (or any specific value within said range) and the resulting viscosity of the solution is 60-80 cpi. In a particular embodiment, the hydroxypropylmethyl cellulose or carboxymethyl cellulose is present at a concentration of 0.7% to 0.9%. Optionally, the formulation also comprises a preservative, preferably benzalkonium chloride at a concentration of from 0.005% to 0.02% (w/v) (or any specific value within said range) or stabilised oxychloro complex (Purite®). The pH of the formulation is between 5.0 and 7.5. For example, the pH of the formulation is 5, 5.5, 6.0, 6.5 or 7.0.

In yet another preferred embodiment, the cetirizine formulation comprises cetirizine at 0.05% to 0.25% (w/v), oxymetazoline at 0.01% to 0.1% (w/v), glycerin at 0.1% to 5% (v/v) (e.g., 0.1% to 3% (v/v) or any specific value within said range), and water. Preferably, the cetirizine/oxymetazoline formulation does not contain a cyclodextrin or other solubilizing compound. Optionally, the formulation also comprises benzalkonium chloride at 0.005% to 0.02% (w/v) or its derivative (e.g., Polyquad®), or a stabilized, oxychloro complex (e.g., Purite®). In a particular embodiment, the cetirizine formulation comprises cetirizine at 0.1% (w/v), oxymetazoline at 0.05% (w/v), glycerin at 1.2% to 3% (v/v), and water. In another particular embodiment, the cetirizine 0.1% (w/v), oxymetazoline 0.05% (w/v), glycerin 1.2% to 3% (v/v), and water formulation also comprises benzalkonium chloride at 0.01% (w/v) or a stabilized, oxychloro complex (e.g., Purite®). In certain embodiments, the pH of the formulation is between 5.0 and 7.5. For example, the pH of the formulation is 5, 5.5, 6.0, 6.5 or 7.0.

In still another preferred embodiment, the cetirizine formulation comprises cetirizine at 0.05% to 0.25% (w/v), oxymetazoline at 0.01% to 0.1% (w/v), and one or more tear substitutes or a mucoadhesive, polymeric compound (e.g., Durasite®). Preferably, the cetirizine/oxymetazoline formulation does not contain a cyclodextrin or other solubilizing compound. Where the formulation comprises one or more tear substitutes, the tear substitute preferably contains hydroxypropylmethyl cellulose or carboxymethyl cellulose or both. In some embodiments, the hydroxypropylmethyl cellulose or carboxymethyl cellulose is present at a concentration of 0.5% to 1% (w/v) (or any specific value within said range) and the resulting viscosity of the solution is 60-80 cpi. In a particular embodiment, the hydroxypropylmethyl cellulose or carboxymethyl cellulose is present at a concentration of 0.7% to 0.9%. Optionally, the formulation also comprises a preservative, preferably benzalkonium chloride at a concentration of from 0.005% to 0.02% (w/v) (or any specific value within said range) or a stabilized oxychloro complex)(Purite®). The pH of the formulation is between 5.0 and 7.5. For example, the pH of the formulation is 5, 5.5, 6.0, 6.5 or 7.0.

In still another preferred embodiment, the cetirizine formulation comprises cetirizine at 0.05% to 0.5% (w/v), fluticasone at 0.001% to 1.0% (w/v), glycerin at 0.1% to 5% (v/v) (e.g., 0.1% to 3% (v/v) or any specific value within said range), and water. Preferably, the cetirizine/fluticasone formulation does not contain a cyclodextrin or other solubilizing compound. Optionally, the formulation also comprises benzalkonium chloride at 0.005% to 0.02% (w/v) or its derivative (e.g., Polyquad®), or a stabilized, oxychloro complex (e.g., Purite®). In a particular embodiment, the cetirizine formulation comprises cetirizine at 0.1% (w/v), fluticasone at 0.005%, glycerin at 1.2% to 3% (v/v), and water. In another particular embodiment, the cetirizine formulation comprises cetirizine at 0.25% (w/v), fluticasone at 0.01% (w/v), glycerin at 1.2% to 3% (v/v), and water. Optionally, the cetirizine/fluticasone formulations also comprises benzalkonium chloride at 0.01% (w/v) or a stabilized, oxychloro complex (e.g., Purite®). The pH of the formulation is between 5.0 and 7.5. For example, the pH of the formulation is 5, 5.5, 6.0, 6.5 or 7.0.

In yet another preferred embodiment, the cetirizine formulation comprises cetirizine at 0.05% to 0.5% (w/v), fluticasone at 0.001% to 1.0% (w/v), preferably fluticasone 0.005%, and one or more tear substitutes or a mucoadhesive, polymeric compound (e.g., Durasite®). Preferably, the cetirizine/fluticasone formulation does not contain a cyclodextrin or other solubilizing compound. Where the formulation comprises one or more tear substitutes, the tear substitute preferably contains hydroxypropylmethyl cellulose or carboxymethyl cellulose or both. In some embodiments, the hydroxypropylmethyl cellulose or carboxymethyl cellulose is present at a concentration of 0.5% to 1% (w/v) (or any specific value within said range) and the resulting viscosity of the solution is 60-80 cpi. In a particular embodiment, the hydroxypropylmethyl cellulose or carboxymethyl cellulose is present at a concentration of 0.7% to 0.9%. Optionally, the formulation also comprises a preservative, preferably benzalkonium chloride at a concentration of from 0.005% to 0.02% (w/v) (or any specific value within said range) or stabilized oxychloro complex (Purite®). The pH of the formulation is between 5.0 and 7.5. For example, the pH of the formulation is 5, 5.5, 6.0, 6.5 or 7.0.

In still another preferred embodiment, the cetirizine formulation comprises 0.1% cetirizine, 0.005% fluticasone, 1% Polyethylene Glycol 400, NF, 0.2% Dibasic Sodium Phosphate, Anhydrous, USP, 0.25% Hypromellose, USP, 0.1% Polysorbate 80, NF, 1.8% Glycerin, USP, 0.025% Edetate Disodium, USP, and 0.01% Benzalkonium Chloride, NF (pH 7.0).

In yet another preferred embodiment, the cetirizine formulation comprises 0.25% cetirizine, 0.01% fluticasone, 1% Polyethylene Glycol 400, NF, 0.2% Dibasic Sodium Phosphate, Anhydrous, USP, 0.25% Hypromellose, USP; 0.1% Polysorbate 80, NF, 1.2% Glycerin, USP, 0.025% Edetate Disodium, USP, and 0.01% Benzalkonium Chloride, NF (pH 7.0).

The formulations of the present invention provide for the chemical stability of the formulated cetirizine and other optional active agents (e.g., napahzoline, oxymetazoline, fluticasone, or combinations thereof) of the formulation, without the use of a cyclodextrin or other solubilizing compound. "Stability" and "stable" in this context refers to the resistance of the cetirizine and other optional active agents to chemical degradation under given manufacturing, preparation, transportation and storage conditions. The "stable" formulations of the invention also preferably retain at least 90%, 95%, 98%, 99%, or 99.5% of a starting or reference amount under given manufacturing, preparation, transportation, and/or storage conditions. The amount of cetirizine and other optional active agents can be determined using any art-recognized method, for example, as UV-Vis spectrophotometry and high pressure liquid chromatography (HPLC).

In certain embodiments, the cetirizine formulations are stable at temperatures ranging from about 20 to 30° C. for at least 1 week, at least 2 weeks, at least 3 weeks, at least 4 weeks, at least 5 weeks, at least 6 weeks, or at least 7 weeks. In other embodiments, the cetirizine formulations are stable at temperatures ranging from about 20 to 30° C. for at least 1 month, at least 2 months, at least 3 months, at least 4 months, at least 5 months, at least 6 months, at least 7 months, at least 8 months, at least 9 months, at least 10 months, at least 11 months, or at least 12 months. In one embodiment, the formulation is stable for at least 3 months at 20-25° C.

In other embodiments, the cetirizine formulations are stable at temperatures ranging from about 2 to 8° C. for at least 1 month, at least 2 months, at least 4 months, at least 6 months, at least 8 months, at least 10 months, at least 12 months, at least 14 months, at least 16 months, at least 18 months, at least 20 months, at least 22 months, or at least 24 months. In one embodiment, the formulation is stable for at least 2 months at 2 to 8° C.

In other embodiments, the cetirizine formulations are stable at temperatures of about –20° C. for at least 1 month, at least 2 months, at least 4 months, at least 6 months, at least 8 months, at least 10 months, at least 12 months, at least 14 months, at least 16 months, at least 18 months, at least 20 months, at least 22 months, or at least 24 months. In one embodiment, the formulation is stable for at least 6-12 months at –20° C.

In a particular embodiment, a cetirizine formulation of the invention is stable at temperatures of about 20-30° C. at concentrations up to 0.10% for at least 3 months. In another embodiment, the formulation is stable at temperatures from about 2-8° C. at concentrations up to 0.10% for at least 6 months.

Methods of Use

The cetirizine formulations of the invention are useful for the treatment and prevention of the signs and symptoms of both the acute phase (i.e., seasonal) and late phase inflammatory reactions (i.e., chronic, persistent or refractory) of allergic conjunctivitis, such as ocular itching, redness, and eyelid swelling, as well as associated nasal symptoms. The formulations of the invention are also useful for the treatment and prevention of the signs and symptoms of allergic rhinoconjunctivitis, such as itchy, running nose, sneezing, nasal/sinus congestion, and red, watery and/or itchy eyes.

The invention provides methods of treating or preventing allergic conjunctivitis and/or allergic rhinoconjunctivitis in a subject in need thereof comprising topically administering to the eye surface of the subject a an ophthalmic formulation comprising an effective amount of cetirizine. In certain embodiments, the administration of cetirizine to the eye of a subject in need of treatment or prevention of allergic conjunctivitis and/or rhinoconjunctivitis is also effective to mitigate or reduce one or more nasal symptoms associated with the either allergy (e.g., itchy, running nose, sneezing and/or nasal/sinus congestion). Topical administration of the ophthalmic formulations directly to the eye of a subject will significantly reduce nasal signs and symptoms via drainage from the ocular surface into the nasal cavity through the nasolacrimal duct (See e.g., Abelson et al., Clin. Ther. 25(3), 931-947 (2003); Spangler et al., Clin. Ther. 25(8), 2245-2267 (2003); and Crampton et al., Clin Ther. November; 24(11): 1800-8 (2002). Furthermore, significantly less active agent is required to treat the nasal symptoms when instilled through the eye of a subject as compared to administration through the nose of the subject. For example, each spray of Flonase® (commercially available nasal spray comprising fluticasone) delivers 50 micrograms of fluticasone to the nasal cavity to treat allergic rhinitis and allergic rhinoconjunctivitis. In contrast, one drop of a 0.005% fluticasone ophthalmic formulation (i.e., 2.5 micrograms in a 500 microliter drop) has been shown to significantly reduce nasal symptoms associated with ocular allergy when topically administered directly to the eye (see Example 2 herein). As such, the methods of the present invention are more effective than the currently available treatment options for nasal symptoms of allergic conjunctivitis and allergic rhinoconjunctivitis.

The subject is preferably a human, but may be another mammal, for example a dog, a cat, a horse, a rabbit, a mouse, a rat, or a non-human primate.

The formulations of the present invention contain an amount of cetirizine, and optionally one or more additional active ingredients (for example without limitation a vasoconstrictor such as naphazoline or oxymetazoline, or a steroid such as fluticasone), that is effective for the intended use (i.e., to mitigate the signs and symptoms of allergic conjunctivitis and/or rhinoconjunctivitis). In certain embodiments, once a day administration of the formulations of the present invention is effective to mitigate the symptoms of allergic conjunctivitis and/or rhinoconjunctivitis. However, particular dosages are also selected based on a number of factors including the age, sex, species and condition of the subject. Effective amounts can also be extrapolated from dose-response curves derived from in vitro test systems or from animal models. The term "effective amount" means an amount of cetirizine that is sufficient to eliminate or reduce a symptom of allergic conjunctivitis and/or rhinoconjunctivitis. In certain embodiments, the effective amount is the amount sufficient for the treatment or prevention of allergic conjunctivitis and/or rhinoconjunctivitis. "Treatment" in this context refers to reducing or ameliorating at least one symptom of allergic conjunctivitis and/or rhinoconjunctivitis. "Prevention" in this context refers to a reduction in the frequency of, or a delay in the onset of, symptoms associated with allergic conjunctivitis and/or rhinoconjunctivitis, relative to a subject who does not receive the composition. The effective amount of cetirizine and other active agents in the formulation will depend on absorption, inactivation, and excretion rates of the drug as well as the delivery rate of the compound from the formulation. Particular dosages may also vary with the severity of the condition to be alleviated. It is to be further understood that for any particular subject, specific dosage regimens should be adjusted over time according to the individual need and the professional judgment of the person administering or supervising the administration of the compositions. Typically, a dosing regiment will be determined using techniques known to one skilled in the art.

Examples of dosing regimens that can be used in the methods of the invention include, but are not limited to, once daily, twice daily, three times, and four times daily. In certain embodiments, the method comprises administering a cetirizine formulation of the invention to the eye of the subject once a day. In some embodiments, the administration is 2 to 4 times a day.

In certain embodiments, once a day administration (q.d.) is effective to mitigate the symptoms of ocular and/or nasal allergy. However, particular dosages may also selected based on a number of factors including the age, sex, species and condition of the subject. Effective amounts can also be extrapolated from dose-response curves derived from in vitro test systems or from animal models.

The combined use of several active agents formulated into the compositions of the present invention may reduce the required dosage for any individual component because the onset and duration of effect of the different components may be complimentary. In such combined therapy, the different active agents may be delivered together or separately, and simultaneously or at different times within the day.

In a particular embodiment, a formulation comprising cetirizine as the only active agent in the formulation is administered to the eye of a subject in need of treatment or prevention of an allergic conjunctivitis and/or rhinoconjunctivitis once daily (q.d.). In certain embodiments, the combination formulation is administered two to four times a day.

In another particular embodiment, cetirizine is formulated with one or more of naphazoline, oxymetazoline or fluticasone, and administered to the eye of a subject in need of treatment or prevention of allergic conjunctivitis and/or rhinoconjunctivitis once daily (q.d.). In certain embodiments, the combination formulation is administered two to four times a day.

In a preferred embodiment, cetirizine is formulated with fluticasone and administered to the eyed of a subject in need of treatment or prevention of allergic conjunctivitis and/or rhinoconjunctivitis. Surprisingly the combination formulations of cetirizine and fluticasone as described herein were more effective at relieving itching than could be predicted from the efficacy of each component individually. Even more surprising was the finding that lower doses of cetirizine and fluticasone were more effective at relieving ocular itching and associated nasal symptoms of allergic conjunctivitis than higher doses of the individual components alone, or in combination. For example, as described in the Examples, a 0.1% cetirizine/0.005% fluticasone formulation (low dose) was more efficacious than 0.25% cetirizine/0.01% fluticasone formulation (high dose). Similarly, in a clinical study described herein, the efficacy of 0.005% fluticasone was more efficacious than the higher dose 0.01% fluticasone.

Packaging

The formulations of the present invention may be packaged as either a single dose product or a multi-dose product. The single dose product is sterile prior to opening of the package and all of the composition in the package is intended to be consumed in a single application to one or both eyes of a patient. The use of an antimicrobial preservative to maintain the sterility of the composition after the package is opened is generally unnecessary.

Multi-dose products are also sterile prior to opening of the package. However, because the container for the composition may be opened many times before all of the composition in the container is consumed, the multi-dose products must have sufficient antimicrobial activity to ensure that the compositions will not become contaminated by microbes as a result of the repeated opening and handling of the container. The level of antimicrobial activity required for this purpose is well known to those skilled in the art, and is specified in official publications, such as the United States Pharmacopoeia ("USP") and corresponding publications in other countries. Detailed descriptions of the specifications for preservation of ophthalmic pharmaceutical products against microbial contamination and the procedures for evaluating the preservative efficacy of specific formulations are provided in those publications. In the United States, preservative efficacy standards are generally referred to as the "USP PET" requirements. (The acronym "PET" stands for "preservative efficacy testing.")

The use of a single dose packaging arrangement eliminates the need for an antimicrobial preservative in the compositions, which is a significant advantage from a medical perspective, because conventional antimicrobial agents utilized to preserve ophthalmic compositions (e.g., benzalkonium chloride) may cause ocular irritation, particularly in patients suffering from dry eye conditions or pre-existing ocular irritation. However, the single dose packaging arrangements currently available, such as small volume plastic vials prepared by means of a process known as "form, fill and seal", have several disadvantages for manufacturers and consumers. The principal disadvantages of the single dose packaging systems are the much larger quantities of packaging materials required, which is both wasteful and costly, and the inconvenience for the consumer. Also, there is a risk that consumers will not discard the single dose containers following application of one or two drops to the eyes, as they are instructed to do, but instead will save the opened container and any composition remaining therein for later use. This improper use of single dose products creates a risk of microbial contamination of the single dose product and an associated risk of ocular infection if a contaminated composition is applied to the eyes.

While the formulations of this invention are preferably formulated as "ready for use" aqueous solutions, alternative formulations are contemplated within the scope of this invention. Thus, for example, the active ingredients, surfactants, salts, chelating agents, or other components of the ophthalmic solution, or mixtures thereof, can be lyophilized or otherwise provided as a dried powder or tablet ready for dissolution (e.g., in deionized, or distilled) water. Because of the self-preserving nature of the solution, sterile water is not required.

Kits

The present invention provides a pharmaceutical pack or kit comprising one or more containers filled with a liquid or lyophilized cetirizine formulation of the invention (i.e., a formulation comprising cetirizine alone or in combination with an additional active agent as described herein). In one embodiment, the formulation is an aqueous formulation of cetirizine. In one embodiment, the formulation is lyophilized. In preferred embodiments the liquid or lyophilized formulation is sterile. In one embodiment, the kit comprises a liquid or lyophilized formulation of the invention, in one or more containers, and one or more other prophylactic or therapeutic agents (e.g., cetirizine in combination with an additional active agent such as fluticasone, oxymetazoline or naphazoline) useful for the treatment of allergic conjunctivitis and/or allergic rhinoconjunctivitis. The one or more other prophylactic or therapeutic agents may be in the same container as the cetirizine or in one or more other containers. Preferably, the cetirizine is formulated at a concentration of from about 0.05% (w/v) to about 1.0% (w/v) and is suitable for topical ocular administration. In certain embodiments, cetirizine is formulated with an additional active agents such as fluticasone, oxymetazoline or naphazoline, as described herein. In certain embodiments, the kit contains the cetirizine in unit dosage form.

In certain embodiments, the kit further comprises instructions for use in the treatment of allergic conjunctivitis and/or allergic rhinoconjunctivitis (e.g., using the cetirizine formulations of the invention alone or in combination with another prophylactic or therapeutic agent), as well as side effects and dosage information for one or more routes of administration. Optionally associated with such container(s) is a notice in the form prescribed by a governmental agency regulating the manufacture, use or sale of pharmaceuticals or biological products, which notice reflects approval by the agency of manufacture, use or sale for human administration. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g. CD ROM), and the like. Such media may include addresses to internet sites that provide such instructional materials.

In another embodiment, this invention provides kits for the packaging and/or storage and/or use of the formulations described herein, as well as kits for the practice of the methods described herein. The kits can be designed to facilitate one or more aspects of shipping, use, and storage.

All publications and patents mentioned herein are hereby incorporated by reference in their entirety as if each individual publication or patent was specifically and individually indicated to be incorporated by reference.

EXAMPLES

The invention is further defined by reference to the following examples, which are not meant to limit the scope of the present invention. It will be apparent to those skilled in the art that many modifications, both to the materials and methods, may be practiced without departing from the purpose and interest of the invention.

Example 1

Cetirizine (0.1%) Prevents Ocular Itching Associated with Allergic Conjunctivitis A placebo controlled, double-blind study was conducted to evaluate the efficacy of cetirizine 0.1% (N=15) compared to vehicle (N=16). Subjects underwent 2 screening visits (an allergen titration and confirmation) followed by a drug evaluation visit. At the drug evaluation visit, one drop of masked study medication was instilled in each eye and comfort assessments were taken. Sixteen hours later the subjects were challenged with allergen and allergic assessments were taken. The results are presented in Tables 1 and 2 and in FIGS. 1-2. The ocular itching score ranges from 0, no itching, to 4, severe itching. The comfort score ranges from 0, very comfortable, to 10, very uncomfortable (Note: The most uncomfortable commercially available allergy drop=4). The results demonstrate that a single drop of cetirizine (0.1%) ophthalmic solution (q.d.) was effective to prevent ocular itching associated with allergic conjunctivitis when administered 16 hours prior to conjunctival allergen challenge (CAC), but had little effect on reducing conjunctival redness (FIGS. 1A and 1B). Differences between cetirizine and vehicle groups were both clinically (≥1 unit difference) and statistically significant (P<0.05). In addition, as shown in Table 2, and FIG. 2, the cetirizine formulation was comfortable (i.e., well-tolerated) by the subjects.

TABLE 1

Mean Ocular Itching Scores (0-4 scale) following CAC 16 hrs after dosing

| Statistic | Timepoint | Cetirizine 0.1% HCl (N = 15) | Vehicle (N = 16) | Mean Difference (cetirizine − vehicle) | p-value |
|---|---|---|---|---|---|
| Mean (SD) | Pre-CAC | 0.00 (0.00) | 0.00 (0.00) | 0.00 | 1.0000 |
|  | 3 min | 1.67 (1.12) | 2.36 (0.58) | −0.69 | 0.0191 |
|  | 5 min | 1.52 (1.12) | 2.56 (0.60) | −1.04 | 0.0051 |
|  | 7 min | 1.45 (1.02) | 2.47 (0.72) | −1.02 | 0.0031 |

TABLE 2

Mean Drop Comfort Scores (0-10 scale)

| Statistic | Timepoint | Cetirizine 0.1% HCl (N = 15) | Vehicle (N = 16) | Mean Difference (cetirizine − vehicle) | p-value |
|---|---|---|---|---|---|
| Mean (SD) | Upon Instillation | 0.47 (0.68) | 0.72 (1.49) | −0.25 | 0.3908 |
|  | 1 min | 0.37 (0.49) | 0.84 (1.80) | −0.47 | 0.1572 |
|  | 2 min | 0.47 (0.63) | 0.81 (1.53) | −0.34 | 0.2467 |
|  | 5 min | 0.20 (0.41) | 0.13 (0.34) | 0.07 | 0.5981 |
|  | 10 min | 0.27 (0.46) | 0.31 (0.70) | −0.04 | 0.7864 |

Example 2

Fluticasone Prevents Ocular and Nasal Symptoms Associated with Allergic Conjunctivitis A placebo controlled, double-blind study was conducted to evaluate the efficacy of Fluticasone 0.001% (N=16), Fluticasone 0.005% (N=16), Fluticasone 0.01% (N=15) compared to vehicle alone (N=15). Subjects underwent 2 screening visits (allergen titration and confirmation) followed by 2 drug evaluation visits, as indicated in the study design shown in FIGS. 3A and 3B. At the drug evaluation visits, one drop of masked study medication was instilled in each eye and ocular allergic assessments were taken. Eight hours later the subjects were challenged with allergen and primary and secondary ocular and nasal endpoints were assessed, as well as safety of the formulations. The results are presented in FIGS. 4-23.

Primary Ocular Endpoints

Ocular itching, conjunctival redness, lid swelling, and nasal congestion were assessed in each subject during visit 4B.

Ocular itching was subjectively assessed on a scale of 0 (no itching) to 4 (severe itching). As shown in FIG. 4, Fluticasone 0.001%, 0.005% and 0.01% were about equally effective in reducing ocular itching over a 7 minute time period as compared to vehicle alone.

Conjunctival redness was also subjectively assessed on a scale of 0 (no redness) to 4 (severe redness). As shown in FIG. 5, Fluticasone 0.001%, 0.005% and 0.01% were about equally effective in reducing conjunctival redness over a 20 minute period as compared to vehicle alone.

Lid swelling was subjectively assessed on a scale of 0 (no lid swelling) to 3 (severe lid swelling). As shown in FIG. 6, Fluticasone 0.001% and 0.005% were each more effective than Fluticasone 0.01% at reducing lid swelling over a 20 minute period as compared to vehicle alone.

Nasal Congestion was subjectively assessed on a scale of 0 (no congestion) to 4 (severe congestion). As shown in FIG. 7, Fluticasone 0.001%, 0.005% and 0.01% were about equally effective in reducing nasal congestion over a 30 minute period as compared to vehicle alone.

A summary of the results of the primary ocular endpoint assessments is shown in FIG. 8. As shown in FIG. 8, the reduction in conjunctival redness by Fluticasone 0.005% and 0.01% and the reduction in lid swelling by Fluticasone 0.001% were each statistically significant (p<0.05).

Secondary Ocular Endpoints

Ciliary Redness, episcleral redness, chemosis and watery eyes were assessed in each subject at visit 4B.

Ciliary redness was assessed on a scale of 0 (no redness) to 4 (severe redness). As shown in FIG. 9, Fluticasone 0.001%, 0.005% and 0.01% were each significantly effective in reducing ciliary redness over a 20 minute period as compared to vehicle alone (p<0.05 for each Fluticasone concentration).

Episcleral redness was assessed on a scale of 0 (no redness) to 4 (severe redness). As shown in FIG. 10, Fluticasone 0.001%, 0.005% and 0.01% each reduce episcleral redness over a 20 minute period as compared to vehicle alone.

Chemosis was assessed on a scale of 0 (none) to 4 (extreme). As shown in FIG. 11, Fluticasone 0.001%, 0.005% and 0.01% were each significantly effective in reducing chemosis over a 20 minute period.

Watery eyes were also subjectively assessed on a scale of 0 (not watery) to 4 (extremely watery). As shown in FIG. 12, Fluticasone 0.001% and 0.05% were each more effective than Fluticasone 0.01% in reducing watery eyes over a 20 minute period, as compared to vehicle alone.

A summary of the secondary ocular endpoints assessed is shown in FIG. 13. As shown in FIG. 13, the reduction in ciliary redness by all three concentrations of Fluticasone, the reduction in episcleral redness by Fluticasone 0.005%, and the reduction of watery eyes by Fluticasone 0.05% were each statistically significant ($p<0.05$).

Secondary Nasal Endpoints

Rhinorrhea, ear or palate pruritis, nasal pruritis were assessed in each subject at visit 4B using a scale of 0 (none) to 4 (extreme) for each endpoint.

As shown in FIGS. 14 and 16, Fluticasone 0.001%, 0.005% and 0.01% each had a clinically significant effect in reducing rhinorrhea and nasal pruritis, respectively, over a 20 minute period as compared to vehicle alone. Shown in FIG. 15, Fluticasone 0.001%, 0.005% and 0.01% were each had an effect in reducing ear and palate pruritis as compared to vehicle alone.

Total nasal scores were assessed on a scale of 0-16. As shown in FIG. 17, Fluticasone 0.001%, 0.005% and 0.01%, each surprisingly had a clinically significant effect on total nasal score when administered directly to the eye of each subject. A summary of the nasal endpoints assessed is shown in FIGS. 18 and 19.

Safety

Intraocular pressure, drop comfort and adverse events such as blurry vision, conjunctival hemorrhage, dry eye, site pain and/or irritation and headache, were assessed for each subject.

Drop comfort was subjectively assessed on a scale of 0 (extremely comfortable) to 10 (extremely uncomfortable) during visit 2 and visit 3. As shown in FIGS. 20 and 21, Fluticasone 0.01 was highly uncomfortable upon instillation as compared to Fluticasone 0.001% and 0.005%, and as compared to vehicle alone. The comfort of Fluticasone 0.001% and 0.005% were comparable to the comfort of the vehicle control.

A summary of the total percentage of subjects who experienced adverse events such as blurry vision, conjunctival hemorrhage, dry eye, site pain and/or irritation, and headache, is shown in FIG. 22.

The effect of each concentration of Fluticasone on intraocular pressure (IOP) as compared to vehicle alone is shown in FIG. 23.

The results demonstrate that a single drop of either Fluticasone 0.001%, 0.005% or 0.01% was effective to prevent both ocular and nasal symptoms associated with allergic conjunctivitis. However, when taking all primary and secondary endpoints into consideration, Fluticasone 0.005% was the most efficacious in relieving both ocular and nasal symptoms, and was shown to be more comfortable than Fluticasone 0.001% and Fluticasone 0.01%, with no adverse effect on intraocular pressure.

Example 3

An Evaluation of the Effects of Topical Cetirizine/Fluticasone Ophthalmic Formulations on the Signs of Allergic Conjunctivitis Using the Murine Model of Ragweed-Induced Active Anaphylaxis Seasonal allergic conjunctivitis (hay fever conjunctivitis) develops in a subset of atopic individuals (those with a genetic disposition of hypersensitivity to allergens). The signs and symptoms of the condition are elicited by airborne allergens (e.g. ragweed, tree and grass pollens, animal dander). Seasonal allergic conjunctivitis is the most common form of ocular allergic disease and may account for up to 90% of allergic disorders seen.

The most common and distressing ocular signs and symptoms associated with allergic conjunctivitis are itching and redness. Swelling, mucous discharge and excessive tearing are frequently involved. In allergic conjunctivitis, airborne allergens presumably dissolve in the tear film, traverse the conjunctiva, and then bind with IgE antibodies attached to the surface of the conjunctival mast cell to trigger an allergic response. This attachment results in mast cell degranulation and release of chemical mediators that lead to signs and symptoms of allergic disease. Some of these substances, e.g. histamines and prostaglandins, directly affect blood vessels and nerves, whereas others influence the migration of inflammatory cells such as neutrophils, eosinophils and macrophages, causing inflammation.

The major chemical mediator involved in producing ocular symptoms is histamine. Several types of histamine have been identified in the human conjunctiva. Stimulation of H1 receptors results mainly in itching while stimulation of H2 receptors results largely in vasodilation (redness). However, studies with antihistamines known to be highly specific for H1 receptors have suggested that H1 receptors may also have a secondary effect on redness.

The purpose of this study was to investigate the potential of cetirizine/fluticasone combination formulations in preventing signs of allergic conjunctivitis in a murine active anaphylaxis model. In this model, mice are systemically sensitized to short ragweed allergen (SRW) and then challenged by instilling SRW in the eyes. Therapeutic treatment is given after sensitization but prior to topical challenge. Allergens present in the SRW preparation cross-link IgE antibodies bound to conjunctival mast cells causing degranulation and release of histamine and other allergic mediators, which in turn produce the characteristic signs and symptoms of allergic conjunctivitis.

Four test formulations, containing combination 0.1% Cetirizine/0.005% Fluticasone ("low dose"), combination 0.25% Cetirizine/0.01% Fluticasone ("high dose"), 0.1% Cetirizine or 0.005% Fluticasone, were compared with vehicle alone (1% Polyethylene Glycol 400, NF; 0.2% Dibasic Sodium Phosphate, Anhydrous, USP; 0.25% Hypromellose, USP; 0.1% Polysorbate 80, NF; 1.8% Glycerin, USP; 0.025% Edetate Disodium, USP; 0.01% Benzalkonium Chloride, NF (pH 7.0)) and two commercial positive controls, Pred Forte® (prednisolone acetate 1%) and Pataday® (olopatadine 0.2%).

Systemic sensitization to short ragweed allergen (SRW) was induced by injecting SRW plus alum adjuvant systemically into Balb/c mice (Day 1), and by administration of topical SRW eyedrops on days 19-21. Topical ocular drug treatment was administered daily on days 19-21 after SRW injection. After 3 days of treatment, the animals were assessed for signs of allergic conjunctivits in response to challenge with topical SRW administration. Clinical assessments included conjunctival hyperemia, chemosis, discharge and lid swelling, each graded biomicroscopically on a 0-4 severity scale.

After 3 days of drug treatment, the animals treated with the combination 0.1% Cetirizine/0.005% Fluticasone demonstrated the least severity in three clinical signs (conjunctival hyperemia, chemosis, and lid swelling) as compared Cetirizine or Fluticasone alone or as compared to most other treatment groups. Cetirizine or Fluticasone alone produced no significant treatment effects.

The reduction in clinical signs in response to SRW challenge after 3 days of treatment with the combination 0.1% Cetirizine/0.005% Fluticasone was statistically significantly lower than Fluticasone alone for hyperemia ($p \leq 0.001$), chemosis ($p \leq 0.01$), lid swelling ($p \leq 0.03$) and total clinical score ($p \leq 0.01$); and than Cetirizine alone for chemosis ($p \leq 0.05$). Borderline Additionally, statistical significance was almost achieved against Cetirizine alone for total clinical score ($p = 0.06$). Surprisingly, the reduction with the combination was more than could have been expected from the efficacy of the individual components.

Furthermore, the combination of 0.1% Cetirizine/0.005% Fluticasone performed better than either the steroid (Pred Forte®) or antihistamine (Pataday®), commercial products used as positive controls in this study. Additionally, the higher concentration of the combination (0.25% Cetirizine/0.01% Fluticasone) was minimally effective in this model under this dosing regimen and conditions.

The results of this study indicate that a substantial clinical benefit may be achieved with the combination of low dose Cetirizine/Fluticasone over its individual components, over the high dose combination and over existing lead commercial products.

Experimental Design:

TABLE 3

Schedule of Procedures

| Procedure | Day 0 | Day 19 | Day 20 | Day 21 | Day 26 |
|---|---|---|---|---|---|
| Ocular Exam | X | | | X | |
| SRW Injection | X | | | | |
| Topical SRW | | X | X | X | |
| Dosing | | X | X | X | |
| Challenge | | | | X | |
| Behavior Observations | | | | X | |
| Photographs | | | | X | |
| Euthanasia | | | | | X |
| Eye Enucleations | | | | | X |

Sensitization

On Day 0, animals received injections containing a suspension of 50 μg of short ragweed allergen (SRW, Greer, Lenoir, N.C., USA) in 25 μL alum (aluminum hydroxide gel). Additional sensitization was achieved by topical dosing with 1 mg SRW in 5 μl PBS on Days 19 and 20 after injection.

Dosing

On days 19 through 21, topical treatment was administered once daily. Mice were dosed topically to the central cornea using a calibrated micropipette, with a 5 μL drop of treatment in each eye. The dose groups are outlined in the table below:

Challenge

On day 21, twenty minutes after ocular treatment dosing, animals were challenged with topical doses of 1000 μg SRW suspension in 5 μl PBS in each eye. SRW was prepared fresh and used within 3 hours of mixing, and mixed well before administration to ensure homogeneity.

TABLE 4

Test/Control Articles

| Group Number | Number of Animals | Test Article | Volume per Dose |
|---|---|---|---|
| 1 | 8 | 0.1% Cetirizine/0.005% Fluticasone | 5 μL |
| 2 | 8 | 0.25% Cetirizine/0.01% Fluticasone | 5 μL |
| 3 | 8 | 0.1% Cetirizine | 5 μL |
| 4 | 8 | 0.005% Fluticasone | 5 μL |
| 5 | 8 | Olopatadine HCl 0.2% (Pataday ®) | 5 μL |
| 6 | 8 | Pred. acetate 1% (Pred Forte ®) | 5 μL |
| 7 | 8 | Vehicle Control | 5 μL |

Experimental Procedures:

Ophthalmic exams were performed at baseline (study entry) according to the Ocular Irritation Grading Scale (Appendix 1) to verify that the eyes did not exhibit any signs of ocular irritation.

Ophthalmic exams were also performed on day 21, 15 minutes after the allergen challenge. Exams were performed under dissecting microscope, and included conjunctival hyperemia, chemoosis, tear/discharge, and lid swelling, each graded on a 0-4 scale (0.5 units were allowed for any ocular score).

There were no abnormal ophthalmic findings in any animals used in the study and no unscheduled deaths during this study.

Tissue Collections/Preservation and Statistical Analysis

Immediately after euthanasia ($CO_2$ inhalation and cervical dislocation), eyes and surrounding lid tissue was collected and placed immediately in 4% paraformaldehyde for 24 hours, after which they were transferred to 70% ethanol for storage prior to paraffin embedding and sectioning for histology.

Both eyes of each animal were averaged and all animals within a group were averaged to obtain an average score for each treatment group for each measurement parameter. Statistically significant differences between groups were determined using the 2-tailed, 2-sample t-test.

Results

Day 0 baseline exams ensured that all mice were free of any redness, swelling, and tearing.

After 3 days of drug treatment, the animals treated with the combination 0.1% Cetirizine/0.005% Fluticasone demonstrated the least severity in three of the four clinical signs (conjunctival hyperemia, chemosis, and lid swelling) as compared to Cetrizine or Fluticasone alone, and as compared to most other treatment groups. Total clinical score (sum of scores of all clinical signs in both eyes) was lowest in the 0.1% Cetirizine/0.005% Fluticasone combination group as compared to all other treatment groups. Cetirizine or Fluticasone alone produced no significant treatment effects.

The reduction in clinical signs in response to SRW challenge after 3 days of treatment with the combination 0.1% Cetirizine/0.005% Fluticasone was statistically significantly lower than Fluticasone alone for hyperemia ($p \leq 0.001$), chemosis ($p \leq 0.01$), lid swelling ($p \leq 0.03$) and total clinical score ($p \leq 0.01$); and than Cetirizine alone for chemosis ($p \leq 0.05$). Borderline significance was achieved against Cetirizine alone for total clinical score ($p = 0.06$).

Surprisingly, the high dose combination of 0.25% Cetirizine/0.01% Fluticasone was less effective than the low dose combination in this model for all clinical signs, with the exception of an effect on chemosis. The only statistically significant decrease in any clinical sign after high dose combination treatment was for chemosis as compared to Fluticasone alone (p≤0.05).

Under these treatment conditions (3 days of once-daily dosing), neither of the positive control test articles, commercially available Pred Forte (prednisolone acetate 1%), a steroid, or Pataday (olopatadine 0.2%), the leading anti-histamine, produced significant treatment effects, with the exception of a decrease in chemosis produced by olopatadine, comparable to the effect seen with the combination 0.1% Cetirizine/0.005% Fluticasone. This chemosis effect was statistically significantly different from Fluticasone alone (p≤0.05).

Figure 25:
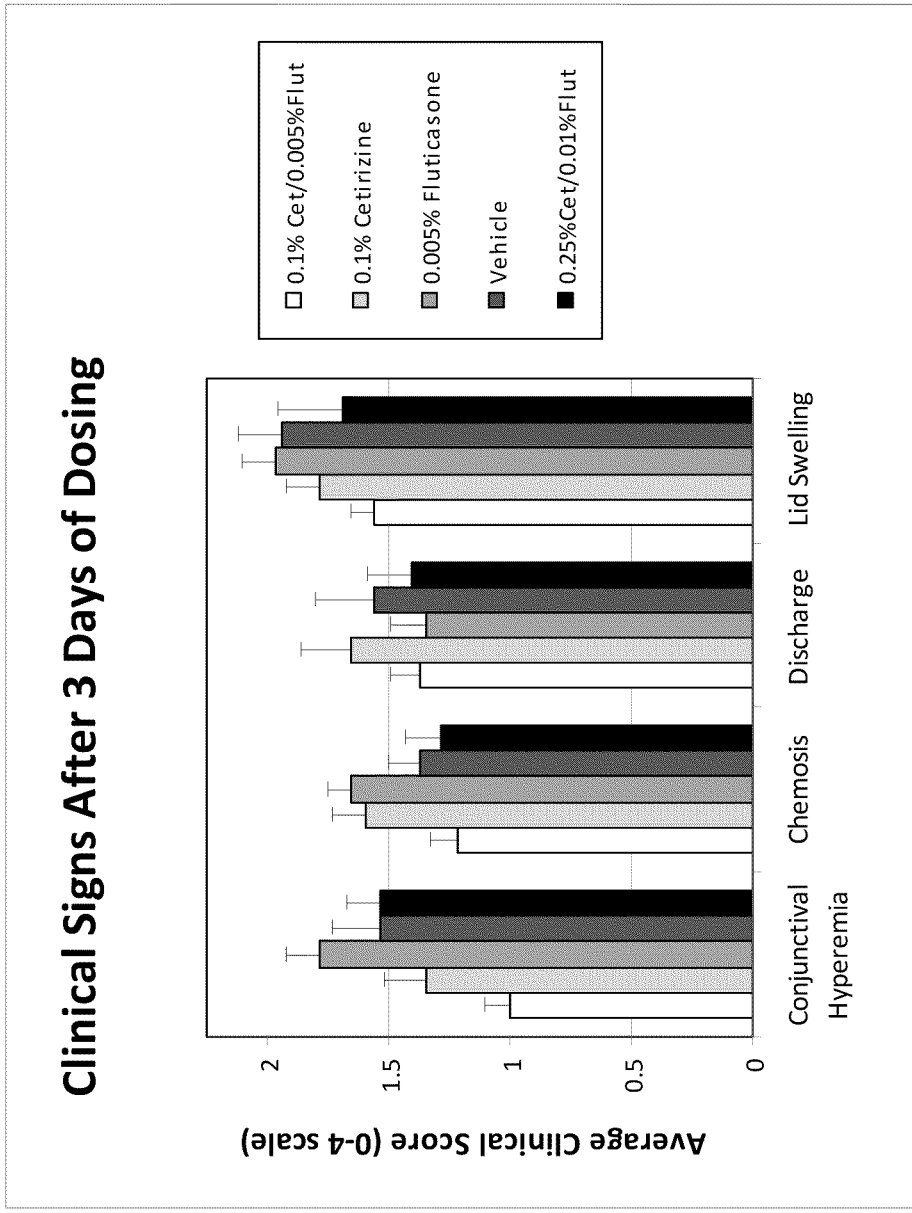
FIG. 25 is a bar graph summarizing the effects of a 0.1% cetirizine/0.005% fluticasone formulation (low dose) and a 0.25% cetirizine/0.01% fluticasone formulation (high dose) on conjunctival hyperemia, chemosis, discharge, and lid swelling after three days of dosing, as compared to 0.1% cetirizine alone, 0.005% fluticasone alone, and vehicle control.
Figure 26:
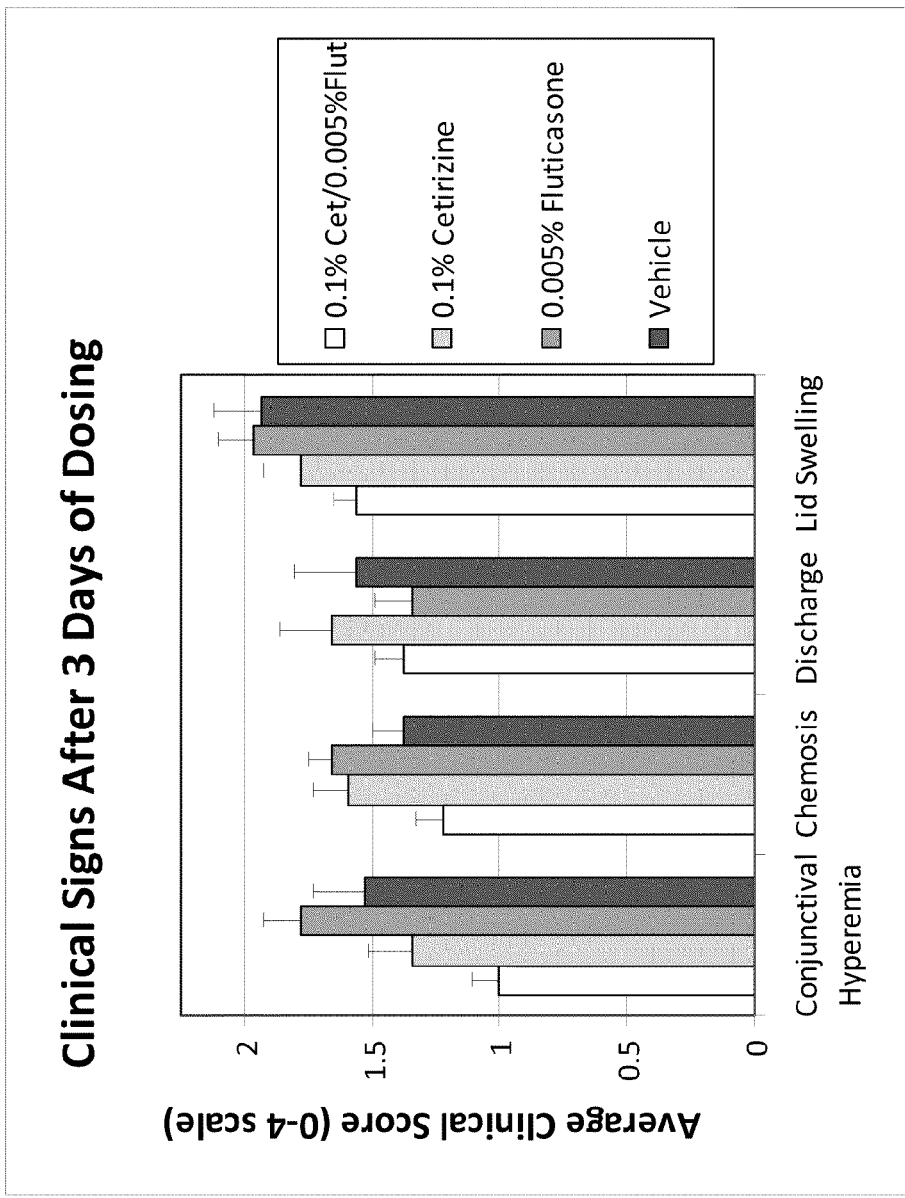
FIG. 26 is a bar graph summarizing the effects of a 0.1% cetirizine/0.005% fluticasone formulation (low dose) on conjunctival hyperemia, chemosis, discharge, and lid swelling after three days of dosing, as compared to 0.1% cetirizine alone, 0.005% fluticasone alone, and vehicle control.
Figure 27:
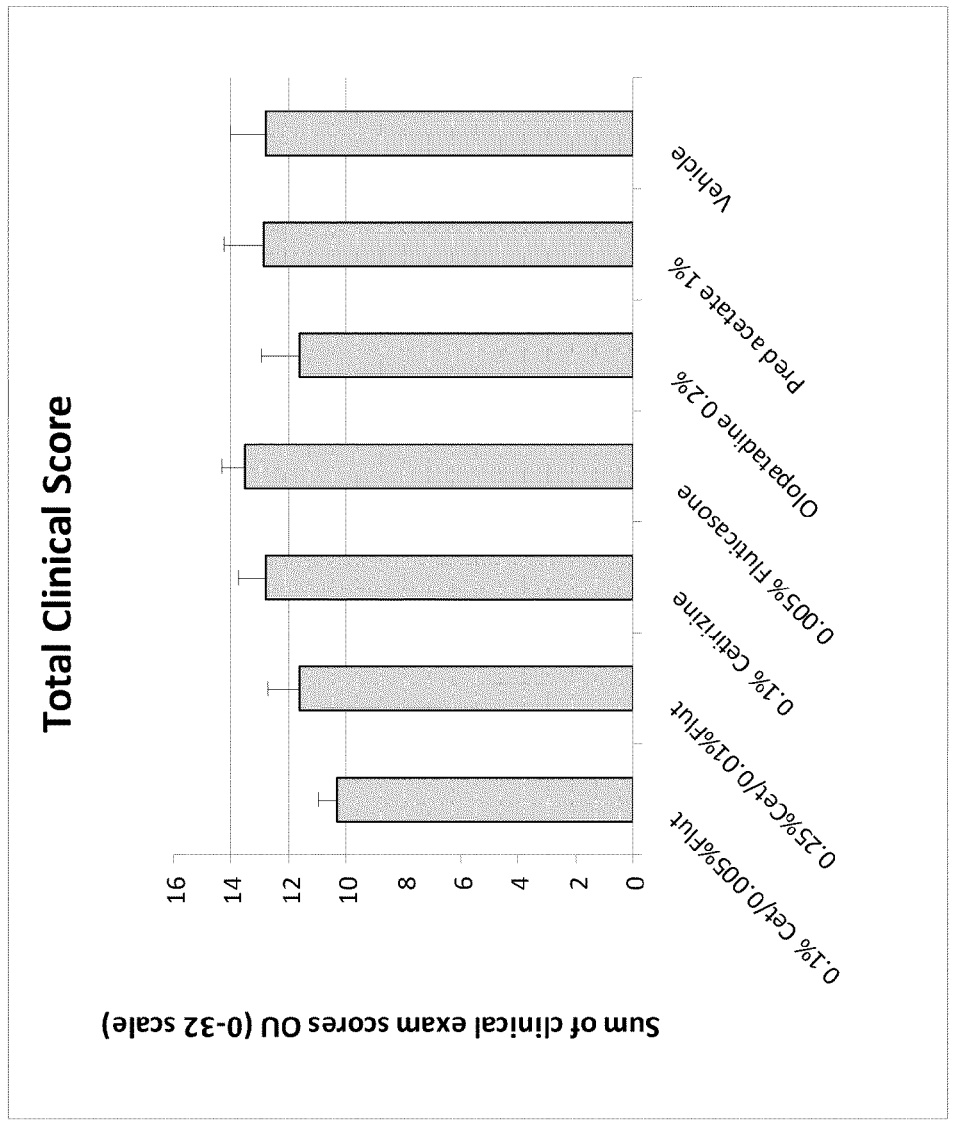
FIG. 27 is a bar graph summarizing the sum of clinical exam scores for a 0.1% cetirizine/0.005% fluticasone formulation (low dose) and a 0.25% cetirizine/0.01% fluticasone formulation (high dose), 0.1% cetirizine alone formulation, 0.005% fluticasone alone formulation, an olopatadine 0.2% formulation, a prednisolone acetate 1% formulation and a vehicle control.
Figure 28:
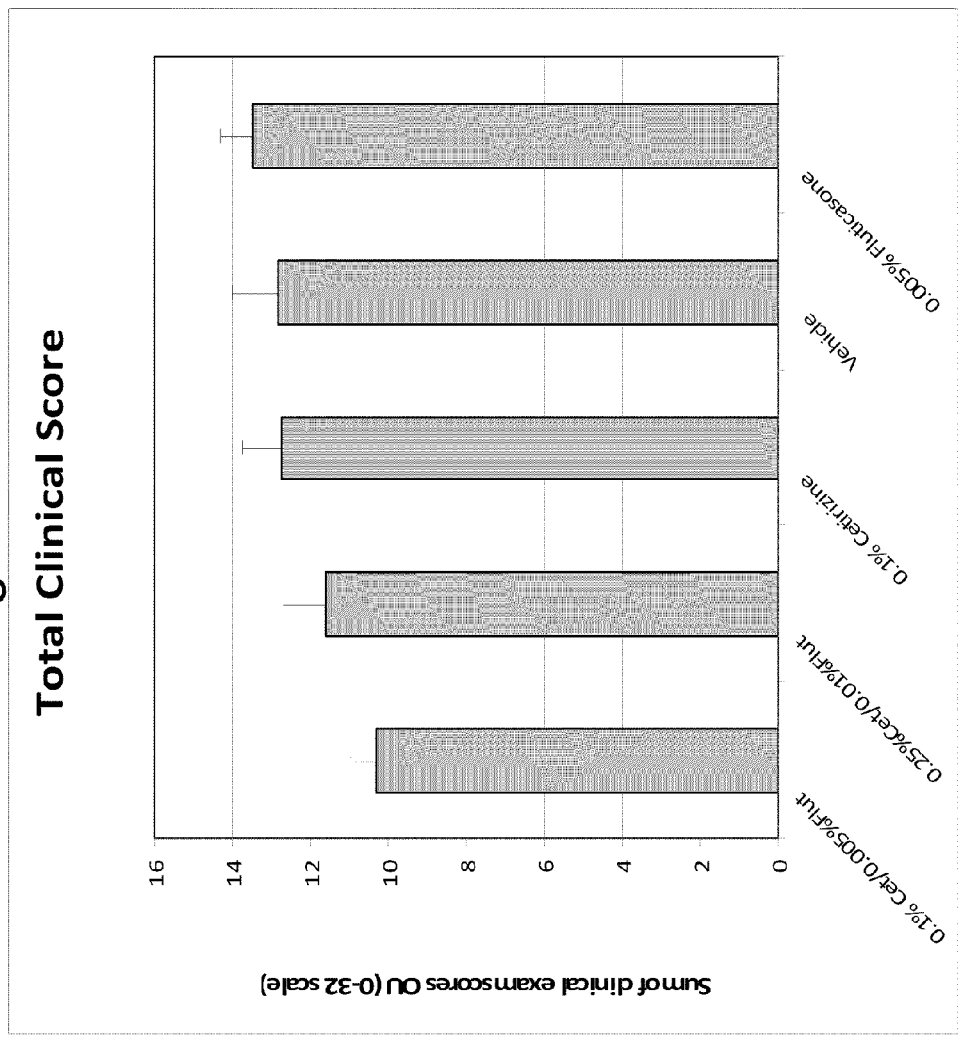
FIG. 28 is a bar graph summarizing the sum of clinical exam scores for a 0.1% cetirizine/0.005% fluticasone formulation (low dose) and a 0.25% cetirizine/0.01% fluticasone formulation (high dose), 0.1% cetirizine alone formulation, 0.005% fluticasone alone formulation, and a vehicle control.

The results are summarized in Table 5 below and in FIGS. 24-28.

roids—these results confirm the effectiveness of the specific combination of cetirizine/fluticasone at the preferred low dose concentrations.

Lastly, the low dose combination was more efficacious than its comparison arms across all endpoints, including total ocular composite score.

Example 4

Comfort Profile of Cetirizine/Fluticasone Formulation

The purpose of this study was to assess the comfort of a 0.1% cetirizine/0.005% fluticasone (low dose) formulation and a 0.25% cetirizine/0.01% fluticasone (high dose) formu-

TABLE 5

Summary of Results

| Treatment Group | Conjunctival Hyperemia | | Chemosis | | Discharge | | Lid Edema | | Total Clinical Score | |
|---|---|---|---|---|---|---|---|---|---|---|
| | Average | SEM | Avg | SEM | Avg | SEM | Avg | SEM | Avg | SEM |
| 0.1% Cetirizine/ 0.005% Fluticasone | 1.00 | 0.11 | 1.22 | 0.11 | 1.38 | 0.12 | 1.56 | 0.09 | 10.31 | 0.66 |
| 0.25% Cetirizine/ 0.01% Fluticasone | 1.53 | 0.14 | 1.28 | 0.15 | 1.41 | 0.18 | 1.69 | 0.27 | 11.63 | 1.09 |
| 0.1% Cetirizine | 1.34 | 0.17 | 1.59 | 0.14 | 1.66 | 0.21 | 1.78 | 0.15 | 12.75 | 1.00 |
| 0.005% Fluticasone | 1.78 | 0.15 | 1.66 | 0.09 | 1.34 | 0.15 | 1.97 | 0.14 | 13.50 | 0.80 |
| Olopatadine HCl 0.2% (Pataday ®) | 1.47 | 0.25 | 1.19 | 0.19 | 1.53 | 0.15 | 1.63 | 0.16 | 11.63 | 1.34 |
| Pred. acetate 1% (Pred Forte ®) | 1.61 | 0.14 | 1.50 | 0.12 | 1.79 | 0.26 | 1.93 | 0.28 | 12.86 | 1.43 |
| Vehicle Control | 1.53 | 0.20 | 1.38 | 0.13 | 1.56 | 0.24 | 1.94 | 0.18 | 12.81 | 1.19 |

CONCLUSION

The low dose combination of 0.1% Cetirizine/0.005% Fluticasone was the most effective at preventing signs of allergic conjunctivitis in the murine ragweed sensitization model. Neither component of the combination used alone, at the same concentrations, produced a substantial treatment effect. The low-dose combination, assessed after 3 days of treatment and 15 minutes after ragweed challenge, reduced conjunctival hyperemia, chemosis, and lid swelling, and resulted in the lowest clinical summary score of any of the treatment arms, including the cetirizine or fluticasone alone, and commercial ophthalmics Pataday® and Pred Forte®.

Surprisingly, the higher concentration of the combination (0.25% Cetirizine/0.01% Fluticasone) was minimally effective in this model under this dosing regimen and conditions. These results indicate that the 0.1% Cetirizine/0.005% Fluticasone formulation has excellent potential for the prevention and treatment of allergic conjunctivitis and that a substantial clinical benefit might be achieved with the combination of Cetirizine/Fluticasone over either medication used alone.

In summary, the results consistently favored 0.1% cetirizine/0.005% fluticasone combination (low dose) over both the individual components alone as well as the high dose combination (0.25% cetirizine/0.01% fluticasone), which is surprising because one skilled in the art might expect the higher dose formulation to work at least equally well if not better than the low dose formulation. The low dose combination also worked better than would be expected from the results of the individual components, thus showed a synergistic effect between the cetirizine and fluticasone Additionally, the low dose combination worked better than well known, leading ocular antihistamines and ocular stelation upon instillation in the human eye (N=5). The low dose and high dose combinations were each formulated in 1% Polyethylene Glycol 400, NF; 0.2% Dibasic Sodium Phosphate, Anhydrous, USP; 0.25% Hypromellose, USP; 0.1% Polysorbate 80, NF; 1.8% Glycerin, USP; 0.025% Edetate Disodium, USP; 0.01% Benzalkonium Chloride, NF, as reflected in Tables 6 and 6 below:

TABLE 6

0.005% Fluticasone Propionate/0.1% Cetirizine Ophthalmic Suspension

| Concentration | Ingredient | Purpose |
|---|---|---|
| 0.005% | Fluticasone Propionate, USP | Active, Steroid |
| 1% | Polyethylene Glycol 400, NF | Carrier |
| 0.2% | Dibasic Sodium Phosphate, Anhydrous, USP | Buffer |
| 0.1188% | Cetirizine Dihydrochloride, Ph. Eur. | Active, Antihistamine |
| 0.25% | Hypromellose, USP | Viscosity agent |
| 0.1% | Polysorbate 80, NF | Surfactant |
| 1.8% | Glycerin, USP | Tonicity Agent |
| 0.025% | Edetate Disodium, USP | Chelating Agent |
| 0.01% | Benzalkonium Chloride, N.F. | Preservative |
| q.s. | Sterile Purified Water | Vehicle |

TABLE 7

0.01% Fluticasone Propionate/0.25% Cetirizine Ophthalmic Suspension

| Concentration | Ingredient | Purpose |
|---|---|---|
| 0.01% | Fluticasone Propionate, USP | Active, Steroid |
| 2% | Polyethylene Glycol 400, NF | Carrier |
| 0.2% | Dibasic Sodium Phosphate, Anhydrous, USP | Buffer |
| 0.297% | Cetirizine Dihydrochloride, Ph. Eur. | Active, Antihistamine |
| 0.25% | Hypromellose, USP | Viscosity agent |
| 0.1% | Polysorbate 80, NF | Surfactant |
| 1.2% | Glycerin, USP | Tonicity Agent |
| 0.025% | Edetate Disodium, USP | Chelating Agent |
| 0.01% | Benzalkonium Chloride, N.F. | Preservative |
| q.s. | Sterile Purified Water | Vehicle |

Each of the formulations in Tables 5 and 6 had a pH 7.0 and an osmolality of 300 mOsm/kg.

One drop of masked study medication was instilled in each eye and subjects were asked to assess the comfort of the drop on a subjective scale of 0 to 10 (0=comfortable, 10=very uncomfortable (Note: The most uncomfortable commercially available allergy drop=4). The results are shown in FIG. 29. Both the low dose and high dose formulations were well tolerated (average comfort score <3) and were found to be more comfortable than the formulation comprising 0.005% fluticasone alone as the only active agent, which had an osmolality of 900 mOsm/kg (average comfort score ~3; See FIGS. 20-21, Example 2).

Example 5

Clinical Efficacy of Cetirizine/Fluticasone Formulations

A placebo controlled, double-blind study will be conducted to evaluate the efficacy of cetirizine 0.1%/fluticasone 0.005% formulation (low dose) formulation compared to the individual treatment arms (i.e., cetirizine alone and fluticasone alone) and a vehicle control.

Subjects will undergo 2 screening visits (an allergen titration and confirmation) followed by a drug evaluation visit. At the drug evaluation visit, one drop of masked study medication will be instilled in both eyes and comfort assessments will be taken. Sixteen hours later subjects will be challenged with allergen (conjunctival allergen challenge; "CAC") and allergic assessments will be taken. Subjects will be asked to subjectively rate their ocular itching on a scale of 0 to 4 (0=little to no itching, 4=extreme itching). Conjuctival redness (post-CAC) will also be evaluated. Subjects will be further asked to keep a diary to evaluate ocular itching and conjunctival redness over a 2 week period. Intraocular pressure ("IOP") measurements and any adverse events will be measured/collected over 14 days dosing.

Based on the surprising results of the in vivo animal study described in Example 3 above, it is anticipated that the low dose cetirizine/fluticasone formulation will be more efficacious than both the individual components (i.e., cetirizine alone and fluticasone alone) and the vehicle control in reducing ocular itching and conjunctival redness (post-CAC). Based on the clinical efficacy of the 0.1% cetirizine alone formulation (see Example 1), it is anticipated that the low 0.1% cetirizine/0.005% fluticasone formulation will be even more efficacious in reducing the signs and symptoms of allergic conjunctivitis for at least 16 hours or more, as compared to the cetirizine alone, and will have better efficacy at treating the late phase allergic inflammation response.

Example 6

Stability of 0.10% Cetirizine Formulation and Combined Cetirizine/Fluticasone Formulations Tables 8-9 below show that a 0.1% formulation of cetirizine was stable for at least three months both at room temperature (Table 6) and at higher temperatures (Table 7).

Tables 10-11 below show that a 0.1% cetirizine/0.005% fluticasone formulation (in 1% Polyethylene Glycol 400, NF; 0.2% Dibasic Sodium Phosphate, Anhydrous, USP; 0.25% Hypromellose, USP; 0.1% Polysorbate 80, NF; 1.8% Glycerin, USP; 0.025% Edetate Disodium, USP; 0.01% Benzalkonium Chloride, NF (pH 7.0); i.e., the formulation listed in Table 5) was stable for at least one month at both room temperature (Table 8) and at higher temperature (Table 9) when stored upright.

Tables 12 and 13 show that a 0.25% cetirizine/0.01% fluticasone formulation (in 1% Polyethylene Glycol 400, NF; 0.2% Dibasic Sodium Phosphate, Anhydrous, USP; 0.25% Hypromellose, USP; 0.1% Polysorbate 80, NF; 1.8% Glycerin, USP; 0.025% Edetate Disodium, USP; 0.01% Benzalkonium Chloride, NF (pH 7.0); i.e., the formulation listed in Table 6) was stable for at least one month at room temperature (Table 10) and at a higher temperature (Table 11) when stored upright.

Cetirizine and fluticasone concentrations were quantified by high pressure liquid chromatography (HPLC). Impurities are shown as "relative retention time" or RRT in the table, which relates the unknown peak to the elution time of the parent peak, cetirizine (or fluticasone). At no time did the total impurities exceed 1%. Sterility, particulate matter, and preservative efficacy were determined only at the initial time point because these should remain unchanged provided that the sealed container is not compromised.

The data herein demonstrates cetirizine and cetirizine/fluticasone formulations that are stable without the inclusion of a cyclodextrin or other solubilizing compound. Without intending to be bound by any theory, the stability was achieved by minimizing/excluding the addition of counter ions or metal based buffers that could promote salt formation, precipitation, or metal based degradation.

TABLE 8

Cetirizine 0.10%/Benzalkonium Chloride 0.01% (w/v) Ophthalmic Solution Stability Testing: 25° C./60% RH (QA Oct. 13, 2008)
Lot #: 04262008@18

| Test | Limits/Specification | Initial Jun. 9, 2008 | 1 Month Jul. 9, 2008 | 2 Month Aug. 11, 2008 | 3 Month Sep. 10, 2008 |
|---|---|---|---|---|---|
| Appearance (Contents) | Clear and colorless to slightly yellow solution | Conforms: Clear, Colorless Solution | Conforms: Clear, Colorless Solution | Conforms: Clear, Colorless Solution | Conforms: Clear, Colorless Solution |

TABLE 8-continued

Cetirizine 0.10%/Benzalkonium Chloride 0.01% (w/v) Ophthalmic Solution Stability Testing: 25° C./60% RH (QA Oct. 13, 2008)
Lot #: 04262008@18

| Test | Limits/Specification | Initial Jun. 9, 2008 | 1 Month Jul. 9, 2008 | 2 Month Aug. 11, 2008 | 3 Month Sep. 10, 2008 |
|---|---|---|---|---|---|
| Appearance (Container Integrity) | No leakage observed, container intact | Conforms: No leakage, container intact | Conforms: No leakage, container intact | Conforms: No leakage, container intact | Conforms: No leakage, container intact |
| Assay: Cetirizine Label Claim: 0.10% (w/v) (equivalent to Cetirizine dihydrochloride 0.1188%) | NLT 90.0% and NMT 110.0% of Label Claim (LC) | 99.2% LC | 99.5% LC | 99.7% LC | 99.4% LC |
| Assay of Ketotifen Impurities (Total, Ketotifen impurities, Cetirizine impurities) | Absence of Active Report individual ≥ 0.05% Report Total | Not Detected RRT @ 0.93: 0.06% RRT @ 1.1: 0.15% Total: 0.2% | Not Detected RRT @ 0.90: 0.06% RRT @ 1.60: 0.06% RRT @ 2.11: 0.06% Total: 0.2% | Not Detected RRT @ 0.67: 0.07% RRT @ 0.91: 0.06% RRT @ 1.10: 0.05% RRT @ 1.11: 0.09% RRT @ 2.33: 0.06% Total: 0.30%% | Not Detected RRT @ 0.63: 0.09% RRT @ 0.92: 0.05% RRT @ 1.08: 0.05% RRT @ 1.10: 0.09% RRT @ 1.56: 0.08% Total: 0.40%% |
| Assay: Benzalkonium Chloride Label Claim: 0.01% (w/v) | NLT 85.0% and NMT 115% of Label Claim | 99.4% LC | 94.6% LC | 100.0% LC | 94.7% LC |
| pH | 5.5 ± 0.5 | 5.7 | 6.0 | 6.0 | 5.9 |
| Osmolality | Report | 253 mOsm/Kg · H$_2$0 | 253 mOsm/Kg · H$_2$0 | 253 mOsm/Kg · H$_2$0 | 252 mOsm/Kg · H$_2$0 |
| Sterility | Meets USP Criteria | Pass | | | |
| Particulate Matter | Number of particles with diameter of: ≥10 μm: NMT 50/mL ≥25 μm: NMT 5/mL ≥50 μm: NMT 2/mL | Pass | | | |
| Antimicrobial Preservative Efficacy | Report | Pass | | | |

TABLE 9

Cetirizine 0.10%/Benzalkonium Chloride 0.01% (w/v) Ophthalmic Solution Stability Testing: 40° C./75% RH (QA Oct. 13, 2008)
(Lot #: 04262008@18)

| Test | Limits/Specification | Initial Jun. 9, 2008 | 1 Month Jul. 9, 2008 | 2 Month Aug. 11, 2008 | 3 Month Sep. 10, 2008 |
|---|---|---|---|---|---|
| Appearance (Contents) | Clear and colorless to slightly yellow solution | Conforms: Clear, Colorless Solution | Conforms: Clear, Colorless Solution | Conforms: Clear, Colorless Solution | Conforms: Clear, Colorless Solution |
| Appearance (Container Integrity) | No leakage observed, container intact | Conforms: No leakage, container intact | Conforms: No leakage, container intact | Conforms: No leakage, container intact | Conforms: No leakage, container intact |
| Assay: Cetirizine Label Claim: 0.10% (w/v) (equivalent to Cetirizine dihydrochloride 0.1188%) | NLT 90.0% and NMT 110.0% of Label Claim (LC) | 99.2% LC | 99.6% LC | 100.1% LC | 99.4% LC |
| Assay of Ketotifen Impurities (Total, Ketotifen impurities, Cetirizine impurities) | Absence of Active Report individual ≥ 0.05% Report Total | Not Detected RRT @ 0.93: 0.06% RRT @ 1.1: 0.15% Total: 0.2% | Not Detected RRT @ 0.90: 0.06% RRT @ 2.11: 0.06% Total: 0.1% | Not Detected RRT @ 0.67: 0.34% RRT @ 0.78: 0.05% RRT @ 0.91: 0.06% RRT @ 1.10: 0.05% RRT @ 1.11: 0.09% RRT @ 2.33: 0.06% Total: 0.70%% | Not Detected RRT @ 0.63: 0.44% RRT @ 0.92: 0.05% RRT @ 1.10: 0.09% Total: 0.6% |
| Assay: Benzalkonium Chloride Label Claim: 0.01% (w/v) | NLT 85.0% and NMT 115% of Label Claim | 99.4% LC | 92.9% LC | 99.1% LC | 96.8% LC |

TABLE 9-continued

Cetirizine 0.10%/Benzalkonium Chloride 0.01% (w/v) Ophthalmic Solution Stability Testing: 40° C./75% RH (QA Oct. 13, 2008)
(Lot #: 04262008@18)

| Test | Limits/Specification | Initial Jun. 9, 2008 | 1 Month Jul. 9, 2008 | 2 Month Aug. 11, 2008 | 3 Month Sep. 10, 2008 |
|---|---|---|---|---|---|
| pH | 5.5 ± 0.5 | 5.7 | 6.0 | 5.9 | 5.7 |
| Osmolality | Report | 253 mOsm/Kg · $H_2O$ | 254 mOsm/Kg · $H_2O$ | 254 mOsm/Kg · $H_2O$ | 255 mOsm/Kg · $H_2O$ |
| Sterility | Meets USP Criteria | Pass | | | |
| Particulate Matter | Number of particles with diameter of: ≥10 μm: NMT 50/mL ≥25 μm: NMT 5/mL ≥50 μm: NMT 2/mL | Pass | | | |
| Antimicrobial Preservative Efficacy | Report | Pass | | | |

TABLE 10

0.005% Fluticasone Propionate/0.1% Cetirizine Ophthalmic
Suspension Stability Testing: 25° C./40% RH
(Lot Number: Ora091202.V1)

| Test | Specification | Initial Dec. 15, 2009 Inverted Orientation | 1 Week Dec. 21, 2009 Inverted Orientation |
|---|---|---|---|
| Appearance (Solution) | Report Results | Clear, Colorless, no ppt. | Clear, Colorless, no ppt. |
| Appearance (Container) | No leakage observed, container intact | NT | No leakage observed, container intact |
| Fluticasone Propionate Assay | 90%-110% Label Claim | 95.1% LC | 98.6% LC |
| Fluticasone Related Substances | Report individual % AUC, | RRT 0.19: 0.75% AUC RRT 0.36: 0.35% AUC | RRT 0.19: 0.50% AUC RRT 0.36: 0.40% AUC |
| | Report total, % AUC | Total: 1.07% AUC | RRT 0.66: 0.24% AUC RRT 0.93: 0.07% AUC Total: 1.21% |
| Cetirizine Assay | 90%-110% Label Claim | 98.6% LC | 97.2% LC |
| Cetirizine Related Substances | Report individual % AUC, | RRT 0.96: 0.5% AUC RRT 1.13: 0.08% AUC | RRT 0.96: 0.05% AUC RRT 1.13: 0.18% AUC |
| | Report total, % AUC | Total: 0.13% | Total: 0.23% |
| Benzalkonium chloride Assay | 50%-150% Label Claim | 99.5% LC | NT |
| Disodium Edetate | 70%-120% Label Claim | 95.8% LC | NT |
| pH | 6.5-7.8 | 7.1 | 7.0 |
| Osmolality | Report results | 291 mOsm/Kg | 290 mOsm/Kg |

| Test | 2 Week Dec. 28, 2009 Inverted Orientation | 2 Week Jan. 04, 2010 Upright Orientation | 1 Month Jan. 13, 2010 Upright Orientation |
|---|---|---|---|
| Appearance (Solution) | Clear, Colorless, no ppt. | NT | Slightly Turbid Solution |
| Appearance (Container) | No leakage observed, container intact | NT | No leakage observed, container intact |
| Fluticasone Propionate Assay | 89.4% LC* | 102.4% LC | 99.6% LC |
| Fluticasone Related | RRT 0.09: 0.06% AUC | RRT 0.07: 0.25% AUC | RRT 0.12: 0.39% AUC |

TABLE 10-continued 0.005% Fluticasone Propionate/0.1% Cetirizine Ophthalmic
Suspension Stability Testing: 25° C./40% RH
(Lot Number: Ora091202.V1)

| Substances | RRT 0.10: 0.14% AUC<br>RRT 0.12: 0.72% AUC<br>RRT 0.27: 0.49% AUC | RRT 0.09: 0.06% AUC<br>RRT 0.10: 0.16% AUC<br>RRT 0.12: 0.53% AUC | RRT 0.14: 0.63% AUC<br>RRT 0.29: 0.41% AUC<br>RRT 0.34: 0.10% AUC |
|---|---|---|---|
| | RRT 0.33: 0.18% AUC<br>RRT 0.52: 0.05% AUC | RRT 0.27: 0.46% AUC<br>RRT 0.33: 0.14% AUC | Total: 1.53% AUC |
| | RRT 0.61: 0.29% AUC<br>RRT 0.76: 0.23% AUC<br>RRT 0.88: 0.27% AUC | Total: 1.6% | |
| Cetirizine Assay | Total: 2.43%<br>98.0% LC | NT | 96.5% LC |
| Cetirizine Related | RRT 0.96: 0.05% AUC | NT | RRT 1.13: 0.53% AUC |
| Substances | RRT 1.13: 0.19% AUC | | Total: 0.53% AUC |
| Benzalkonium chloride Assay | Total: 0.24%<br>NT | NT | 101.0% LC |
| Disodium Edetate | NT | NT | 91.2% LC |
| pH | 7.0 | NT | 7.0 |
| Osmolality | 291 mOsm/Kg | NT | 290 mOsm/Kg |

RH = relative humidity, LC = label claim, AUC = area under curve, NT = not tested.

*The low assay values were attributed to the inverted orientation in which the stability samples were stored. Samples stored in the upright orientation were tested at the 2-week time point and subsequent time points, as reflected in the data shown.

TABLE 11

0.005% Fluticasone Propionate/0.1% Cetirizine Ophthalmic
Suspension Stability Testing: 40° C./NMT 25% RH
(Lot Number: Ora091202.V1)

| | | Initial | 1 Week |
|---|---|---|---|
| | | Date Pulled | |
| Test | Specification | Dec. 15, 2009<br>Inverted Orientation | Dec. 21, 2009<br>Inverted Orientation |
| Appearance (Solution) | Report Results | Clear, Colorless, no ppt. | Clear, Colorless, no ppt. |
| Appearance (Container) | No leakage observed, container intact | NT | No leakage observed, Container intact |
| Fluticasone Propionate Assay | 90%-110% Label Claim | 95.1% LC | 82.2% LC* |
| Fluticasone Related Substances | Report individual % AUC, | RRT 0.19: 0.75% AUC<br>RRT 0.36: 0.35% AUC | RRT 0.19: 0.18% AUC<br>RRT 0.36: 0.48% AUC |
| | Report total, % AUC | Total: 1.07% AUC | RRT 0.66: 0.32% AUC<br>RRt 0.93: 0.18% AUC |
| | | | Total: 1.40% |
| Cetirizine Assay | 90%-110% Label Claim | 98.6% LC | 97.2% LC |
| Cetirizine Related Substances | Report individual % AUC,<br>Report total, % AUC | RRT 0.96: 0.5% AUC<br>RRT 1.13: 0.08% AUC<br>Total: 0.13% | RRT 1.13: 0.47% AUC<br>Total: 0.47% |
| Benzalkonium chloride Assay | 50%-150% Label Claim | 99.5% LC | NT |
| Disodium Edetate | 70%-120% Label Claim | 95.8% LC | NT |
| pH | 6.5-7.8 | 7.1 | 7.0 |
| Osmolality | Report results | 291 mOsm/Kg | 292 mOsm/Kg |
| | | 2 Week | 2 Week | 1 Month |
| | | Date Pulled | | |
| Test | | Dec. 28, 2009<br>Inverted Orientation | Jan. 04, 2010<br>Upright Orientation | Jan. 13, 2010<br>Upright Orientation |
| Appearance (Solution) | | Clear, Colorless, no ppt. | NT | Slightly turbid solution |

TABLE 11-continued 0.005% Fluticasone Propionate/0.1% Cetirizine Ophthalmic
Suspension Stability Testing: 40° C./NMT 25% RH
(Lot Number: Ora091202.V1)

| Appearance (Container) | No leakage observed, Container intact | NT | No leakage observed, container intact |
|---|---|---|---|
| Fluticasone Propionate Assay | 58.4% LC* | 103.2% LC | 101.4% LC |
| Fluticasone Related Substances | RRT 0.09: 0.66% AUC | RRT 0.07: 0.26% AUC | RRT 0.11: 0.69% AUC |
| | RRT 0.10: 0.59% AUC | RRT 0.09: 0.52% AUC | RRT 0.14: 0.59% AUC |
| | RRT 0.12: 0.72% AUC | RRT 0.10: 0.13% AUC | RRT 0.29: 0.35% AUC |
| | RRT 0.28: 0.72% AUC | RRT 0.12: 0.35% AUC | RRT 0.34: 0.60% AUC |
| | RRT 0.33: 1.12% AUC | RRT 0.27: 0.43% AUC | Total: 2.23% AUC |
| | RRT 0.45: 0.20% AUC | RRT 0.33: 0.19% AUC | |
| | RRT 0.53: 0.14% AUC | RRT 0.76: 0.06% AUC | |
| | RRT 0.60: 0.14% AUC | Total: 2.02% | |
| | RRT 0.76: 0.31% AUC | | |
| | RRT 0.88: 0.49% AUC | | |
| | Total: 5.20% | | |
| Cetirizine Assay | 97.9% LC | NT | 96.8% LC |
| Cetirizine Related Substances | RRT 1.13: 0.48% AUC | NT | RRT 1.13: 0.82% AUC |
| | Total: 0.48% | | Total: 0.82% AUC |
| Benzalkonium chloride Assay | NT | NT | 101.3% LC |
| Disodium Edetate | NT | NT | 91.0% LC |
| pH | 7.0 | NT | 7.0 |
| Osmolality | 293 mOsm/Kg | NT | 291 mOsm/Kg |

RH = relative humidity, LC = label claim, AUC = area under curve, NT = not tested.

*The low assay values were attributed to the inverted orientation in which the stability samples were stored. Samples stored in the upright orientation were tested at the 2-week time point and subsequent time points, as reflected in the data shown.

TABLE 12

0.01% Fluticasone Propionate/0.25% Cetirizine Ophthalmic
Suspension Stability Testing: 25° C./40% RH
(Lot Number: Ora091130.V1)

| Test | Specification | Initial<br>Date Pulled<br>Dec. 15, 2009<br>Inverted Orientation | 1 Week<br><br>Dec. 21, 2009<br>Inverted Orientation |
|---|---|---|---|
| Appearance (Solution) | Report Results | Clear, Colorless, no ppt. | Clear, colorless, no ppt |
| Appearance (Container) | No leakage observed, container intact | NT | No leakage observed, container intact |
| Fluticasone Propionate Assay | 90%-110% Label Claim | 96.9% LC | 98.9% LC |
| Fluticasone Related Substances | Report individual % AUC, | RRT 0.18: 0.82% AUC<br>RRT 0.35: 0.40% AUC | RRT 0.19: 0.61% AUC<br>RRT 0.35: 0.47% AUC |
| | Report total, % AUC | Total: 1.22% | RRT 0.67: 0.43% AUC<br>Total: 1.51% |
| Cetirizine Assay | 90%-110% Label Claim | 99.3% LC | 97.3% LC |
| Cetirizine Related Substances | Report individual % AUC, | RRT 0.96: 0.05% AUC<br>RRT 1.13: 0.14% AUC | RRT 0.96: 0.05% AUC<br>RRT 1.13: 0.31% AUC |
| | Report total, % AUC | Total: 0.19% | Total: 0.36% |
| Benzalkonium chloride Assay | 50%-150% Label Claim | 96.7% LC | NT |
| Disodium Edetate | 70%-120% Label Claim | 92.9% LC | NT |
| pH | 6.5-7.8 | 7.1 | 7.1 |
| Osmolality | Report results | 272 mOsm/Kg | 273 mOsm/Kg |

TABLE 12-continued 0.01% Fluticasone Propionate/0.25% Cetirizine Ophthalmic
Suspension Stability Testing: 25° C./40% RH
(Lot Number: Ora091130.V1)

| | 2 Week | 2 Week | 1 Month |
|---|---|---|---|
| | | Date Pulled | |
| Test | Dec. 28, 2009<br>Inverted Orientation | Jan. 04, 2010<br>Upright Orientation | Jan. 13, 2010<br>Upright Orientation |
| Appearance (Solution) | Clear, colorless, no ppt | NT | Slightly turbid solution |
| Appearance (Container) | No leakage observed, container intact | NT | No leakage observed, container intact |
| Fluticasone Propionate Assay | 79.0% LC* | 99.6% LC | 99.2% LC |
| Fluticasone Related Substances | RRT 0.06: 0.36% AUC<br>RRT 0.09: 0.38% AUC<br>RRT 0.12: 0.82% AUC | RRT 0.06: 0.49% AUC<br>RRT 0.09: 0.38% AUC<br>RRT 0.12: 0.66% AUC | RRT 0.11: 0.46% AUC<br>RRT 0.13: 0.74% AUC<br>RRT 0.29: 0.50% AUC |
| | RRT 0.27: 0.67% AUC<br>RRT 0.33: 0.20% AUC<br>RRT 0.44: 0.31% AUC | RRT 0.27: 0.53% AUC<br>RRT 0.36: 0.20% AUC<br>RRT 0.52: 0.09% AUC | Total: 1.17% AUC |
| | RRT 0.51: 0.42% AUC<br>RRT 0.60: 0.27% AUC<br>RRT 0.76: 1.04% AUC<br>RRT 0.88: 1.48% AUC | Total: 2.35% | |
| | Total: 6.14% | | |
| Cetirizine Assay | 98.7% LC | NT | 97.2% LC |
| Cetirizine Related Substances | RRT 0.96: 0.05% AUC<br>RRT 1.13: 0.32% AUC | NT | RRT 1.13: 0.75% AUC<br>Total: 0.75% AUC |
| | Total: 0.37% | | |
| Benzalkonium chloride Assay | NT | NT | 100.6% LC |
| Disodium Edetate | NT | NT | 89.7% LC |
| pH | 7.1 | NT | 7.1 |
| Osmolality | 274 mosm/Kg | NT | 273 mOsm/Kg |

RH = relative humidity, LC = label claim, AUC = area under curve, NT = not tested.
*The low assay values were attributed to the inverted orientation in which the stability samples were stored. Samples stored in the upright orientation were tested at the 2-week time point and subsequent time points, as reflected in the data shown.

TABLE 13

0.01% Fluticasone Propionate/0.25% Cetirizine Ophthalmic
Suspension Stability Testing: 40° C./NMT 25% RH
(Lot Number: Ora091130.V1)

| | | Initial | 1 Week |
|---|---|---|---|
| | | Date Pulled | |
| Test | Specification | Dec. 15, 2009<br>Inverted Orientation | Dec. 21, 2009<br>Inverted Orientation |
| Appearance (Solution) | Report Results | Clear, Colorless, no ppt. | Clear, colorless, no ppt |
| Appearance (Container) | No leakage observed, container intact | NT | No leakage observed, container intact |
| Fluticasone Propionate Assay | 90%-110% Label Claim | 96.9% LC | 98.5% LC |
| Fluticasone Related Substances | Report individual % AUC, | RRT 0.18: 0.82% AUC<br>RRT 0.35: 0.40% AUC | RRT 0.19: 0.47% AUC<br>RRT 0.35: 0.49% AUC |
| | Report total, % AUC | Total: 1.22% | RRT 0.66: 0.38% AUC |
| | | | Total: 1.34% |
| Cetirizine Assay | 90%-110% Label Claim | 99.3% LC | 97.1% LC |
| Cetirizine Related Substances | Report individual % AUC, | RRT 0.96: 0.05% AUC<br>RRT 1.13: 0.14% AUC | RRT 0.46: 0.08% AUC<br>RRT 1.13: 0.69% AUC |
| Benzalkonium chloride Assay | Report total, % AUC<br>50%-150% Label Claim | Total: 0.19%<br>96.7% LC | Total: 0.77%<br>NT |

TABLE 13-continued 0.01% Fluticasone Propionate/0.25% Cetirizine Ophthalmic
Suspension Stability Testing: 40° C./NMT 25% RH
(Lot Number: Ora091130.V1)

| | | | |
|---|---|---|---|
| Disodium Edetate | 70%-120% Label Claim | 92.9% LC | NT |
| pH | 6.5-7.8 | 7.1 | 7.1 |
| Osmolality | Report results | 272 mOsm/Kg | 273 mOsm/Kg |

| | 2 Week | 2 Week | 1 Month |
|---|---|---|---|
| | | Date Pulled | |
| Test | Dec. 28, 2009 Inverted Orientation | Jan. 04, 2010 Upright Orientation | Jan. 13, 2010 Upright Orientation |
| Appearance (Solution) | Clear, colorless, no ppt | NT | Slightly turbid solution |
| Appearance (Container) | No leakage observed, container intact | NT | No leakage observed, container intact |
| Fluticasone Propionate Assay | 51.4% LC* | 100.4% LC | 98.9% LC |
| Fluticasone Related Substances | RRT 0.09: 1.09% AUC<br>RRT 0.10: 0.43% AUC<br>RRT 0.12: 0.73% AUC<br><br>RRT 0.27: 0.97% AUC<br>RRT 0.32: 0.56% AUC<br>RRT 0.44: 0.24% AUC<br><br>RRT 0.51: 0.67% AUC<br>RRT 0.60: 0.30% AUC<br>RRT 0.76: 0.99% AUC<br>RRT 0.88: 1.32% AUC<br><br>Total: 7.54% | RRT 0.06: 0.44% AUC<br>RRT 0.09: 0.93% AUC<br>RRT 0.12: 0.53% AUC<br><br>RRT 0.27: 0.52% AUC<br>RRT 0.31: 0.07% AUC<br>RRT 0.36: 0.17% AUC<br><br>Total: 2.66% | RRT 0.11: 0.94% AUC<br>RRT 0.13: 0.71% AUC<br>RRT 0.28: 0.08% AUC<br><br>Total: 1.73% AUC |
| Cetirizine Assay | 98.6% LC | NT | 96.7% LC |
| Cetirizine Related Substances | RRT 0.46: 0.08% AUC<br>RRT 1.13: 0.70% AUC<br><br>Total: 0.78% | NT | RRT 1.13: 0.96% AUC<br><br>Total: 0.96% AUC |
| Benzalkonium chloride Assay | NT | NT | 98.7% LC |
| Disodium Edetate | NT | NT | 90.4% LC |
| pH | 7.1 | NT | 7.0 |
| Osmolality | 272 mOsm/Kg | NT | 274 mOsm/Kg |

RH = relative humidity, LC = label claim, AUC = area under curve, NT = not tested.
*The low assay values were attributed to the inverted orientation in which the stability samples were stored. Samples stored in the upright orientation were tested at the 2-week time point and subsequent time points, as reflected in the data shown.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A topical ophthalmic formulation consisting essentially of 0.24% cetirizine (w/v), 1% Polyethylene Glycol 400, NF, 0.2% Dibasic Sodium Phosphate, Anhydrous, USP, 0.25% Hypromellose, USP, 0.1% Polysorbate 80, NF, 1.8% Glycerin, USP, 0.01% Benzalkonium Chloride, NF, 0.025% Edetate Disodium, USP, and Purified Water, USP, wherein the formulation has a pH 6.8-7.2 and does not contain a cyclodextrin or other solubilizing compound.

2. The formulation of claim 1, wherein the cetirizine is present as cetirizine hydrochloride or dihydrochloride.

3. The formulation of claim 1, wherein the formulation is an aqueous formulation, an ointment, an oil, a suspension, an emulsion, or incorporated as a drug delivery device.

* * * * *